(12) United States Patent
Longacre et al.

(10) Patent No.: US 8,026,354 B2
(45) Date of Patent: Sep. 27, 2011

(54) **RECOMBINANT *PLASMODIUM FALCIPARUM* MEROZOITE SURFACE PROTEINS 4 AND 5 AND THEIR USE**

(75) Inventors: Shirley Longacre, Paris (FR); Hannah Polson, Paris (FR); Ronald Perraut, ointe a Pitre Cedex (FR); Faridabano Nato, Antony (FR)

(73) Assignees: Institut Pasteur, Paris (FR); Centre Nationale de la Recherche Scientifique, Paris (FR)

( * ) Notice: Subject to any disclaimer, the term of this patent is extended or adjusted under 35 U.S.C. 154(b) by 662 days.

(21) Appl. No.: 11/603,310

(22) Filed: Nov. 22, 2006

(65) Prior Publication Data

US 2008/0286805 A1    Nov. 20, 2008

Related U.S. Application Data

(60) Provisional application No. 60/739,973, filed on Nov. 23, 2005.

(51) Int. Cl.
| | |
|---|---|
| *C07H 21/02* | (2006.01) |
| *C12N 15/00* | (2006.01) |
| *C12N 15/09* | (2006.01) |
| *C12P 21/02* | (2006.01) |
| *C12P 19/00* | (2006.01) |
| *A61K 39/00* | (2006.01) |

(52) U.S. Cl. .................. 536/23.7; 435/320.1; 435/69.3; 435/69.1; 435/71.1; 424/265.1

(58) Field of Classification Search ........................ None
See application file for complete search history.

(56) References Cited

U.S. PATENT DOCUMENTS

2010/0092520 A1* 4/2010 Longacre et al. .......... 424/272.1

FOREIGN PATENT DOCUMENTS

WO    WO 0025728    * 3/2000

OTHER PUBLICATIONS

Kedzierski et al., Comparison of the protective efficacy of yeast-derived and *Escherichia coli*-derived recombinant merozoite surface protein 4/5 against lethal challenge by *Plasmodium yoelii*; Vaccine 2001, vol. 19, pp. 4661-4668.

Marshall et al., Close linkage of three merozoite surface protein genes on chromosome 2 of *Plasmodium falciparum*, Molecular and Biochemical Parasitology 1998, vol. 94, pp. 13-25.

Marshall et al., A second merozoite surface protein (MSP-4) of *Plasmodium falciparum* that contains an epidermal growth factor-like domain, Infection and Immunity 1997, vol. 65, pp. 4460-4467.

Polson et al., Gene polymorphism of *Plasmodium falciparum* merozoite surface proteins 4 and 5; Molecular and Biochemical Parasitology 2005, vol. 142, pp. 110-115.

Wang et al., Differences in epitope recognition, isotype and titer of antisera to *Plasmodium falciparum* merozoite surface protein 4 raised by different modes of DNA or protein immunization; Vaccine 2001, vol. 19, pp. 816-824.

Wang et al., Naturally acquired antibody responses to *Plasmodium falciparum* merozoite surface protein 4 in a population living in an area of endemicity in Vietnam; Infection and Immunity 2001, vol. 69, pp. 4390-4397.

* cited by examiner

*Primary Examiner* — S. Devi

(74) *Attorney, Agent, or Firm* — Finnegan, Henderson, Farabow, Garrett & Dunner LLP

(57) ABSTRACT

Accordingly, the invention provides constructs in which the nucleic acids encoding *Plasmodium falciparum* MSP4 and MSP5, and the resulting polypeptides, have been modified. More particularly, this invention provides constructs encoding recombinant MSP4 and MSP5 polypeptides, which are expressed as soluble, secreted polypeptides in a baculovirus-insect cell expression system. It was surprisingly found that the recombinant polypeptides contain an EGF-like domain at the C-terminus that is properly folded in the polypeptide.

11 Claims, 37 Drawing Sheets

*P. falciparum*
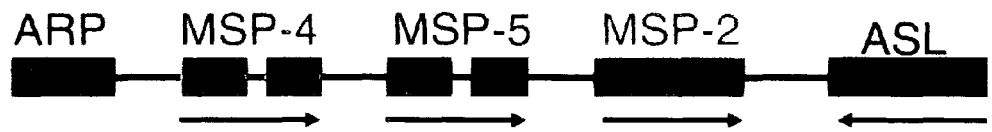
*P. vivax*
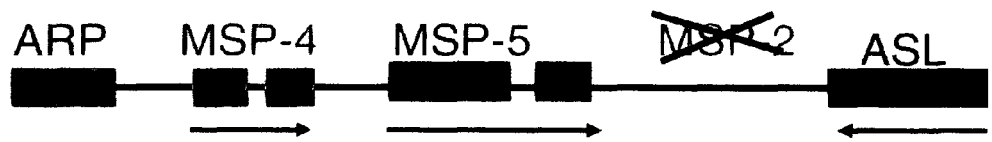
*P. knowlesi*
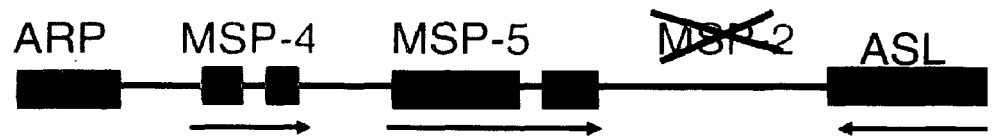
*P. Chabaudi*
*P. Berghei*
*P. yoelii*
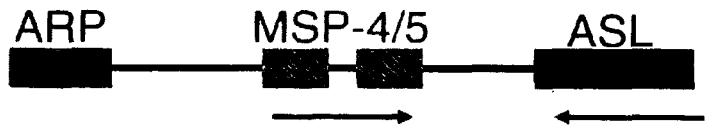
Figure 1. The genomic organisation of the *msp4* and msp5 gene locus in several different species of Plasmodium.

```
SALSA                                                   RVSTSDTPGGN
MSP4  MWIVKFLIVVHFFIICTINFDKLYISYSYNIVPENGRMLNMRILGEEKPNVDGVSTSDTPGGN

SALSA ESSSAFPQFIWSAEKKDEKEASEQGEEESHKKENSQESANGKDDVKEEKKTNEKKDDGKTDKVQ
MSP4  ESSSASPNLSDAAEKKDEKEASEQGEEESHKKENSQESANGKDDVKEEKKTNEKKDDGKTDKVQ

SALSA EKVLEKSPK
MSP4  EKVLEKSPKESQMVDDKKKTEAIPKKVVQPSSSNSG-GHVGEEEDHNEGEGEHEEEEHEEDD

MSP4  DDEDDDTYNKDDLEDEDLCKHNNGGCGDDKLCEYVGNRRVKCKCKEGYKLEGIECVELLSLAS

MSP4  SSLNLIFNSFITIFVVLLIN
```

*FIG. 2*

MSP4 synthetic gene

```
BamH I          1                                               Nde I    2
CCAggatccATGTGGATCGTAAAGTTCTTGATTGTGGTCCACTTCTTCATcatatgCACCATCAACTTCGACAAGCTC
                TTTCAAGAACTAACACCAGGTGAAGAAGTAgtatacGTGGTAGTTGAAGCTGTTCGAG
                                           38
         M  W  I  V  K  F  L  I  V  V  H  F  F  I  I  C  T  I  N  F  D  K  L 3                                       4
TACATTAGTTACTCTTACAACATCGTCCCTGAAAACGGACGTATGCTTAACATGAGGATCTTGGGTGAAGAAAAGCCT
ATGTAATCAATGAGAATGTTGTAGCAGGGACTTTTGCCTGCATACGAATTGTACTCCTAGAACCCACTTCTTTTCGGA
            37                                        36
 Y  I  S  Y  S  Y  N  I  V  P  E  N  G  R  M  L  N  M  R  I  L  G  E  E  K  P 5                                       6
AACGTTGACGGTGTGTCAACATCTAACACACCTGGCGGAAACGAGGCATCTAGTGCTTCTCCTAACCTTGCTGACGct
TTGCAACTGCCACACAGTTGTAGATTGTGTGGACCGCCTTTGCTCCGTAGATCACGAAGAGGATTGGAACGACTGCga
        35                                     34
 N  V  D  G  V  S  T  S  N  T  P  G  G  N  E  A  S  S  A  S  P  N  L  A  D  A Pst I                   7                                       8
GcagAAAAGAAGGACGAAAAGGAAGCAAGCGAGCAAGGCGAAGAATCCCACAAGAAGGAAAAACTCTCAGGAATCTGCA
CgtcTTTTCTTCCTGCTTTTCCTTCGTTCGCTCGTTCCGCTTCTTAGGGTGTTCTTCCTTTTGAGAGTCCTTAGACGT
        33                                      32
 A  E  K  K  D  E  K  E  A  S  E  Q  G  E  E  S  H  K  K  E  N  S  Q  E  S  A 9                               10
AACGGAAAAGACGACGTTAAGGAGGAGAAGAAGACCAACGAGAAGAAGGACGACGGAAAGACTGACAAGGTACAAGAA
TTGCCTTTTCTGCTGCAATTCCTCCTCTTCTTCTGGTTGCTCTTCTTCCTGCTGCCTTTCTGACTGTTCCATGTTCTT
                31                                      30
 N  G  K  D  D  V  K  E  E  K  K  T  N  E  K  K  D  D  G  K  T  D  K  V  Q  E Xba I                   11                                      12
AAGGTtctagaAAAGAGTCCCAAGGAGAGTCAAATGGTCGACGACAAGAAGAAGACCGAGGCCATTCCAAAGAAAGTC
TTCCAagatcTTTTCTCAGGGTTCCTCTCAGTTTACCAGCTGCTGTTCTTCTTCTGGCTCCGGTAAGGTTTCTTTCAG
                29                                     28
 K  V  L  E  K  S  P  K  E  S  Q  M  V  D  D  K  K  K  T  E  A  I  P  K  K  V Xho I          13                                      14
GTGCAGCCAAGctcgagCAACTCTGGAGGTCACGTCGGTGAAGAAGAAGACCACAACGAAGGAGAGGGAGAGCACGAA
CACGTCGGTTCgagctcGTTGAGACCTCCAGTGCAGCCACTTCTTCTTCTGGTGTTGCTTCCTCTCCCTCTCGTGCTT
                27                                      26
 V  Q  P  S  S  S  N  S  G  G  H  V  G  E  E  E  D  H  N  E  G  E  G  E  H  E 15                              16   Bgl II
GAGGAGGAAGAACACGAAGAAGACGATGACGACGAGGACGACGACACATACAACAAAGACGACTTGGAGGACGAagat
CTCCTCCTTCTTGTGCTTCTTCTGCTACTGCTGCTCCTGCTGCTGTGTATGTTGTTTCTGCTGAACCTCCTGCTtcta
                        25                                      24
 E  E  E  E  H  E  E  D  D  D  D  E  D  D  D  T  Y  N  K  D  D  L  E  D  E  D 17                                      18
ctTTGCAAGCACAACAACGGAGGATGTGGAGATGACAAGCTCTGCGAGTACGTTGGAAAACCGTCGCGTAAAATGTAAA
gaAACGTTCGTGTTGTTGCCTCCTACACCTCTACTGTTCGAGACGCTCATGCAACCTTTGGCAGCGCATTTTACATTT
                23                                      22
 L  C  K  H  N  N  G  G  C  G  D  D  K  L  C  E  Y  V  G  N  R  R  V  K  C  K 19                              EcoR I
TGTAAGGAAGGATACAAGTTGGAAGGAATTGAGTGCGTTGAACACCACCACCACCATC
ACATTCCTTCCTATGTTCAACCTTCCTTAACTCACGCAACTTGTGGTGGTGGTGGTAGTGATTcttaagTCTGCGGGG
                21                              20
 C  K  E  G  Y  K  L  E  G  I  E  C  V  E  H  H  H  H  H  H  *
```

*FIG. 3*

```
MSP4-EGF/His    MWIVKFLIVVHFFIICTINFDK---------------------------------------
MSP4p21/His     MWIVKFLIVVHFFIICTINFDKLYISYSYNIVPENGRMLNMRILGEEKP--*---------
MSP4p40/His     MWIVKFLIVVHFFIICTINFDKLYISYSYNIVPENGRMLNMRILGEEKPNVDGVSTSNTP
MSP4p30/His     MWIVKFLIVVHFFIICTINFDKLYISYSYNIVPENGRMLNMRIL-----------------

MSP4-EGF/His    ------------------------------------------------------------
MSP4p21/His     --------------*---------------------------------------------
MSP4p40/His     GGNEASSASPNLADAAEKKDEKEASEQGEESHKKENSQESANGKDDVKEEKKTNEKKDDG
MSP4p30/His     --------------AAEKKDEKEASEQGEESHKKENSQESANGKDDVKEEKKTNEKKDDG

MSP4-EGF/His    ------------------------------------------------------------
MSP4p21/His     ---------LEKSPKESQMVDDKKKTEAIPKKVVQPSSSNSGGHVGEEEDHNEGEGEHEE
MSP4p40/His     KTDKVQEKVLEKSPKESQMVDDKKKTEAIPKKVVQPSSSNSGGHVGEEEDHNEGEGEHEE
MSP4p30/His     KTDKVQEKVLEKSPKESQMVDDKKKTEAIPKKVVQPSSSNSGGHVGEEEDHNEGEGEHEE

MSP4-EGF/His    ---------*----------------DLCKHNNGGCGDDKLCEYVGNRRVKCKCKEGYKLEG
MSP4p21/His     EEEHEEDDDDEDDDTYNKDDLEDEDLCKHNNGGCGDDKLCEYVGNRRVKCKCKEGYKLEG
MSP4p40/His     EEEHEEDDDDEDDDTYNKDDLEDEDLCKHNNGGCGDDKLCEYVGNRRVKCKCKEGYKLEG
MSP4p30/His     EEEHEEDDDDEDDDTYNKDDLEDEDLCKHNNGGCGDDKLCEYVGNRRVKCKCKEGYKLEG

MSP4-EGF/His    IECVEHHHHHH
MSP4p21/His     IECVEHHHHHH
MSP4p40/His     IECVEHHHHHH
MSP4p30/His     IECVEHHHHHH
```

FIG. 5

MSP5 synthetic gene

```
       BamH I            1                                            2    Pme I
CCCggatccATGAACATTCTCTGTATTCTCAGCTACATTTACTTCTTCGTCATCTTCTACAGtttaaaCCTCAACAAC
         GACATAAGAGTCGATGTAAATGAAGAAGCAGTAGAAGATGTCaaattGGAGTTGTTG
                                          38
          M  N  I  L  C  I  L  S  Y  I  Y  F  V  I  F  Y  S  L  N  L  N  N 3                                       4   Spe I
AAAAACGAGAACTTCTTGGTGGTCCGCAGACTCATGAACGACGAAAAGGGAGAAGGTGGCTTCactagtAAGAACAAG
TTTTTGCTCTTGAAGAACCACCAGGCGTCTGAGTACTTGCTGCTTTTCCCTCTTCCACCGAAGtgatcaTTCTTGTTC
 37                                          36
  K  N  E  N  F  L  V  V  R  R  L  M  N  D  E  K  G  E  G  G  F  T  S  K  N  K 5                                  6
GAAAACGGAAACAACAACAGGAACAACGAGAACGAACTCAAAGAAGAAGGATCTTTGCCCACTAAGATGAACGAGAAA
CTTTTGCCTTTGTTGTTGTCCTTGTTGCTCTTGCTTGAGTTTCTTCTTCCTAGAAACGGGTGATTCTACTTGCTCTTT
                                                   34
  E  N  G  N  N  N  R  N  N  E  N  E  L  K  E  E  G  S  L  P  T  K  M  N  E  K Sac II             7                                  8
AACAGTAACTccgcggATAAGCAACCAAACGACATCTCCCACGACGAAAGCAAGAGCAACAGTAACAACGCCCAAAAC
TTGTCATTGAggcgccTATTCGTTGGTTTGCTGTAGAGGGTGCTGCTTTCGTTCTCGTTGTCATTGTTGCGGGTTTTG
          33                                         32
  N  S  N  S  A  D  K  Q  P  N  D  I  S  H  D  E  S  K  S  N  S  N  N  A  Q  N 9                Xho I            10
ATCCAAAAGGAACCTGAAGAGAAGGAAAAACTCAAACCCCAACCTCGActcgagTGAAAACTCCGCTGAAAGTGCTACT
TAGGTTTTCCTTGGACTTCTCTTCCTTTTGAGTTTGGGGTTGGAGCTgagctcACTTTTGAGGCGACTTTCACGATGA
                  31                                       30
  I  Q  K  E  P  E  E  K  E  N  S  N  P  N  L  D  S  S  E  N  S  A  E  S  A  T 11                             12   Xba I
AGAAGCGTCGACATCAGTGAACACAACTCAAACAACCCCGAAAACTAAAGAAGAAAACGGAGAAGAACCtctagaCCTG
TCTTCGCAGCTGTAGTCACTTGTGTTGAGTTTGTTGGGGCTTTGATTTCTTCTTTTGCCTCTTCTTGGagatctGGAC
                                  29                               28
  R  S  V  D  I  S  E  H  N  S  N  N  P  E  T  K  E  E  N  G  E  E  P  L  D  L 13                                            14
GAAATTAACGAAAACGCAGAAATCGGCCAGGAACCTCCAAACCGTCTTCACTTCGACAACGTTGACGACGAAGTACCA
CTTTAATTGCTTTTGCGTCTTTAGCCGGTCCTTGGAGGTTTGGCAGAAGTGAAGCTGTTGCAACTGCTGCTTCATGGT
                27                                              26
  E  I  N  E  N  A  E  I  G  Q  E  P  P  N  R  L  H  F  D  N  V  D  D  E  V  P 15                                             16
CATTACTCAGCCCTGAGGTACAACAAGGTCGAGAAGAACGTAACCGACGAGATGCTCTTGTACAACATGATGTCCGAC
GTAATGAGTCGGGACTCCATGTTGTTCCAGCTCTTCTTGCATTGGCTGCTCTACGAGAACATGTTGTACTACAGGCTG
                       25                                    24
  H  Y  S  A  L  R  Y  N  K  V  E  K  N  V  T  D  E  M  L  L  Y  N  M  M  S  D 17 Pst I                  Bgl II                          18
CAAAACCGCAAAAGCTGTGCTATCAACAACGGTGGctgcagTGACGACCagatctGCATCAACATCAACAACATCGGT
GTTTTGGCGTTTTCGACACGATAGTTGTTGCCACCgacgtcACTGCTGGtctagaCGTAGTTGTAGTTGTTGTAGCCA
              23                                    22
  Q  N  R  K  S  C  A  I  N  N  G  G  C  S  D  D  Q  I  C  I  N  N  N  I  G Kpn I        19
GTGAAGTGCATTTGTAAGGATGGATACCTACTTggtaccAAGTGCATTCACCACCACC
CACTTCACGTAAACATTCCTACCTATGGATGAAccatggTTCACGTAAGTGGTGGTGGTGGTGACTcttaagTCT
              21                                            20
  V  K  C  I  C  K  D  G  Y  L  L  G  T  K  C  I  H  H  H  H  H  H  *
```

FIG. 6

```
MSP4-p40    MWTVKFLIVVHFFIICTINFDKLYISYSNIVPENGRMLNMRILGEEKPNVDGVSTSNTP
MSP4-p30    MWTVKFLIVVHFFIICTINFDKLYISYSNIVPENGRMLNMRIL-----------------

GGNEASSASPNLADAAEKKDEKEASEQGEESHKKENSQESANGKDDVKEEKKTNEKKDDG
            ----------------AAEKKDEKEASEQGEESHKKENSQESANGKDDVKEEKKTNEKKDDG
                            MSP4-p20

KTDKVQEKVLEKSPKESQMVDDKKKTEAIPKKVVQPSSSNSGGHVGEEEDHNEGEGEHEE
            KTDKVQEKVLEKSPKESQMVDDKKKTEAIPKKVVQPSSSNSGGHVGEEEDHNEGEGEHEE

EEEHEEDDDDEDDDTYNKDDLEDEDLCKHNNGGCGDDKLCEYVGNRRVKCKCKEGYKLEG
            EEEHEEDDDDEDDDTYNKDDLEDEDLCKHNNGGCGDDKLCEYVGNRRVKCKCKEGYKLEG

IECVEHHHHHH
            IECVEHHHHHH
```

FIG. 9

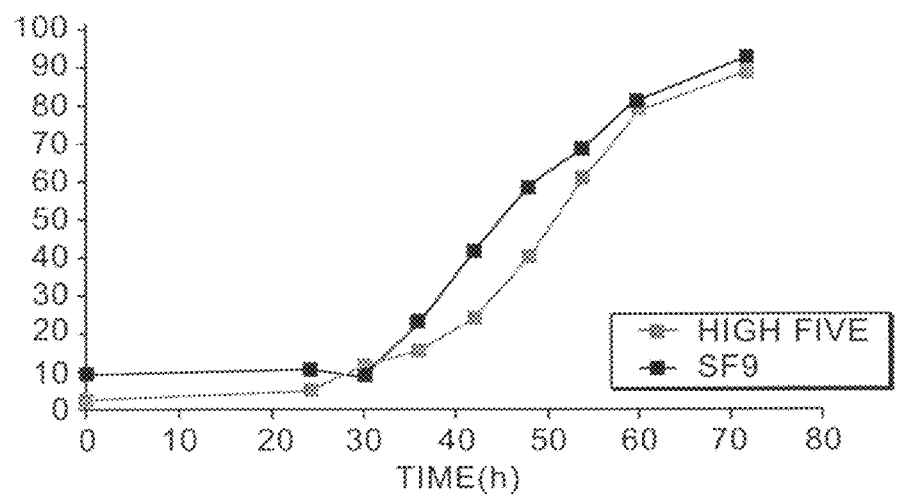
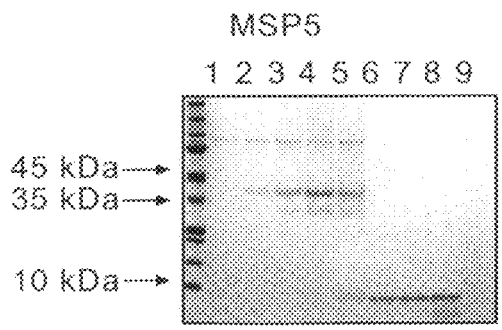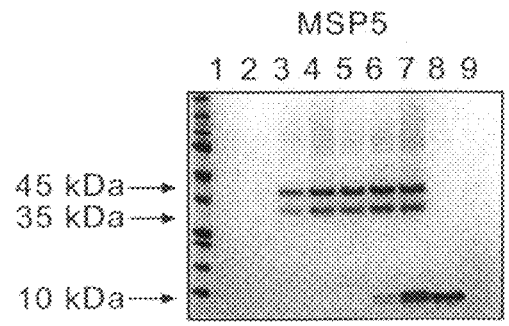
FIG. 11

FIG. 12C

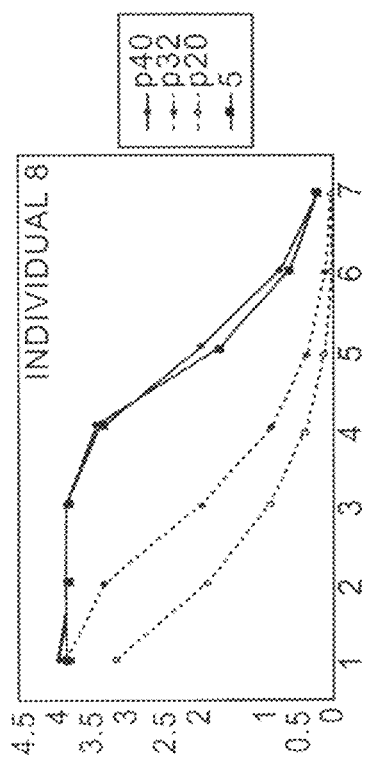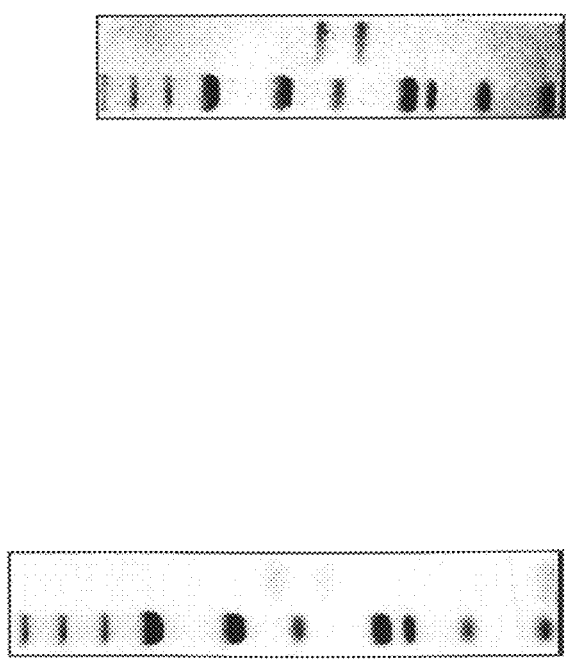
FIG. 15B

Western blot
PfMSP4 mAb L11-16

Western blot
PfMSP4 mAb F12-7

Western blot
PfMSP5 mAb G21-2

Western blot
PfMSP5 mAb J18-14

DILUTION OF SHI

```
pfmsp4    MWIVKFLIVVHFFIICTINFDKLYISYSYNIVPENGRMLNMRILGEEKPNVDGVSTSNTP
pvmsp4    MKVAYFLSVLDLLIIFSLYFDGRRSAFAG----IAACIRHGRILGEGGEQSGGASGGSS-
          *-:.-**-*:.,::-::-----::-------.-:-:-*****---:-.*.*-..:- pfmsp4    GGNESSSASPNLSDAAEKKDEKEASEQGEESHKKENSQESANGKDDVKEEKKTNEKKDDG
pvmsp4    GGSSGDSSGGLSGGSSGGPSPPAGSSGSGGSDPANSATGP--------------------
          *..*..:*-.**..:.---.--*....*,-.-.--**--,.----------------- pfmsp4    KTDKVQEKVLEKSPKESQMVDDKKKTEAIPKKVVQPSSSNSGGHVGEEEDHNEGEGEHEE
pvmsp4    ---------------QNSTPGSGGQTGDHSAEAENGDYNEQGDDHGDDHGDDHG-DDHGD
                         :.,--..--:*---.-:.-:-.-:.*..-*::..:,.*-.:*-:

pfmsp4    EEEHEEDDDDEDDDTYNKDDLED-EDLCKHNNGGCGDDKLCEYVGNRRVKCKCKEGYKLE
pvmsp4    EQDGEDYDDAEDDDLYELSEVDENANLCLDNNGGCGDDKICENLGKGIVKCLCKPGYKLV
          *::-*:--**-*:-.::::--:-.*****;-:*:--*.-****- pfmsp4    GIECVELLSLASSSLNLIFNSPITIFVVILLIN
pvmsp4    GTECVE--SSKSSSLNSPFCWPLLVIIVLASIN
          *-****--*...*****-:*--*;-:;;*:--**
```

FIG. 26

```
PfMSP4/p21      MWIVKFLIVVHFFIICTINFDKLYISYSYNIVPENGRMLNMRIL---------------
PfMSP4/p21ss1   MWIVKFLIVVHFFIICTINFDKLYISYSYNIVPENGRMLNMRILGEEKPNVDGVSTS---   p21.1
PfMSP4/p21ss2   MWIVKFLIVVHFFIICTINFDKLYISYSYNIVPENGRMLNMRILGEEKP----------   p21.2

------------------------------------------------------------
                ------------------------------------------------------------
                ------------------------------------------------------------

----------EKSPKESQMVDDKKKTEAIPKKVVQPSSSNSGGHVGEEEDHNEGEGEHEE
                ---------LEKSPKESQMVDDKKKTEAIPKKVVQPSSSNSGGHVGEEEDHNEGEGEHEE    p20
                ---------LEKSPKESQMVDDKKKTEAIPKKVVQPSSSNSGGHVGEEEDHNEGEGEHEE    p20

EEEHEEDDDDEDDDTYNKDDLEDEDLCKHNNGGCGDDKLCEYVGNRRVKCKCKEGYKLEG
                EEEHEEDDDDEDDDTYNKDDLEDEDLCKHNNGGCGDDKLCEYVGNRRVKCKCKEGYKLEG
                EEEHEEDDDDEDDDTYNKDDLEDEDLCKHNNGGCGDDKLCEYVGNRRVKCKCKEGYKLEG

IECVEHHHHHH
                IECVEHHHHHH
                IECVEHHHHHH
```

FIG. 29

```
PfMSP4p40   MWIVKFLIVVHFFIICTINFDKLYISYSYNIVPENGRMLNMRILGEEKPNVDGVSTSNTP
PvMSP4      MKVAYFLSVLDLLIIFSLYFDGRRSAFAG----IAACIRHGRILGEGGEQSGGASGGSSG
            * :. ** *:.::** :: **    :::     . : : *****   : .*.* ...:

PfMSP4p40   GGNEASSASPNLADAAEKKDEKEASEQGEESHKKENSQESANGKDDVKEEKKTNEKKDDG
PvMSP4      GSSGDSSGG---------------LSGGSSGGPSPPAGSSGSGGSDPANSATGPQNSTPG
            *..  **..                .*...  . :.*..* .*  :. :..  ::. *

PfMSP4p40   KTDKVQEKVLEKSPKESQMVDDKKKTEAIPKKVVQPSSSNSGGHVGEEEDHNEGEGEHEE
PvMSP4      SGGQTGDHSAEAENGD-------------------YNEQGDDHGDDHGDDHG-DDHGD
            . .:. ::  * . :                    .:.*.. *::...:.* .:* :

PfMSP4p40   EEEHEEDDDDEDDDTYNKDDLED-EDLCKHNNGGCGDDKLCEYVGNRRVKCKCKEGYKLE
PvMSP4      EQDGEDYDDAEDDDLYELSEVDENANLCLDNNGGCGDDKICENLGKGIVKCLCKPGYKLV
            *:: *: ** **** *: .:::: :** .**********:** :*: *** ** ****

PfMSP4p40   GIECVE HHHHHH
PvMSP4      GTECVESHHHHHH
            * **** ******
```

FIG. 31

RECOMBINANT *PLASMODIUM FALCIPARUM* MEROZOITE SURFACE PROTEINS 4 AND 5 AND THEIR USE

CROSS-REFERENCE TO RELATED APPLICATION

This application is based on and claims the benefit of U.S. Provisional Application Ser. No. 60/739,973, filed Nov. 23, 2005. The entire disclosure of this Provisional application is relied upon and incorporated by reference herein

FIELD OF THE INVENTION

This invention is directed to recombinant isolated polypeptides, the nucleic acids encoding such polypeptides, processes for production of recombinant forms of such polypeptides, antibodies generated against these polypeptides, and the use of such polypeptides and antibodies in diagnostic methods, kits, vaccines, or anti-parasite therapy.

BACKGROUND OF THE INVENTION

Malaria is responsible for approximately 2 million deaths per year worldwide, mostly African children under 5 years old, and places an enormous public health burden on many of the world's poorest countries. This burden is increasing at an alarming rate, as drug resistance in both the parasite and its mosquito vectors spreads, exacerbating the urgent need for an effective vaccine.

The most promising blood stage vaccine candidates examined so far are merozoite surface protein 1 (MSP1) and an apical membrane antigen (AMA1). Humoral immune responses targeting these surface antigens are found to be correlated with reduced disease incidence, and in vitro, such antibodies can inhibit parasite re-invasion of red blood cells (RBC) [1-3]. However, these antigen genes generally display a disproportionately high number of non-synonymous single nucleotide polymorphisms (nsSNPs) compared to genes coding for proteins that are not accessible to immune effectors [4-6], and some of these nsSNPs encode radical amino acid substitutions that clustered within the regions of the protein most accessible to the host immune system [7]. Such amino acid polymorphisms could function in immune evasion by altering both B and T cell epitopes [4,8]. It is now generally accepted that any functional malaria vaccine will need to be composed of several allelic types of each target antigen in the hope of inducing a multi-allelic response and/or conserved regions of several target antigens.

More particularly, there exists a need in the art for antigens that can be used in the diagnosis and treatment of malaria and in particular of *Plasmodium falciparum* malaria and *Plasmodium vivax* malaria. In particular, there is a need for conserved antigens associated with specific immune responses that confer protection from disease in endemic regions, and the assessment of their suitability as components of a multi-valiant malaria vaccine.

SUMMARY OF THE INVENTION

This invention aids in fulfilling these needs in the art. The invention provides a purified or recombinant nucleic acid molecule comprising a DNA sequence of SEQ ID NOS: 1, 2, 3, 4, 5, 6, 7, or 8 and a purified or recombinant nucleic acid molecule encoding the amino acid sequence of SEQ ID NOS: 9, 10, 11, 12, 13, 14, 15, 16, 17, 18, 19, 20, 21, or 22. The invention also encompasses purified nucleic acid molecules complementary to these sequences.

The invention also encompasses purified polypeptides encoded by the purified or recombinant nucleic acid molecules comprising a DNA sequence of SEQ ID NOS: 1-8, as predicted by the sequence.

The invention includes purified double-stranded nucleic acid molecules comprising the DNA sequence of SEQ ID NOS: 1-8, and purified double-stranded nucleic acid molecules encoding the amino acid sequence of SEQ ID NOS: 9-22. Both single-stranded and double-stranded RNA and DNA nucleic acid molecules are encompassed by the invention. These molecules can be used to detect both single-stranded and double-stranded RNA and DNA variants encoding polypeptides encompassed by the invention. A double-stranded DNA probe allows the detection of nucleic acid molecules equivalent to either strand of the nucleic acid molecule.

Purified nucleic acid molecules that hybridize to a denatured, double-stranded DNA comprising the DNA sequence of SEQ ID NOS: 1-8, and encoding the amino acid sequence of SEQ ID NOS: 9-22 under conditions of moderate stringency in 50% formamide and 6×SSC, at 42° C. with washing conditions of 60° C., 0.5×SSC, 0.1% SDS are encompassed by the invention.

The invention further encompasses purified nucleic acid molecules derived by in vitro mutagenesis from SEQ ID NOS: 1-8. In vitro mutagenesis includes numerous techniques known in the art including, but not limited to, site-directed mutagenesis, random mutagenesis, and in vitro nucleic acid synthesis.

The nucleic acid molecules of the invention, which include DNA and RNA, are referred to herein as "recombinant MSP4 and MSP5 nucleic acids" or "recombinant MSP4 and MSP5 DNA", and the amino acids encoded by these molecules are referred to herein as "recombinant MSP4 and MSP5 polypeptides" or "the polypeptides of the invention".

The invention also encompasses purified nucleic acid molecules degenerate from SEQ ID NOS: 1-8 as a result of the genetic code, purified nucleic acid molecules, which are allelic variants of recombinant MSP4 and MSP5 nucleic acids, or a species homolog of recombinant MSP4 and MSP5 nucleic acids. The invention also encompasses recombinant vectors that direct the expression of these nucleic acid molecules and host cells transformed, transfected or infected with these vectors.

Purified polyclonal or monoclonal antibodies that bind to recombinant MSP4 or MSP5 polypeptides are encompassed by the invention and are referred to herein as "the antibodies of the invention".

The invention further encompasses methods for the production of recombinant MSP4 and MSP5 polypeptides, including culturing a host cell under conditions promoting expression, and recovering the polypeptide from the culture medium or cellular pellets. Especially, the expression of recombinant MSP4 and MSP5 polypeptides in baculovirus insect expression systems is encompassed by the invention.

This invention also provides labelled recombinant MSP4 and MSP5 polypeptides. Preferably, the labelled polypeptides are in purified form. It is also preferred that the unlabelled or labelled polypeptide is capable of being immunologically recognized by human body fluid containing antibodies to malaria. The polypeptides can be labelled, for example, with an immunoassay label selected from the group consisting of radioactive, enzymatic, fluorescent, chemiluminescent labels, and chromophores.

Immunological complexes between the recombinant MSP4 or MSP5 polypeptides of the invention and antibodies recognizing those are also provided. The immunological complexes can be labelled with an immunoassay label selected from the group consisting of radioactive, enzymatic, fluorescent, chemiluminescent labels, and chromophores.

Furthermore, this invention provides an in vitro method for detecting MSP4 and/or MSP5 polypeptides of a *Plasmodium* parasite. The method comprises providing a composition comprising a biological material suspected of containing MSP4 and/or MSP5 polypeptides of a *Plasmodium* parasite (malaria parasite), and assaying for the presence of MSP4 and/or MSP5 polypeptides of a *Plasmodium* parasite. The MSP4 and MSP5 polypeptides of a *Plasmodium* parasite are typically assayed by electrophoresis or by immunoassay with the antibodies of the invention. This method can be used for the detection of *Plasmodium* parasites in a biological sample, and in a preferred embodiment for detection of *Plasmodium falciparum* and *Plasmodium vivax* parasites.

This invention also provides an in vitro diagnostic method for the detection of the presence or absence of antibodies, which bind to an antigen comprising the recombinant or purified MSP4 or MSP5 polypeptides of the invention or mixtures thereof. The method comprises contacting the antigen with a biological fluid for a time and under conditions sufficient for the antigen and antibodies in the biological fluid to form an antigen-antibody complex, and then detecting the formation of the complex. The detection step can further comprise measuring the formation of the antigen-antibody complex. The formation of the antigen-antibody complex is preferably measured by immunoassay based on Western blot technique, ELISA (enzyme linked immunosorbent assay), indirect immunofluorescent assay, or immunoprecipitation assay. This method can be used for the detection of an immunological response to a *Plasmodium* parasite in a biological fluid coming from an animal or a human patient malaria infected. In a preferred embodiment this method can be used for the detection of an immunological response to a *Plasmodium falciparum* infection or a *Plasmodium vivax* infection.

A diagnostic kit for the detection of the presence or absence of antibodies, which bind to the recombinant MSP4 or MSP5 polypeptides of the invention or mixtures thereof, contains antigen comprising the recombinant MSP4 and/or MSP5 polypeptides, or mixtures thereof, and means for detecting the formation of immune complexes between the antigen and antibodies. The antigen and the means are present in an amount sufficient to perform the detection.

A diagnostic kit for the detection of the presence or absence of MSP4 and/or MSP5 polypeptides of *Plasmodium* parasite, contains the antibodies of the invention, and means for detecting the formation of immune complexes between an antigen and the antibodies. The antibodies and the means are present in an amount sufficient to perform the detection.

This invention also provides an immunogenic composition comprising a recombinant MSP4 or MSP5 polypeptide of the invention or a mixture thereof in an amount sufficient to induce an immunogenic or protective response in vivo, in association with a pharmaceutically acceptable immunostimulator therefore. A vaccine composition of the invention comprises a sufficient amount of the recombinant MSP4 and/or MSP5 polypeptide and a pharmaceutically acceptable immunostimulator therefore to induce neutralizing antibodies.

The MSP4 and MSP5 polypeptides of the invention are thus useful as a portion of a diagnostic composition for detecting the presence of antibodies to antigenic proteins associated with malaria.

In addition, the recombinant MSP4 and MSP5 polypeptides can be used to raise antibodies for detecting the presence of antigenic proteins associated with malaria.

The polypeptides of the invention can be also employed to raise neutralizing antibodies that either inactivate the parasite, reduce the viability of the parasite in vivo, or inhibit or prevent parasite replication. The ability to elicit parasite-neutralizing antibodies is especially important when the polypeptides of the invention are used in immunizing or vaccinating compositions.

Following is a vaccine, which includes (A) the natural signal sequence (B) a C-terminal His tag and (C) the acid repeat region that resembles that of the *P. falciparum* antigen most strongly correlated with protective antibody responses in the field (MSP4p20).

[SEQ ID NO: 30]
MKVAYFLSVLDLLIIFSLYFDGRRSAFAGIAACIRHGRILGEGGE/QNST

PGSGGQTGDHSAEAENGDYNEQGDDHGDDHGDDHGDDHGDEQDGEDYDDA

EDDDLYELSEVDENANLCLDNNGGCGDDKICENLGKGIVKCLCKPGYKLV

GTECVEHHHHHH

BRIEF DESCRIPTION OF THE DRAWINGS

This invention will be described with reference to the drawings in which:

FIG. 1 depicts the genomic organization of the msp4 and msp5 gene locus in several different species of *Plasmodium*. Cross species conservation of these genes is indicative of a fundamental function.

FIG. 2 shows that the sequence of SALSA is 92% identical to MSP-4 of *Plasmodium falciparum* (PfMSP4). The SALSA sequence (SEQ ID NO: 31) is known to harbour both B and T-cell epitopes. The PfMSP4 sequence (SEQ ID NO: 32) is shown in Black and the SALSA sequence is shown in Grey.

FIG. 3 shows the full synthetic gene sequence of PfMSP4 (SEQ ID NOS 33-35). All sequence shown in this Figure was present in oligonucleotides. The gene sequence of PfMSP4 is coded by overlapping oligo-sequences num

FIG. 9 is a sequence alignment highlighting the N-terminal sequences of each MSP4 product: p40, p30 and p20. The signal sequence identified in this study is highlighted in Grey. The N-terminal sequence of each product is shown in blue BOLD type. Figure discloses SEQ ID NOS 12 and 10, respectively, in order or appearance.

FIG. 11 shows PfMSP5 expression over time in two different insect cell lines. Cell death was calculated by mixing cell suspensions 1:1 with 4% trypan blue and counting total cells and blue cells against a grid under a cover slip. Protein was purified from culture SN at 24, 30, 36, 42, 48, 54, 60 and 72 h post infection (lanes 1-8, respectively) and 20 uL of the eluted protein was resolved in 4-12% Bis-Tris gels (Invitrogen) and stained with SimplyBlue™ safe stain (Invitrogen). These protein species were not seen in uninfected cell culture (lane 9).

The ELISA profile generated for each serum is shown above each blot in FIGS. 16A and 16B, which depict the Western blots for two monoclonal antibodies, mAb L11-16 and mAb F12-7, that specifically recognize epitopes on PfMSP4, p40 and p20. Legend: nR=non reduced, R=reduced by invitrogen commercial buffer, iR=irreversibly reduced by DTT and acrylamide.

Figure 16A:
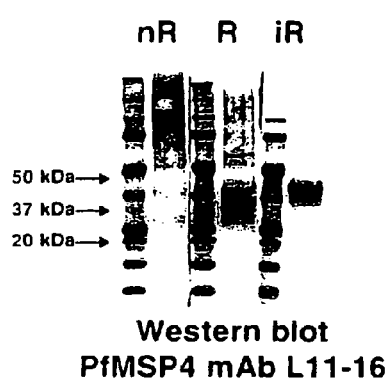
Figure 16B:
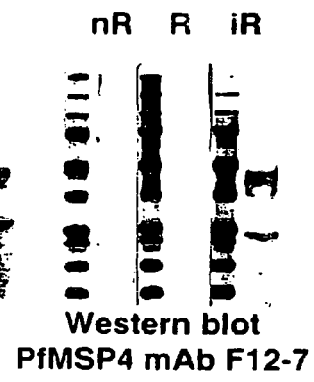
Figure 17A:
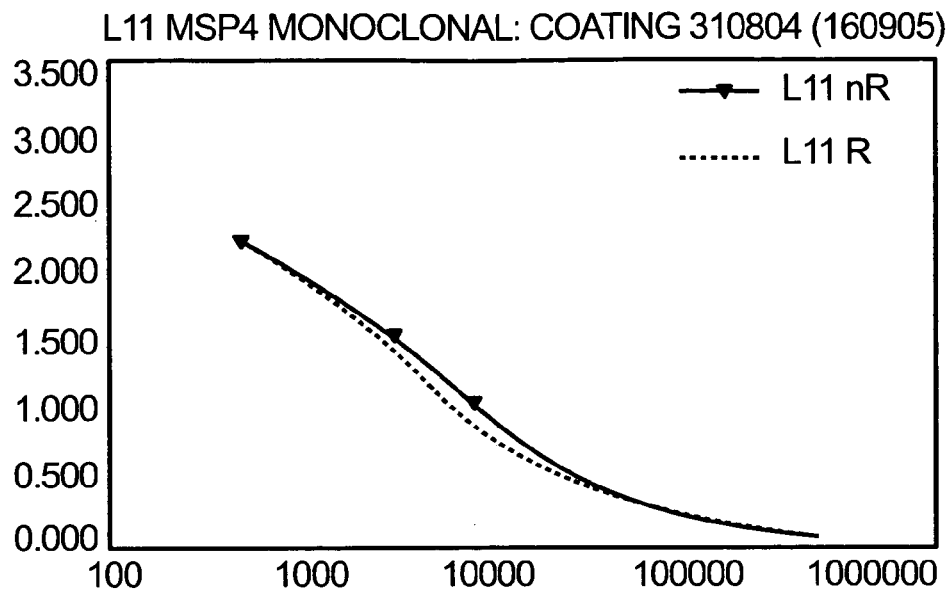
Figure 17B:
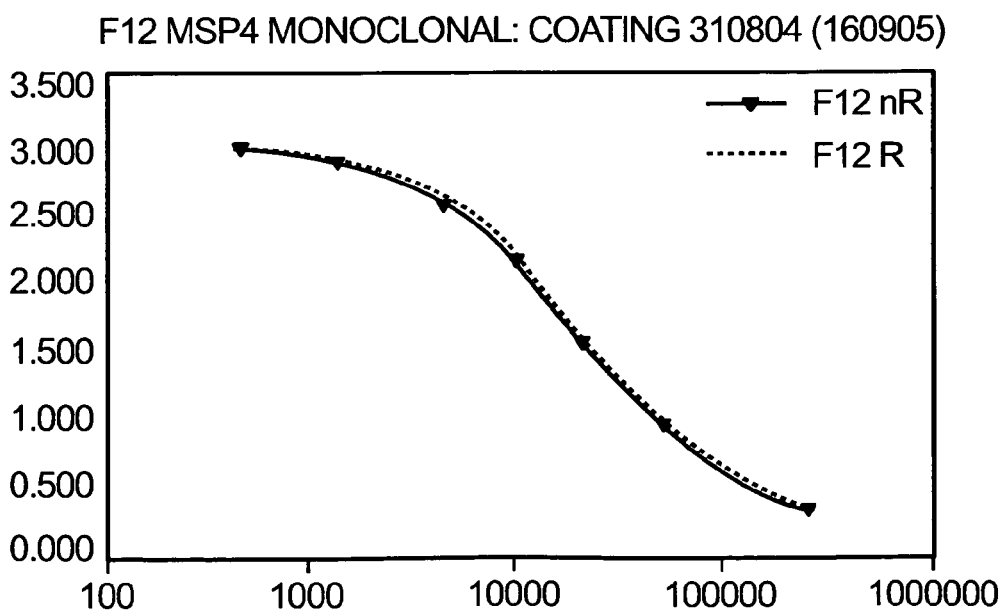

FIGS. 17A and 17B depict dilution factor α-axis) as a function of OD or absorbance (y-axis) for the mAbs in FIGS. 16A and 16B, respectively.

Figure 18A:
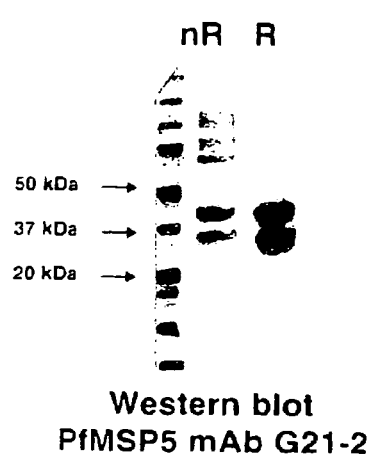
Figure 18B:
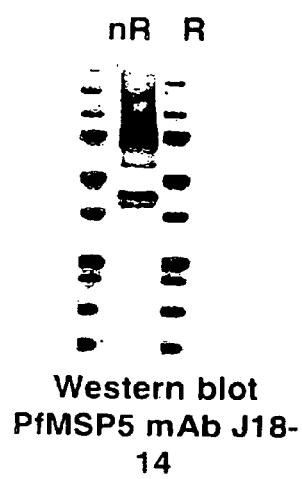

FIGS. 18A and 18B depict the Western blots for two monoclonal antibodies, mAb G21-2 and mAb J18-4, that specifically recognize epitopes on PfMSP5, p45 and p35. Legend: nR=non reduced, R=reduced by invitrogen commercial buffer, iR=irreversibly reduced by DTT and acrylamide.

Figure 19A:
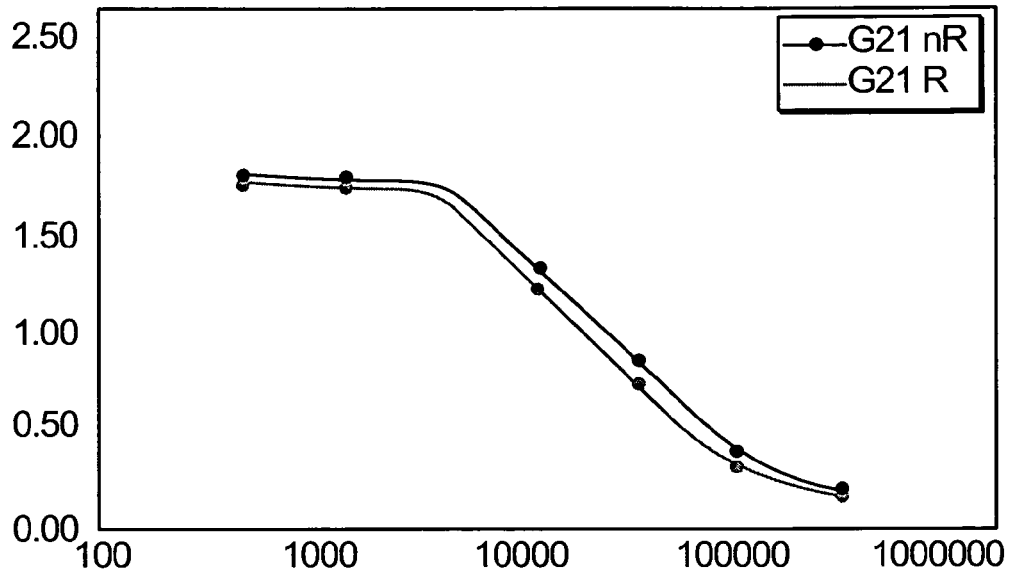
Figure 19B:
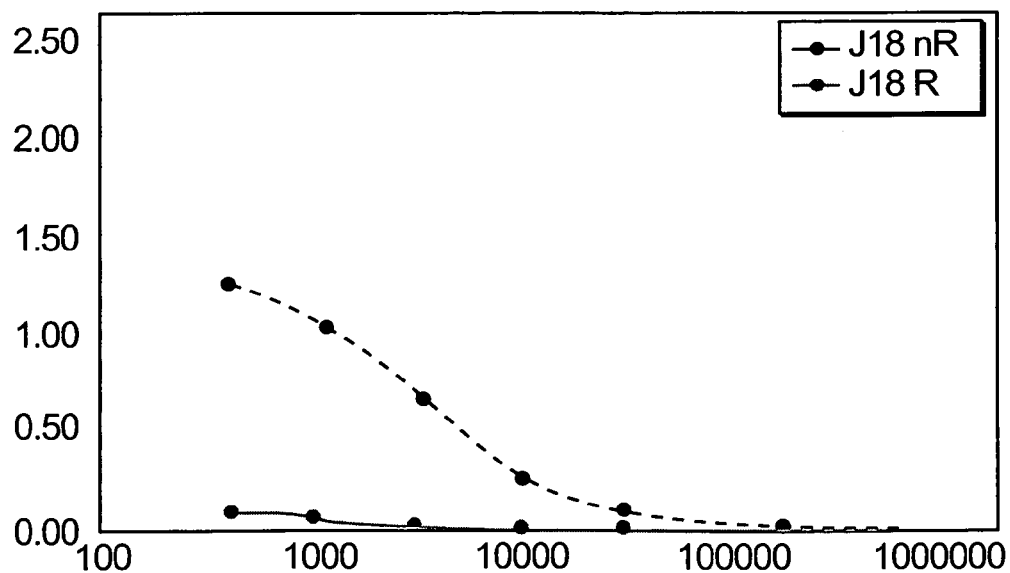

FIGS. 19A and 19B depict dilution factor (x-axis) and a function of OD or absorbance (y-axis) for the mAbs in FIGS. 18A and 18B, respectively.

Figure 20A:
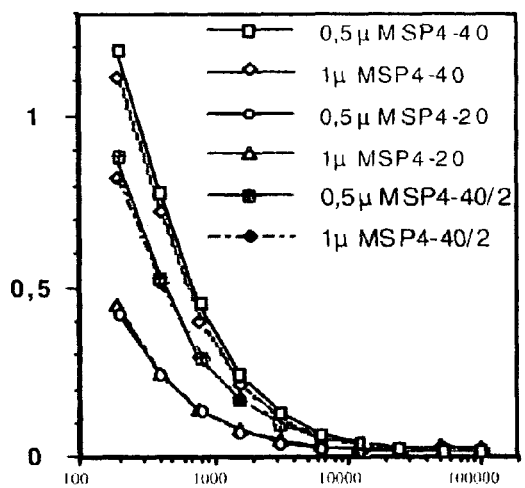
Figure 20B:
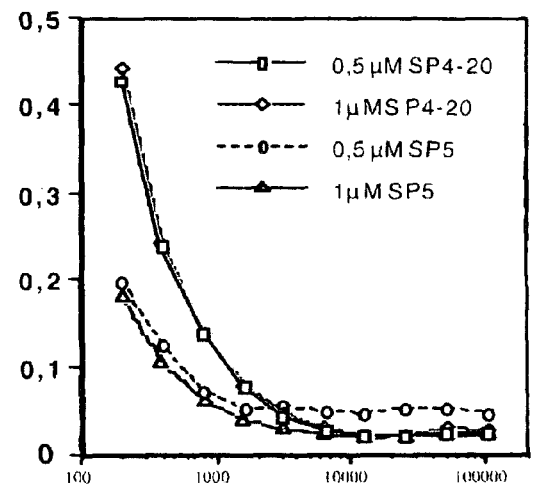
Figure 21:
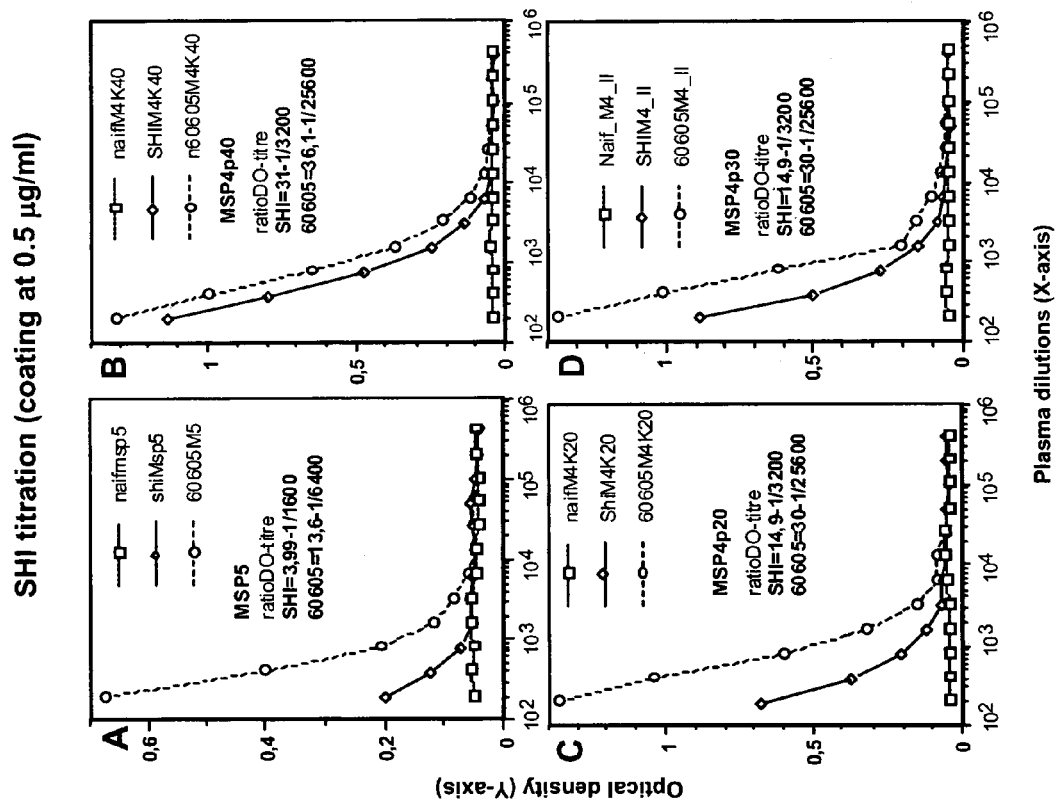
Figure 22A:
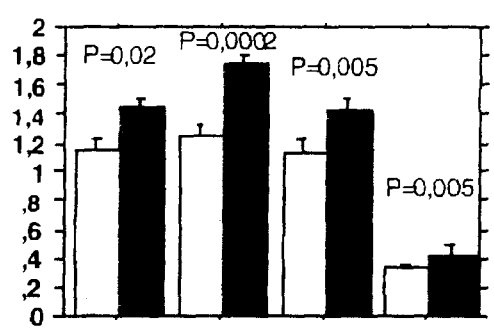
Figure 22B:
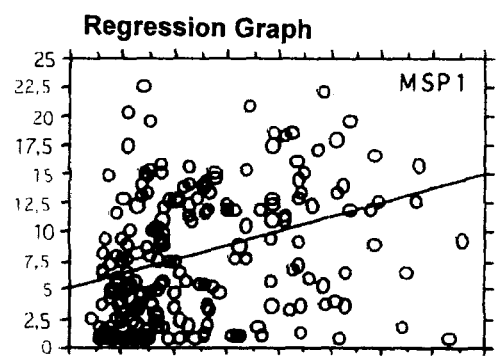
Figure 22C:
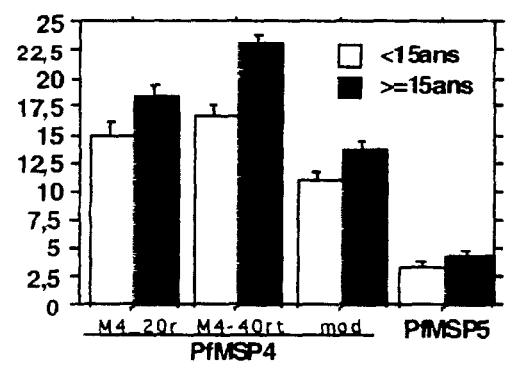
Figure 22D:
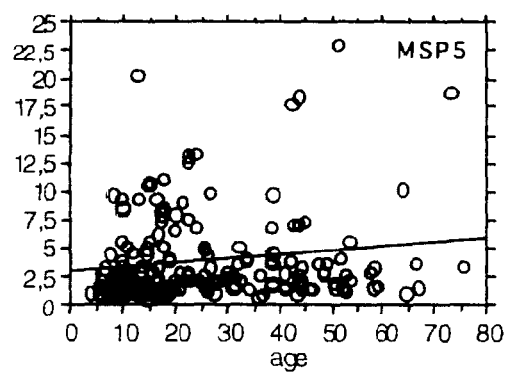

FIG. 20A-B depict ELISA analysis performed to optimise the protein coating concentration. Plates were coated overnight with 0.5 or 1 μg/mL of protein in PBS, adding 100 μL/well. Panel (A) shows data obtained with the three different MSP4 derived antigens, MSP4p40, MSP4p30 (here named MSP4p40/2) and MSP4p20. Panel (B) shows data obtained with MSP5, plotted with the MSP4p20 data from panel (A) to demonstrate the different strength of the responses. Since the optical densities observed were nearly identical using either concentration, the lower coating concentration (0.5 μg/mL) was used in all subsequent analyses.

FIG. 21A-D depict ELISA analysis of control sera from naive individuals (naïf), hyper immune adults (shi), and an individual from the Dielmo cohort of 2005 (60605). Plates were coated with 0.5 μg/mL of MSP5 (A), MSP4p40 (B), MSP4p20 (C), and MSP4p30 (D), and reactions were carried out at varying dilutions of the anti-sera (3-fold dilution series). All antigens were recognised by immune sera and not by the malaria naive control.

FIG. 22A-D depict antibody responses of individuals from the Ndiop cohort of 2000, stratified by age as those over and under 15 years of age. Panel (A) shows ELISA data in the form of optical density for the antigens (left to right) MSP4p20, MSP4p40, MSP4p30, and MSP5. Panel (C) shows the same data in the form of OD ratio. Panel (B) individual antibody responses to MSP1p19 are plotted as OD ratio as a function of age for the Ndiop 2000 cohort, while panel (D) shows the ELISA OD ratio obtained against MSP5 with the same sera.

Figure 23:
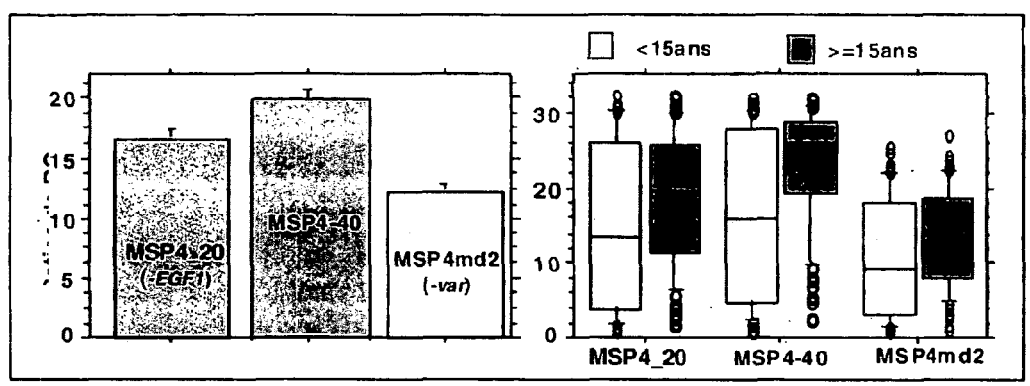

FIG. 23 depicts variation in the recognition of MSP4 and its derivatives by sera from the Ndiop 2000 cohort. The left hand panel shows the average response plotted as OD ratio for MSP4p20, MSP4p40, and MSP4p30 (equals MSP4md2). The right hand panel shows the upper and lower quartiles and the data spread for the antibody responses to each MSP4 antigen as a function of age.

FIG. 24 depicts antibody dependent monocyte mediated cytotoxicity measured as induced oxidative bursts in the presence of specific sera. Sera were divided into those giving an OD ratio above or below the median response of the cohort. Panel (A) shows data from sera divided as a function of MSP5 reactivity (above or below an OD ratio of 2.4), and panel (B) shows data from sera divided as a function of MSP4p40 reactivity (above or below an OD ratio of 20). Their ability to induce an oxidative burst in the presence of PBMC (peripheral blood mononuclear cells) and *P. falciparum* merozoites was analysed using chemiluminescence. In both groups, an increase in oxidative burst was seen with individuals showing high OD ratio.

FIG. 25 depicts the antibody isotype profile for each antigen analysed using IgG specific secondary antibody reagents. Isotype profiles are show for MSP4p40 (panel A) and MSP5 (panel B). Data is plotted as a function of age (above and below the age of 15).

FIG. 26 is an alignment of amino acid sequences of PfMSP4 (SEQ ID NO: 41) and PvMSP4 (SEQ ID NO: 42). Several features of the Pf sequence have been highlighted (i) the secretory and GPI attachment signals are shown in green, (ii) the sequence known as SALSA is underlined, (iii) all negatively charged residues (D and E) are shown in red, and (iv) the PfMSP4p20 N-terminal sequence and important cysteine residues are highlighted blue.

Figure 27:
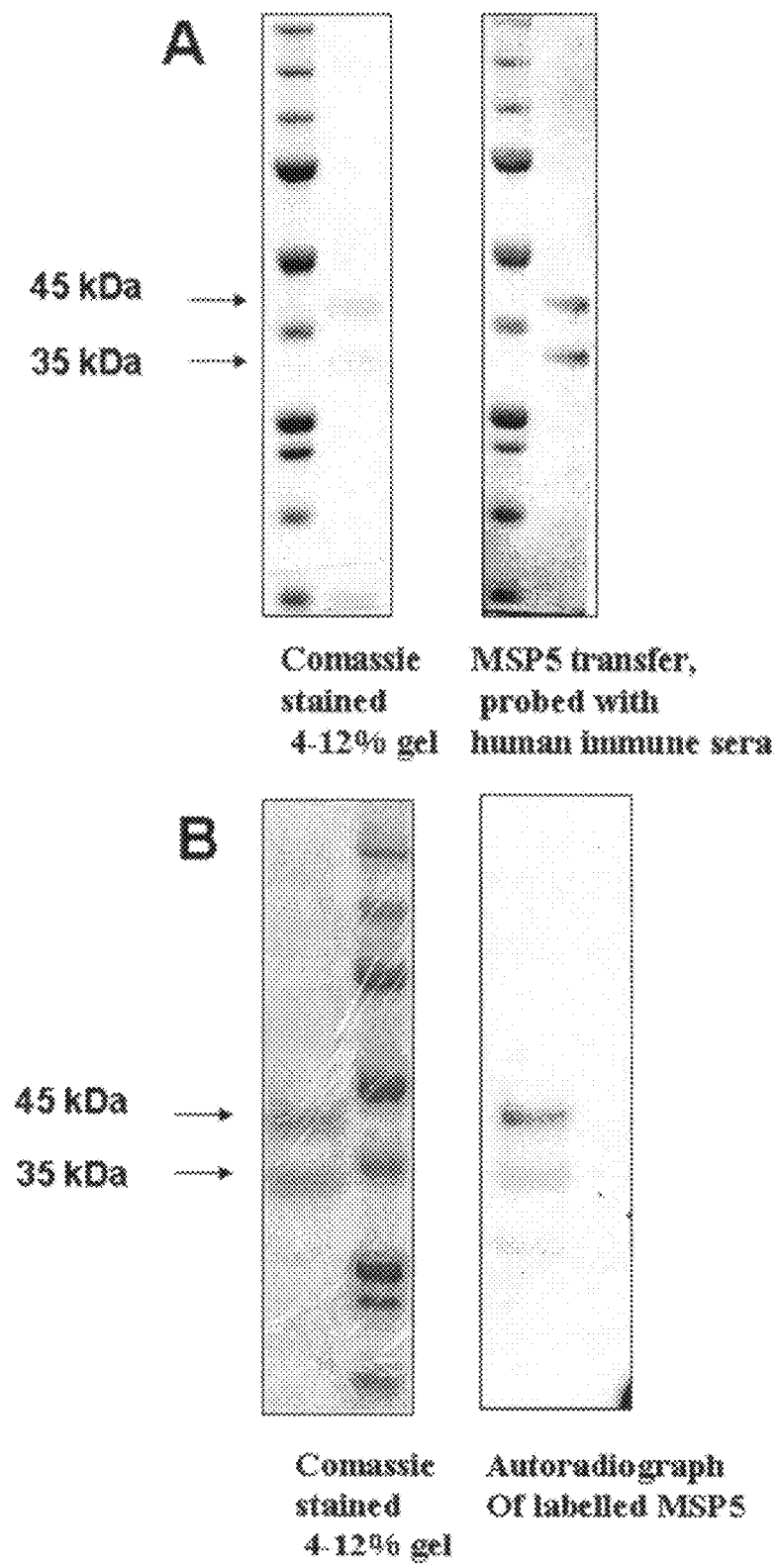

FIG. 27 depicts Baculovirus PfMSP5. (A) Purified recombinant PfMSP5 was migrated on SDS-PAGE gels, transferred to nitrocellulose and probed with human immune sera. (B) PfMSP5 was expressed in the presence of tritiated myristic acid. Purified protein was migrated on SDS-PAGE gels, blue stain and autoradiography performed for 7 weeks.

Figure 28:
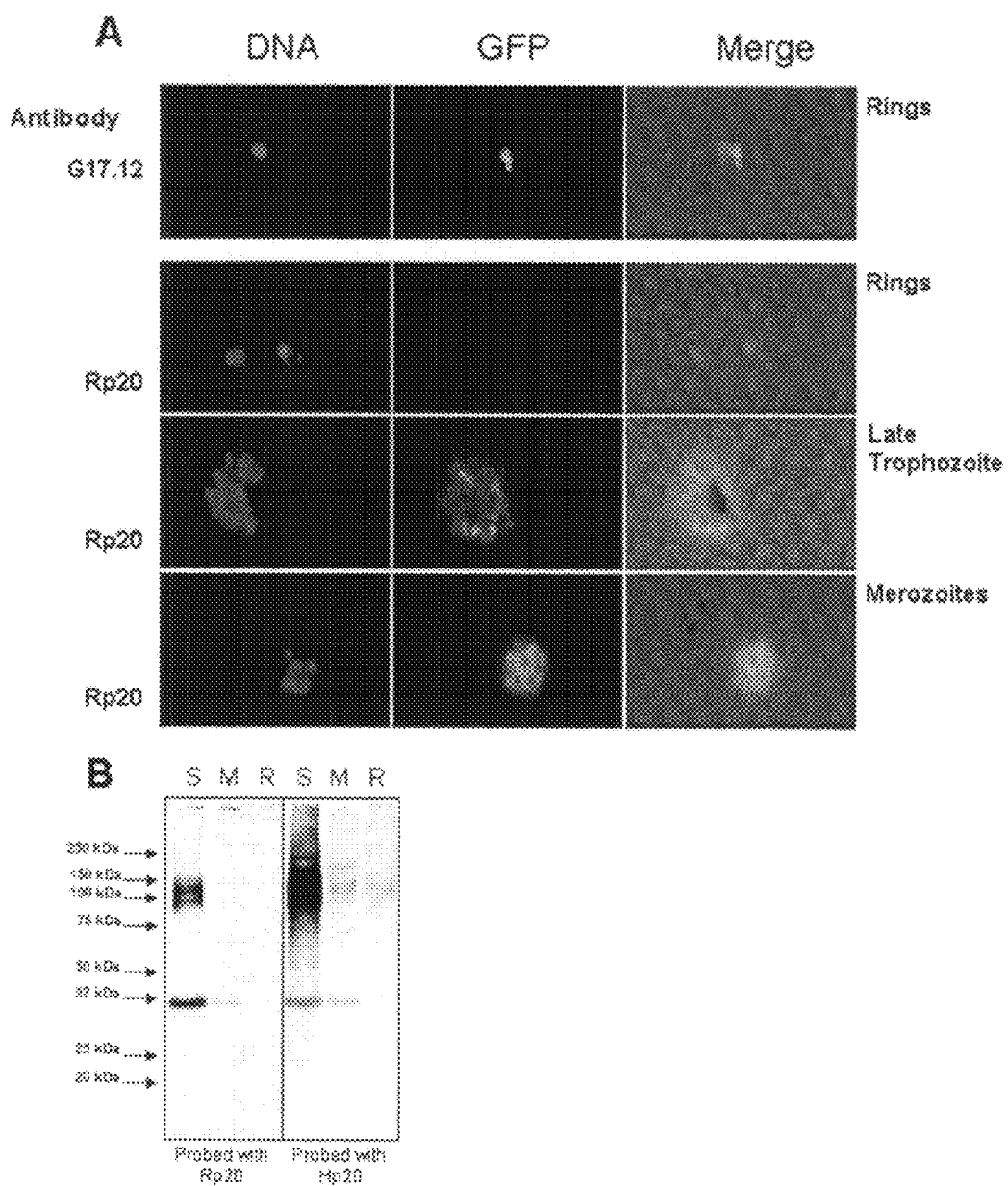

FIG. 28 depicts PfMSP4 expression over time in the RBC stages. (A) Acetone fixed ring stage parasites and air dried late stages and free merozoites were probed with monoclonal antibody G17.12, which is specific for PfMSP1p19 or polyclonal rabbit sera affinity purified against recombinant PfMSP4p20 (Rp20). Antibody staining was revealed with Alexa Fluor® 488 goat anti-mouse or anti-rabbit conjugated antibodies and parasite DNA was stained with Hoechst 33342. (B) Western blot analysis of parasite extract from mature schizonts (S), free merozoites (M), and Rings (R), using affinity purified rabbit (Rp20) and Human sera (1:1 Ndiop and Dielmo pools: Hp20).

FIG. 29 depicts the protein sequence encoded by constructs used for recombinant PfMSP4 expression (SEQ ID NOS 17, 19 and 21, respectively, in order or appearance). Shows the constructs designed to facilitate direct expression of PfMSP4p20. Construct names are listed to the left of the sequence text, the N-terminal sequence of each secreted protein is high-lighted in bold within the text, and the recombinant protein name is listed on the right-hand side.

Figure 30:
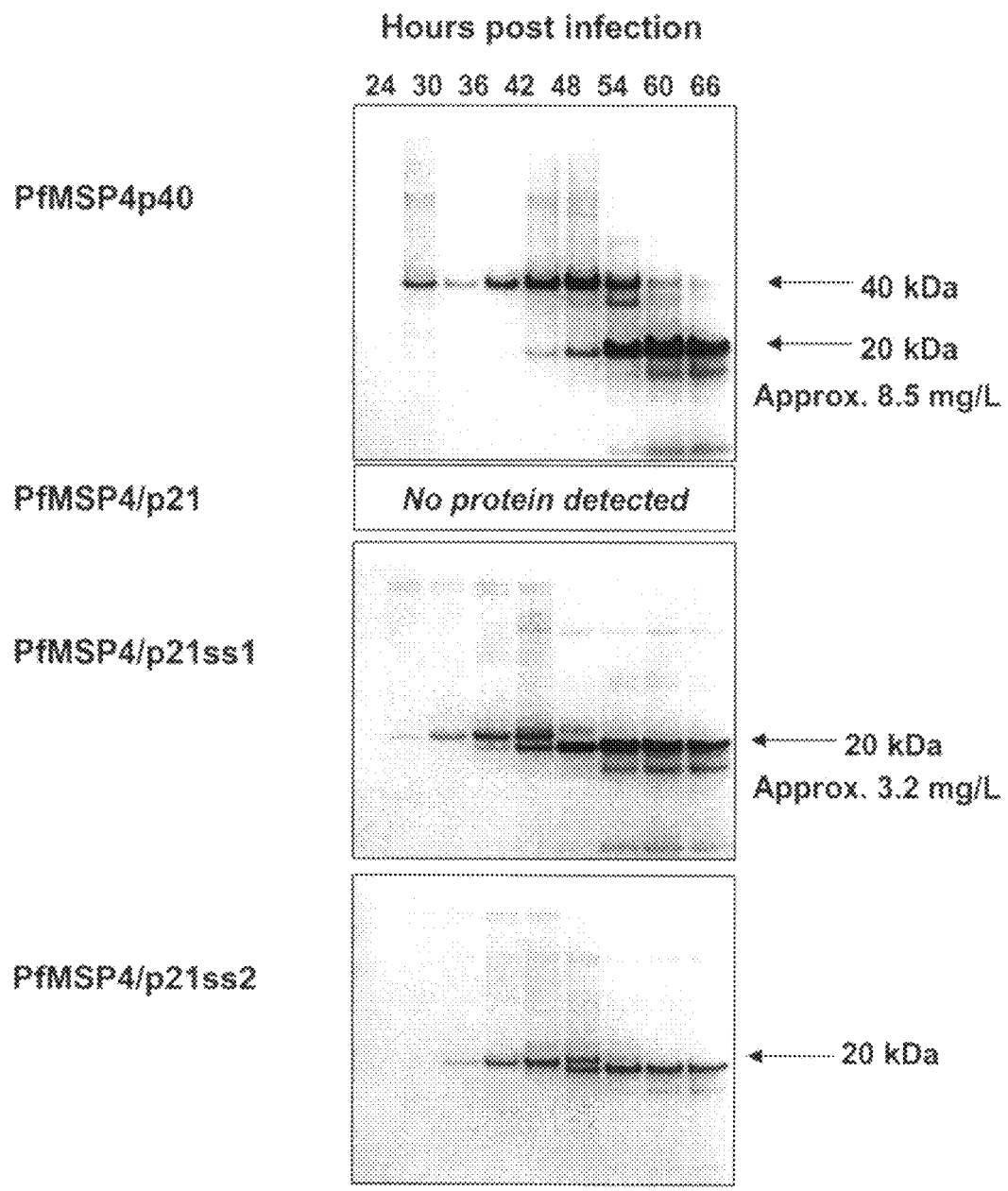

FIG. 30 depicts direct expression of PfMSP4p20 over time. Samples of culture supernatant of PfMSP4p40, PfMSP4p21, PfMSP4p21ss1 or PfMSP4p21ss2 baculovirus infected insect cells were collected at 6 hr intervals between 24 and 66 hr post infection, dialysed, and batch purified over TALON™ resin. Purified protein samples were resolved on NuPAGE™ 4-12% gradient gels, blue stained, and protein size is indicated to the right. Approximate protein yields were calculated using the last 130 mL of culture supernatant remaining at 66 h post infection. Protein was purified by IMAC and HPLC and the protein yield calculated using the BCA protein dosage kit (PIERCE).

FIG. 31 depicts protein sequence alignment of PfMSP4p40 (SEQ ID NO: 12) and PvMSP4/His (SEQ ID NO: 16). Amino acid (single letter code) sequences of Baculovirus *P. vivax* MSP4 and *P. falciparum* MSP4 expression constructs aligned using clustalx. Amino acid identity is denoted (*), conservative substitutions (:), semi-conservative substitutions (.), and radical changes with a blank. The N-terminal sequences identified are underlined and in bold. N-terminal sequences for different protein products are underlined and in bold.

Figure 32:
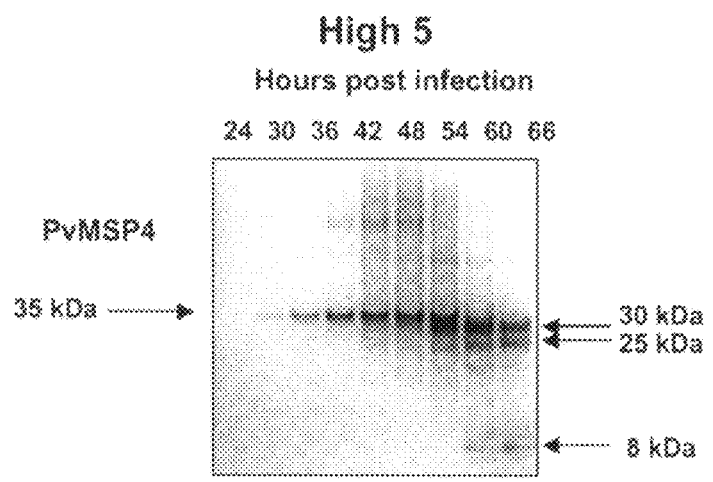

FIG. 32 depicts PvMSP4/His expression over time. In brief, 8 mL samples of spinner culture SN were collected at 6 hr intervals between 24 and 66 hr post infection, dialysed, and batch purified over TALON™ resin. Purified protein samples were resolved on NuPAGE™ 4-12% gradient gels, stained with SimplyBlue SafeStain™ and protein size is indicated to the left and right.

Figure 33:
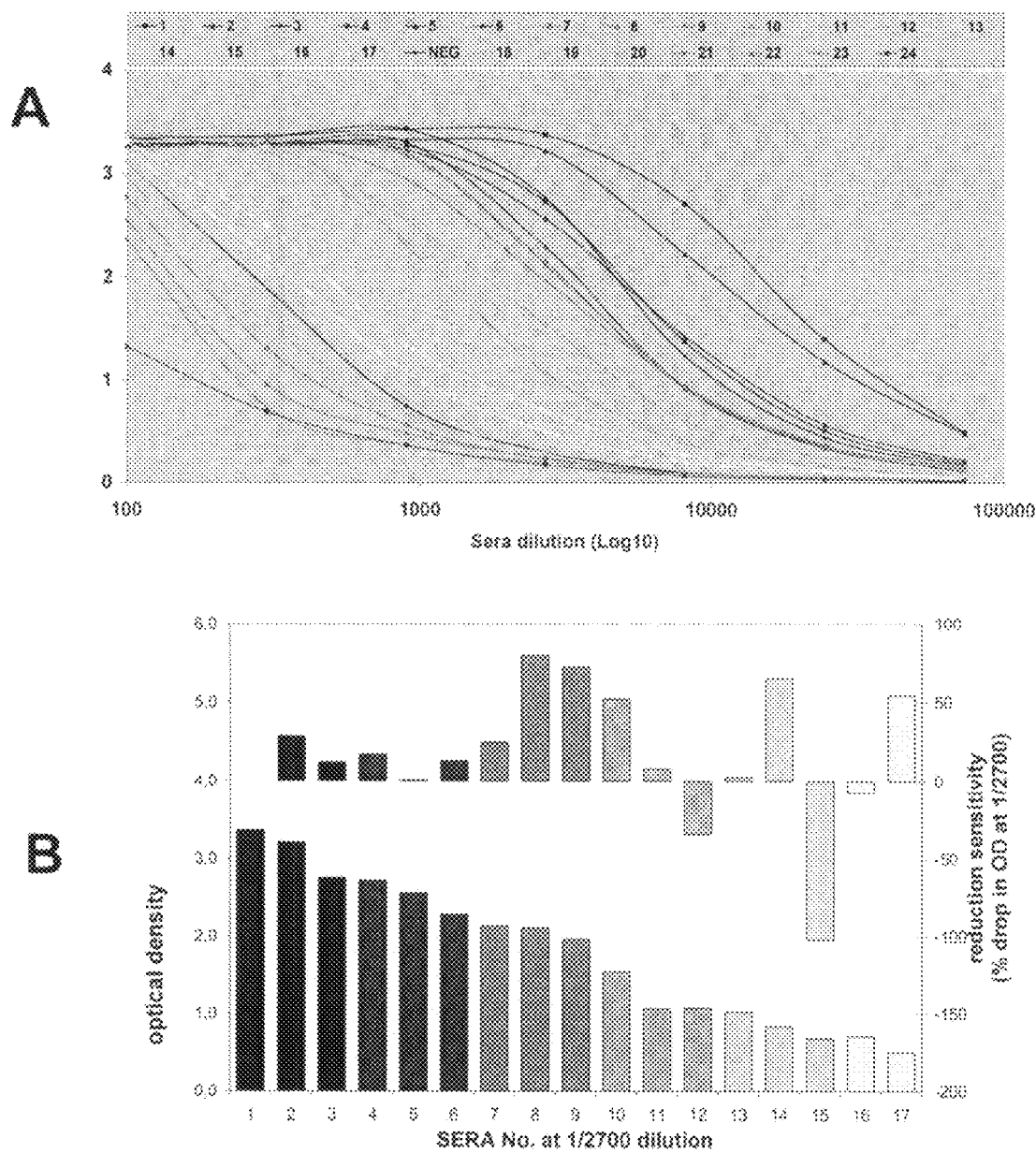

FIG. 33 depicts human immune sera reactivity to PvMSP4/His. (A) ELISA plates were coated with PvMSP4/His expressed in the Baculovirus expression system. Three-fold dilution series or all 24 sera were tested. (B) In parallel, each dilution series was tested against irreversibly reduced PvMSP4. This graph shows the OD at dilution 1/2700 in the lower panel of each sera giving an OD above the negative control against the native antigen. The upper panel shows the reduction in OD seen on antigen reduction at a 1/2700 sera dilution.

Figure 34:
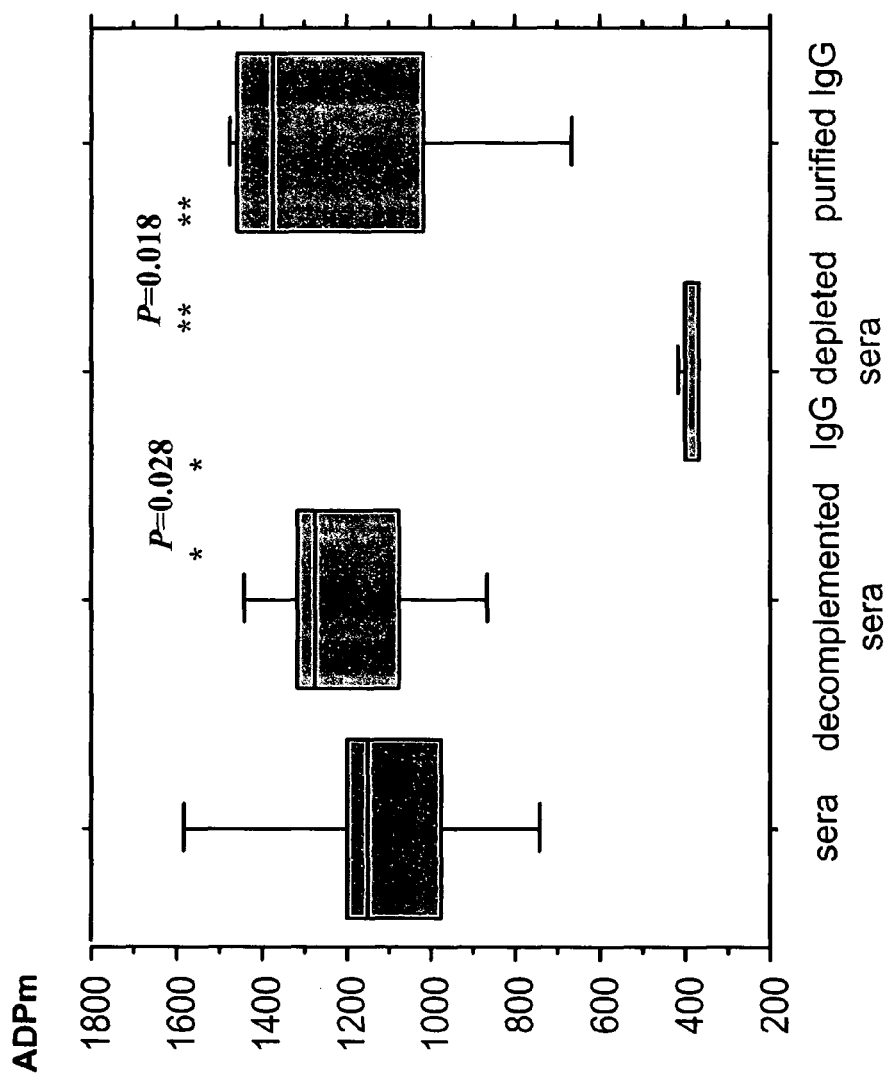
Figure 35:
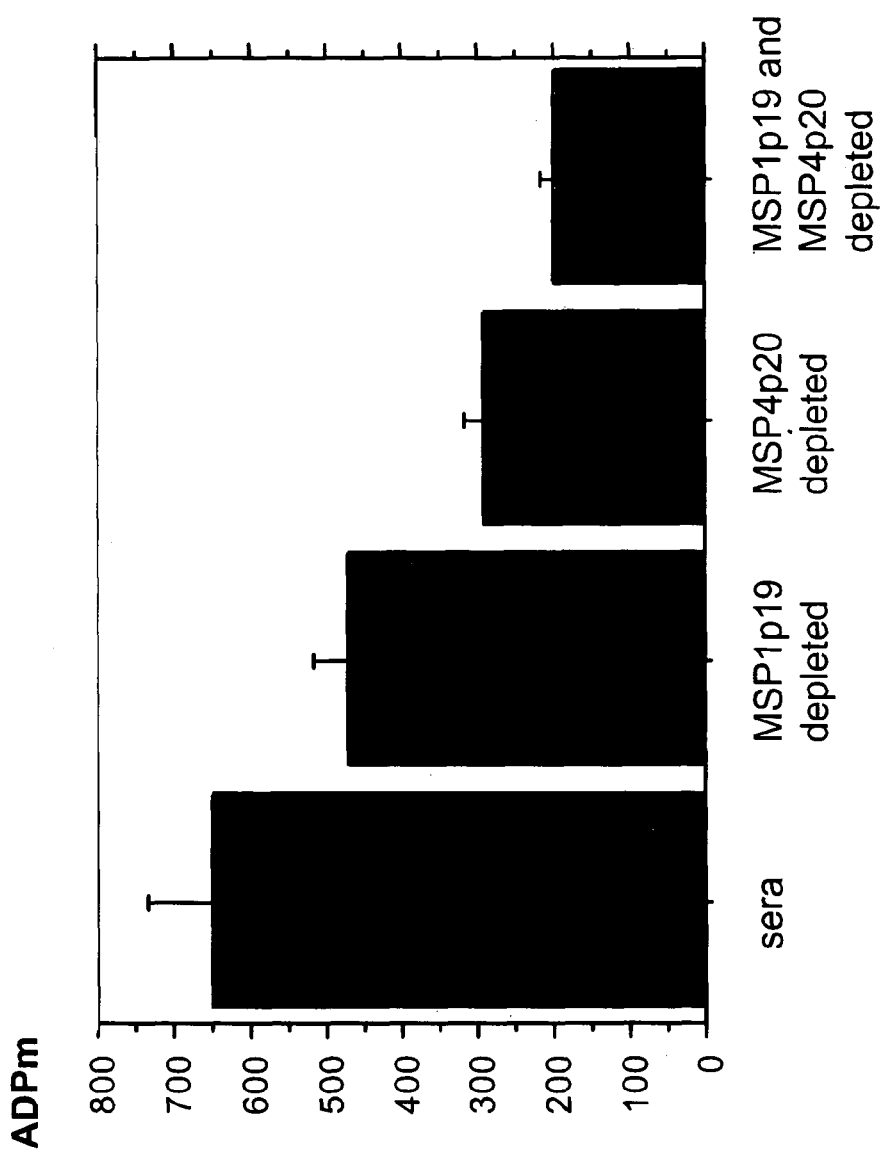

FIGS. 34 and 35 depicts the results of the treatment of sera (decomplemented, IgG depleted, or purified IgG) in a functional assay based on antibody dependent phagocytosis of merozoite (APDm) by PMN. The assay is described in Example 19.

DETAILED DESCRIPTION OF THE INVENTION

Two recently identified merozoite surface antigens, *Plasmodium falciparum* merozoite surface proteins 4 and 5 (PfMSP4 and PfMSP5), are promising protein constituents of a potential multi-component anti-malaria vaccine. The msp4 and msp5 genes both code for 272 residue proteins, each with a single C-terminal EGF-like domain and GPI attachment motif [10,11] and are located in tandem on chromosome 2, just upstream of msp2. Membrane association at the merozoite surface has been demonstrated for both proteins, and human immune sera have been shown to react with recombinant MSP4 expressed in *Escherichia coli* [12,13].

In 3 murine species of *Plasmodium*, *P. yoelii*, *P. chabaudi*, and *P. berghei*, there is only a single gene at the MSP4 and MSP5 locus (MSP4/5), which shows some degree of homology to each [14-16]. This gene is denoted MSP4/5 and has been used to investigate protective immunity in the *P. yoelii* lethal challenge model [17].

MSP4/5 has been shown to confer protection using a variety of immunization strategies, and efficacy is maximized when delivered in conjunction with MSP1p19 [17-20]. In addition, there appears to be no strain specificity in immune responses induced by the murine MSP4/5 protein [21]. In *P. falciparum*, msp4 and msp5 each have a single intron at homologous locations [22].

*Plasmodium falciparum* merozoite surface protein 4 (PfMSP4) protein sequence includes a secretory signal sequence, a C-terminal EGF-like domain, and GPI-attachment signal [10].

The Pfmsp4 gene sequence is 960 bp in length, includes one intron of 144 bp and encodes 272 amino acids residues. The Pfmsp5 gene sequence is 955 bp in length, includes one intron of 136 bp and encodes 272 amino acids residues. As for PfMSP4, the PfMSP5 protein sequence consists of a secretory signal sequence, a C-terminal EGF-like domain, and a GPI-attachment signal [11,22]. Downstream of this cluster of MSP genes is the highly conserved adenylosuccinate lysase (ASL) gene, which has proved to be a useful handle to facilitate the identification of this locus in other species (FIG. 1).

Much current data support the notion that PfMSP4 and PfMSP5 are good vaccine candidates. Nevertheless, several published findings show that recombinant analogs of PfMSP4 produced in two different expression systems (*E. coli* and yeast) differ in antigenicity and induce conformationally-independent responses against the EGF-like domain of the protein, a phenomenon not seen with human immune sera [13]. If recognition of conformational epitopes in this region of the protein is important for protection, as is the case with MSP1-19, it is imperative to generate a product that faithfully reproduces all epitopes.

Accordingly, the invention provides constructs in which the nucleic acids encoding *Plasmodium falciparum* MSP4 and MSP5, and the resulting polypeptides, have been modified to achieve optimal expression in insect cells. More particularly, this invention provides constructs encoding recombinant MSP4 polypeptides, which are expressed as soluble, secreted polypeptides in a baculovirus-insect cell expression system. The recombinant polypeptides contain an EGF-like domain at the C-terminus that appears to be properly folded. This is indicated by a marked reduction (50-60%) in polyclonal rabbit sera recognition of MSP4 when the protein is irreversibly reduced on ELISA plates (see FIG. 12)

One of the recombinant MSP4 polypeptides of the invention is a MSP4 exo-antigen (minus C-terminal hydrophobic residues of the GPI attachment site, thus allowing protein secretion) with a deletion of 30 amino acids from the polymorphic region near the N-terminus. This polypeptide of the invention is referred to as MSP4p30.

Another one of the recombinant MSP4 polypeptides of the invention is a MSP4 exo-antigen (minus C-terminal hydrophobic residues of the GPI attachment site, thus allowing protein secretion) without a deletion of 30 amino acids from a polymorphic region near the N-terminus. This polypeptide of the invention is referred to as MSP4p40 and is the full-length gene product.

Another recombinant MSP4 polypeptide of the invention is a 20 kDa polypeptide corresponding approximately to the C-terminal half of MSP4, starting around the sequence KSPKE (SEQ ID NO: 43) motif and including the EGF domain. Upstream supplementary amino acid residues could be included, in particular residues of the MSP4p40 sequence localized upstream the KSPKE (SEQ ID NO: 43) motif. This recombinant polypeptide of the invention is referred to as MSP4p20.

In addition, this invention provides recombinant MSP5 polypeptides including p35 and p45 forms that are produced simultaneously. Both contain a post-translational modification, likely to involve the covalent attachment of a fatty acid residues (myristoylation) that can boost immunogenicity. These recombinant polypeptides of the invention are referred to as MSP5p45 and MSP5p35.

Nevertheless, the recombinant MSP4 and MSP5 polypeptides of the invention can be also expressed as C-terminal GPI anchored entities using either their native GPI signal sequences or that from another GPI anchored protein sequence signaling for GPI modification. Such GPI modified entities would be expected to substantially enhance immunogenicity of the recombinant MSP4 and MSP5 polypeptides in the absence of any adjuvants of immunity.

The recombinant polypeptides of the invention are described in greater detail with reference to their corresponding SEQ ID NOS. as follows:

Nucleic Acids

| | |
|---|---|
| MSP4p20 | SEQ ID NO: 1 |
| MSP4p30 | SEQ ID NO: 2 |
| MSP4p40 | SEQ ID NO: 3 |
| MSP5 | SEQ ID NO: 4 |
| MSP5p10 | SEQ ID NO: 5 |
| MSP4p21 | SEQ ID NO: 6 |
| MSP4p21 ss1 | SEQ ID NO: 7 and SEQ ID NO: 28 |
| MSP4p21 ss2 | SEQ ID NO: 8 and SEQ ID NO: 29 |

Polypeptides

| | |
|---|---|
| MSP4p20 (breakdown product) | SEQ ID NO: 9 |
| MSP4p30 (ORF present in the construct = polypeptide encoded by the construct) | SEQ ID NO: 10 |
| MSP4p30 (final product of expression = polypeptide produced by insect cells) | SEQ ID NO: 11 |
| MSP4p40 (ORF present in the construct) | SEQ ID NO: 12 |
| MSP4p40 (final product of expression) | SEQ ID NO: 13 |
| MSP5 (ORF present in construct) | SEQ ID NO: 14 |
| MSP5p10 | SEQ ID NO: 15 |
| PvMSP4/His | SEQ ID NO: 16 |
| MSP4p21 (ORF present in the construct) | SEQ ID NO: 17 |
| MSP4p21 (final product of expression) | SEQ ID NO: 18 |
| MSP4p21 ss1 (ORF present in the construct) | SEQ ID NO: 19 |
| MSP4p21 ss1 (final product of expression) | SEQ ID NO: 20 |
| MSP4p21 ss2 (ORF present in the construct) | SEQ ID NO: 21 |
| MSP4p21 ss2 (final product of expression) | SEQ ID NO: 22 |

PvMSP4p20 (sequence of proposed vaccine construct based on *Plasmodium vivax* sequence of MSP4 as given in "alignment of amino acid sequences of PfMSP4 and PvMSP4) SEQ ID NO: 30

These polypeptides are individually and collectively referred to herein as "the recombinant MSP4 and MSP5 polypeptides" of the invention. Similarly, the nucleic acids encoding these polypeptides are referred to as "the recombinant MSP4 and MSP5 nucleic acids" of the invention.

The implications for this invention are widespread. This discovery of the recombinant MSP4 and MSP5 polypeptides enables construction of expression vectors comprising nucleic acid sequences encoding recombinant MSP4 and MSP5 polypeptides of the invention; host cells transfected or transformed with the expression vectors; biologically active recombinant MSP4 and MSP5 polypeptides and recombinant MSP4 and MSP5 polypeptides as isolated or purified proteins; antibodies immunoreactive with recombinant MSP4 and MSP5 polypeptides, diagnostic use of the recombinant MSP4 and MSP5 polypeptides and antibodies directed against the recombinant MSP4 and MSP5 polypeptides in detection of *Plasmodium* parasite and malaria infection and vaccine use of the recombinant MSP4 and MSP5 polypeptides to protect against *Plasmodium* infection.

As used herein, the term "recombinant MSP4 and MSP5 polypeptides" also refers to a genus of polypeptides that further encompasses proteins having the amino acid sequence of SEQ ID NOS: 9-22, as well as those proteins and polypeptides having a high degree of similarity (at least 90% homology) with such amino acid sequences and which proteins and polypeptides are immunoreactive. In addition, recombinant MSP4 and MSP5 polypeptides refers to the gene products of the nucleotides of SEQ ID NOS: 1-8.

The term "purified" as used herein, means that the recombinant MSP4 and MSP5 polypeptides are essentially free of association with other proteins or polypeptides, for example, as a purification product of recombinant host cell culture or as a purified product from a non-recombinant source. The term "substantially purified" as used herein, refers to a mixture that contains recombinant MSP4 and MSP5 polypeptides and is essentially free of association with other proteins or polypeptides, but for the presence of known proteins that can be removed using a specific antibody, and which substantially purified recombinant MSP4 and MSP5 polypeptides can be used as antigens.

A recombinant MSP4 and MSP5 polypeptide "variant" as referred to herein means a polypeptide substantially homologous to recombinant MSP4 and MSP5 polypeptides, but which has an amino acid sequence different from that of recombinant MSP4 and MSP5 polypeptides because of one or more deletions, insertions, or substitutions. The variant amino acid sequence preferably is at least 80% identical to a recombinant MSP4 and MSP5 polypeptide amino acid sequence, most preferably at least 90% identical. The percent identity can be determined, for example by comparing sequence information using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Examples of variants of the MSP4 and MSP5 polypeptides of the invention are proteins that result from alternate mRNA splicing events or from proteolytic cleavage of the recombinant MSP4 and MSP5 polypeptides. Variations attributable to proteolysis include, for example, differences in the termini upon expression in different types of host cells, due to proteolytic removal of one or more terminal amino acids from the recombinant MSP4 and MSP5 polypeptides. Variations attributable to frame shifting include, for example, differences in the termini upon expression in different types of host cells.

As stated above, the invention provides isolated and purified, or homogeneous, recombinant MSP4 and MSP5 polypeptides. Variants and derivatives of recombinant MSP4 and MSP5 polypeptides that can be used as antigens can be obtained by mutations of nucleotide sequences coding for recombinant MSP4 and MSP5 polypeptides. Alterations of the amino acid sequence can be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analogue having the desired amino acid insertion, substitution, or deletion.

Alternatively, oligonucleotide-directed, site-specific mutagenesis procedures can be employed to provide an altered gene wherein predetermined codons can be altered by substitution, deletion, or insertion. Exemplary methods of making the alterations set forth above are disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); Kunkel (Proc. Natl. Acad. Sci. USA 82:488, 1985); Kunkel et al. (Methods in Enzymol. 154:367, 1987); and U.S. Pat. Nos. 4,518,584 and 4,737,462, all of which are incorporated by reference.

Within an aspect of the invention, recombinant MSP4 and MSP5 polypeptides can be utilized to prepare antibodies that specifically bind to recombinant MSP4 and MSP5 polypeptides. The term "antibodies" is meant to include polyclonal antibodies, monoclonal antibodies, fragments thereof, such as F(ab')2 and Fab fragments, as well as any recombinantly produced binding partners. Antibodies are defined to be specifically binding if they bind recombinant MSP4 and MSP5 polypeptides with a Ka of greater than or equal to about $10^7$ $M^{-1}$. Affinities of binding partners or antibodies can be readily determined using conventional techniques, for example, those described by Scatchard et al., Ann. N.Y. Acad. Sci., 51:660 (1949). Polyclonal antibodies can be readily generated from a variety of sources, for example, horses, cows, goats, sheep, dogs, chickens, rabbits, mice, or rats, using procedures that are well known in the art.

The invention further encompasses isolated fragments and oligonucleotides derived from the nucleotide sequences of SEQ ID NOS: 1, 2, 3, 4, 5, 6, 7, and 8. The invention also encompasses polypeptides encoded by these fragments and oligonucleotides.

Nucleic acid sequences within the scope of the invention include isolated DNA and RNA sequences that hybridize to the native recombinant MSP4 and MSP5 nucleic acids disclosed herein under conditions of moderate or severe stringency, and which encode recombinant MSP4 and MSP5 polypeptides. As used herein, conditions of moderate stringency, as known to those having ordinary skill in the art, and as defined by Sambrook et al. Molecular Cloning: A Laboratory Manual, 2 ed. Vol. 1, pp. 1.101-104, Cold Spring Harbor Laboratory Press, (1989), include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of about 60° C., 0.5×SSC, 0.1% SDS. Conditions of high stringency are defined as hybridization conditions as above, and with washing at 68° C., 0.2×SSC, 0.1% SDS. The skilled artisan will recognize that the temperature and wash solution salt concentration can be adjusted as necessary according to factors such as the length of the probe.

Due to the known degeneracy of the genetic code, wherein more than one codon can encode the same amino acid, a DNA sequence can vary from that shown in SEQ ID NOS: 1-8, and still encode a recombinant MSP4 and MSP5 polypeptide having the amino acid sequence of SEQ ID NOS: 9-22. Such variant DNA sequences can result from silent mutations (e.g., occurring during PCR amplification), or can be the product of deliberate mutagenesis of a native sequence.

The invention thus provides equivalent isolated DNA sequences, encoding recombinant MSP4 and MSP5 polypeptides, selected from: (a); (a) DNA comprising the nucleotide sequence of SEQ ID NOS: 1-8 (b) DNA capable of hybridization to a DNA of (a) under conditions of moderate stringency and which encode recombinant MSP4 and MSP5 polypeptides; and (c) DNA which is degenerate as a result of the genetic code to a DNA defined in (a), or (b) and which encodes recombinant MSP4 and MSP5 polypeptides. The polypeptides encoded by such DNA equivalent sequences are encompassed by the invention.

DNA that is equivalent to the DNA sequence of SEQ ID NOS: 1-8 will hybridize under moderately stringent conditions to the DNA sequence that encode polypeptides comprising amino acid sequences of SEQ ID NOS: 9-22. Examples of recombinant MSP4 and MSP5 polypeptides encoded by such DNA, include, but are not limited to, recombinant MSP4 and MSP5 polypeptide fragments and recombinant MSP4 and MSP5 polypeptides comprising inactivated N-glycosylation site(s), inactivated protease processing site(s), or conservative amino acid substitution(s), as described above. The polypeptides encoded by DNA derived from other species of *Plasmodium*, wherein the DNA will hybridize to the complement of the DNA of SEQ ID NOS: 1-8 are also encompassed.

Recombinant expression vectors containing a nucleic acid sequence encoding recombinant MSP4 and MSP5 polypeptides can be prepared using well known methods. The expression vectors include a recombinant MSP4 and MSP5 DNA sequence operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are "operably linked" when the regulatory sequence functionally relates to the recombinant MSP4 and MSP5 DNA sequence. Thus, a promoter nucleotide sequence is operably linked to a recombinant MSP4 and MSP5 DNA sequence if the promoter nucleotide sequence controls the transcription of the recombinant MSP4 and MSP5 DNA sequence. The ability to replicate in the desired host cells, usually conferred by an origin of replication, and a selection gene by which transformants are identified can additionally be incorporated into the expression vector.

In addition, sequences encoding appropriate signal peptides that are not naturally associated with recombinant MSP4 and MSP5 polypeptides can be incorporated into expression vectors. For example, a DNA sequence for a signal peptide (secretory leader) can be fused in-frame to the recombinant MSP4 and MSP5 nucleotide sequences so that the recombinant MSP4 and MSP5 polypeptides are initially translated as a fusion protein comprising the signal peptide. A signal peptide that is functional in the intended host cells enhances extra-cellular secretion of the recombinant MSP4 and MSP5 polypeptides. The signal peptide can be cleaved from the recombinant MSP4 and MSP5 polypeptides upon secretion of recombinant MSP4 and MSP5 polypeptides from the cell.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids. Commercially available vectors include those that are specifically designed for the expression of proteins. These include pMAL-p2 and pMAL-c2 vectors, which are used for the expression of proteins fused to maltose binding protein (New England Biolabs, Beverly, Mass., USA).

Promoter sequences commonly used for recombinant prokaryotic host cell expression vectors include β-lactamase (penicillinase), lactose promoter system (Chang et al., Nature 275:615, 1978; and Goeddel et al., Nature 281:544, 1979), tryptophan (trp) promoter system (Goeddel et al., Nucl. Acids Res. 8:4057, 1980; and EP-A-36776), and tac promoter (Maniatis, Molecular Cloning: A Laboratory Manual, Cold Spring Harbor Laboratory, p. 412, 1982).

Suitable host cells for expression of recombinant MSP4 and MSP5 polypeptides include prokaryotes, yeast or higher eukaryotic cells. Insect cells are preferred. Appropriate cloning and expression vectors for use with bacterial, fungal, yeast, and mammalian cellular hosts are described, for example, in Pouwels et al. Cloning Vectors: A Laboratory Manual, Elsevier, N.Y., (1985). Cell-free translation systems could also be employed to produce recombinant MSP4 and MSP5 polypeptides using RNAs derived from DNA constructs disclosed herein.

It will be understood that the present invention is intended to encompass the previously described proteins or polypeptides in isolated or purified form, whether obtained using the techniques described herein or other methods. In a preferred embodiment of this invention, the recombinant MSP4 and MSP5 polypeptides are substantially free of human tissue and human tissue components, nucleic acids, extraneous proteins and lipids, and adventitious micro-organisms, such as bacteria and viruses. It will also be understood that the invention encompasses equivalent proteins having substantially the same biological and immunogenic properties.

Depending on the use to be made of the recombinant MSP4 and MSP5 polypeptides of the invention, it may be desirable to label them. Examples of suitable labels are radioactive labels, enzymatic labels, fluorescent labels, chemiluminescent labels, and chromophores. The methods for labelling proteins of the invention do not differ in essence from those widely used for labelling immunoglobulin. The need to label may be avoided by using labelled antibody to the antigen of the invention or anti-immunoglobulin to the antibodies to the antigen as an indirect marker.

Once the recombinant MSP4 and MSP5 polypeptides of the invention have been obtained, they have been used to produce polyclonal and monoclonal antibodies reactive therewith. Thus, a protein or polypeptide of the invention can be used to immunize an animal host by techniques known in the art. Such techniques usually involve inoculation, but they may involve other modes of administration. A sufficient amount of the polypeptide is administered to create an immunogenic response in the animal host. Any host that produces antibodies to the antigen of the invention can be used. Once the animal has been immunized and sufficient time has passed for it to begin producing antibodies to the antigen, polyclonal antibodies can be recovered. The general method comprises removing blood from the animal and separating the serum from the blood. The serum, which contains antibodies to the antigen, can be used as an antiserum to the antigen. Alternatively, the antibodies can be recovered from the serum. Affinity purification is a preferred technique for recovering purified polyclonal antibodies to the antigen from the serum.

Monoclonal antibodies to the antigens of the invention can also be prepared. One method for producing monoclonal antibodies reactive with the antigens comprises the steps of immunizing a host with the antigen; recovering antibody producing cells from the spleen of the host; fusing the antibody producing cells with myeloma cells deficient in the enzyme hypoxanthine-guanine phosphoribosyl transferase to form hybridomas; selecting at least one of the hybridomas by growth in a medium comprising hypoxanthine, aminopterin, and thymidine; identifying at least one of the hybridomas that produces an antibody to the antigen; culturing the identified hybridoma to produce antibody in a recoverable quantity; and recovering the antibodies produced by the cultured hybridoma.

These polyclonal or monoclonal antibodies can be used in a variety of applications. Among these is the neutralization of corresponding proteins. They can also be used to detect *Plasmodium* parasite antigens in biological preparations or in purifying corresponding proteins, glycoproteins, or mixtures thereof, for example, when used in an affinity chromatographic column.

The recombinant MSP4 and MSP5 polypeptides can be used as antigens to detect the presence of antibodies specific for malaria parasite in biological samples and to evaluate the levels of such antibodies in those biological samples, which constitute a signal for current or previous infection. Such biological samples of course include human tissue and human cells, as well as biological fluids, such as human body fluids, including human sera. When used as a reagent in an immunoassay for determining the presence or concentration of the antibodies to malaria, the antigens of the present invention provide an assay that is convenient, rapid, sensitive, and specific.

More particularly, the antigens of the invention can be employed for the detection of malaria by means of immunoassays that are well known for use in detecting or quantifying humoral components in fluids. Thus, antigen-antibody interactions can be directly observed or determined by secondary reactions, such as precipitation or agglutination. In addition, immunoelectrophoresis techniques can also be employed. For example, the classic combination of electrophoresis in agar followed by reaction with anti-serum can be utilized, as well as two-dimensional electrophoresis, rocket electrophoresis, and immunolabeling of polyacrylamide gel patterns (Western Blot or immunoblotting). Other immunoassays in which the antigens of the present invention can be employed include, but are not limited to, radioimmunoassay, competitive immunoprecipitation assay, enzyme immunoassay, and immunofluorescence assay. It will be understood that turbidimetric, colorimetric, and nephelometric techniques can also be employed. An immunoassay based on Western Blot technique is preferred.

Immunoassays can be carried out by immobilizing one of the immunoreagents, either an antigen of the invention or an antibody of the invention to the antigen, on a carrier surface while retaining immunoreactivity of the reagent. The reciprocal immunoreagent can be unlabeled or labelled in such a manner that immunoreactivity is also retained. These techniques are especially suitable for use in enzyme immunoassays, such as enzyme linked immunosorbent assay (ELISA) and competitive inhibition enzyme immunoassay (CIEIA).

When either the antigen of the invention or antibody to the antigen is attached to a solid support, the support is usually a glass or plastic material. Plastic materials moulded in the form of plates, tubes, beads, or disks are preferred. Examples of suitable plastic materials are polystyrene and polyvinyl chloride. If the immunoreagent does not readily bind to the solid support, a carrier material can be interposed between the reagent and the support. Examples of suitable carrier materials are proteins, such as bovine serum albumin, or chemical reagents, such as gluteraldehyde or urea. Coating of the solid phase can be carried out using conventional techniques.

The invention provides immunogenic recombinant MSP4 and MSP5 polypeptides, and more particularly, protective polypeptides for use in the preparation of vaccine compositions against malaria. These polypeptides can thus be employed as vaccines by administering the polypeptides to a mammal susceptible to malaria infection. Conventional modes of administration can be employed. For example, administration can be carried out by oral, sublingual, respiratory, or parenteral routes. Intradermal, subcutaneous, intramuscular, and intravenous routes of administration are preferred when the vaccine is administered parenterally.

The major purpose of the immune response in a malaria-infected mammal is to inactivate the malaria parasites and to facilitate malaria parasite killing and clearance of parasite infected red blood cells. The B-cell arm of the immune response has the major responsibility for inactivating blood-stage malaria parasites. The principal manner in which this is achieved is by neutralization of infectivity (inhibition of erythrocyte invasion) and antibody dependent cellular cytotoxicity (ADCC). The target antigen must be conserved to be effective against re-infection with other parasite strains, and capable of inducing T helper cell activity (CD4+) to generate a long-lived memory response. T cell mediated mechanism for destruction of parasite infected cells is provided by cytotoxic (CD8+) T lymphocytes (CTL) that could recognize recombinant MSP4 and MSP5 antigens expressed in combination with Class I histocompatibility antigens at the surface of hepatic cells in the preerythrocytic phase of infection.

Following is a vaccine, which includes (A) the natural signal sequence (B) a C-terminal His tag and (C) the acid repeat region that resembles that of the *P. falciparum* antigen most strongly correlated with protective antibody responses in the field (MSP4p20).

[SEQ ID NO: 30]

```
MKVAYFLSVLDLLIIFSLYFDGRRSAFAGIAACIRHGRILGEGGE/QNST

PGSGGQTGDHSAEAENGDYNEQGDDHGDDHGDDHGDDHGDEQDGEDYDDA

EDDDLYELSEVDENANLCLDNNGGCGDDKICENLGKGIVKCLCKPGYKLV

GTECVEHHHHHH
```

The ability of the recombinant MSP4 and MSP5 polypeptides and vaccines of the invention to induce protective levels of neutralizing antibody (i.e., antibodies elicited during a humoral response to the antigen, which directly blocks the ability of the pathogen to infect red blood cells) in a host can be enhanced by emulsification with an adjuvant (immunostimulator), incorporating in a liposome, coupling to a suitable carrier, or by combinations of these techniques. For example, the recombinant MSP4 and MSP5 polypeptides of the invention can be administered with a conventional adjuvant, such as aluminium phosphate and aluminium hydroxide gel, in an amount sufficient to potentiate humoral or cell-mediated immune responses in the host.

The immunization schedule will depend upon several factors, such as the susceptibility of the host to infection and the age of the host. A single dose of the vaccine of the invention can be administered to the host or a primary course of immunization can be followed in which several doses at intervals of time are administered. Subsequent doses used as boosters can be administered as needed following the primary course.

The recombinant MSP4 and MSP5 proteins, polypeptides, and vaccines of the invention can be administered to the host in an amount sufficient to induce immune responses that prevent or inhibit parasite infection and replication in vivo so as to reduce the parasite burden in the host and diminish clinical symptoms. An immunogenic response can be obtained by administering the polypeptides of the invention to the host in amounts ranging from 10 to 500 micrograms per dose, preferably about 50 to 100 micrograms per dose. The proteins and vaccines of the invention can be administered together with a physiologically acceptable carrier. For example, a diluent, such as water or a saline solution, can be employed.

Another aspect of the invention provides a method of DNA vaccination. The method also includes administering any combination of the nucleic acids encoding recombinant MSP4 and MSP5 polypeptides, the proteins and polypeptides per se, with or without carrier molecules, to an individual. In embodiments, the individual is an animal, and is preferably a mammal. More preferably, the mammal is selected from the group consisting of a human, a dog, a cat, a bovine, a pig, and a horse. In an especially preferred embodiment, the mammal is a human.

Those of skill in the art are cognizant of the concept, application, and effectiveness of nucleic acid vaccines (e.g., DNA vaccines) and nucleic acid vaccine technology as well as protein and polypeptide based technologies. The nucleic acid based technology allows the administration of nucleic acids encoding recombinant MSP4 and MSP5 polypeptides, naked or encapsulated, directly to tissues and cells without the need for production of encoded proteins prior to administration. The technology is based on the ability of these nucleic acids to be taken up by cells of the recipient organism and expressed to produce an immunogenic determinant to which the recipient's immune system responds. Typically, the expressed antigens are displayed on the surface of cells that have taken up and expressed the nucleic acids, but expression and export of the encoded antigens into the circulatory system of the recipient individual is also within the scope of the present invention. Such nucleic acid vaccine technology includes, but is not limited to, delivery of naked DNA and RNA and delivery of expression vectors encoding recombinant MSP4 and MSP5 polypeptides. Although the technology is termed "vaccine", it is equally applicable to immunogenic compositions that do not result in a protective response. Such non-protection inducing compositions and methods are encompassed within the present invention.

Although it is within the present invention to deliver nucleic acids encoding recombinant MSP4 and MSP5 polypeptides and carrier molecules as naked nucleic acid, the present invention also encompasses delivery of nucleic acids as part of larger or more complex compositions. Included among these delivery systems are viruses, virus-like particles, or bacteria containing the nucleic acid encoding recombinant MSP4 and MSP5 polypeptides. Also, complexes of the invention's nucleic acids and carrier molecules with cell permeabilizing compounds, such as liposomes, are included within the scope of the invention. Other compounds, such as molecular vectors (EP 696,191, Samain et al.) and delivery systems for nucleic acid vaccines are known to the skilled artisan and exemplified in, for example, WO 93 06223 and WO 90 11092, U.S. Pat. No. 5,580,859, and U.S. Pat. No. 5,589,466 (Vical's patents), which are incorporated by reference herein, and can be made and used without undue or excessive experimentation.

This invention will be described in greater detail in the following specific embodiments.

It has been known for a long time that antigens generated using the baculovirus expression system faithfully contain complex structures involving the formation of cysteine bonds and are suitable for crystallization studies. These antigens are commonly held as "the gold standard" against which antigens produced in other systems are checked [24,25]. As both PfMSP4 and PfMSP5 contain EGF-like domains that are formed by disulphide bonds, they may benefit from being generated in the baculovirus-system. However, as with all commonly used expression systems, protein yield is detrimentally affected by the unusual codon usage of *P. falciparum* [26,27]. In addition, these highly A+T rich sequences are frequently mutated in *E. coli* [28] and rarely contain unique restriction enzyme sites. For these reasons, synthetic genes were designed and constructed using the method described by Withers-Martinez (1999) [29].

Designing a Synthetic Gene

Based on the sequence data available from GenBank at the time, and with future applications in mind, including the human challenge model, the common amino acid sequences, PfMSP4 NF54 sequence (Ac No. AF295318) and PfMSP5 3D7 sequence (Ac No. AF106476), were selected for modification. In parallel, to enrich sequence data sets and perform inter and intra-population analysis and inter-species analysis, a polymorphism study was conducted using samples taken from locations of varying endemicity as follows.

A Summary of msp4 and msp5 Gene Polymorphism

Antigen polymorphism is an important consideration when developing a vaccine for *P. falciparum*. The most promising blood stage vaccine candidates examined so far are merozoite surface protein 1, (MSP1) and an apical membrane antigen (AMA1 [1-3]. However, these and other surface antigen genes display a disproportionately high frequency of non-synonymous single nucleotide polymorphisms (nsSNPs) when compared to genes coding for antigens that are not accessible to immune effector-mechanisms [4-6]. As a compounding factor, these nsSNPs frequently lead to radical amino acid substitutions that are predominantly clustered within the regions of the peptide most accessible to the host immune system [7]. The resulting amino acid substitutions are believed to function in immune evasion by altering important B and T cell epitopes [34,38]. Thus, vaccination with integral recombinant versions of such antigens is likely to result in strain specific protection [4,8]. It is widely believed that a globally effective vaccine will include the conserved portions of several surface proteins derived from multi-stage targets [30].

To date, only a limited amount of polymorphism data is available for PfMSP4 and PfMSP5 [11,31,32]. To fully explore polymorphism of both PfMSP4 and PfMSP5 from highly endemic locations a sequence analysis study was conducted, the results of which are presented in Poison et al. 2005 [33]. In summary, the Pfmsp5 gene sequence was found to be highly conserved and potentially under purifying selection. The Pfmsp4 gene sequence was found to be relatively conserved for a *P. falciparum* surface antigen [5] and to contain an N-terminal cluster of polymorphic sites (residues 45-81), which includes two sites that are potentially under balancing selection (N52 and G74). This would explain the observed clustering of apparently neutral (or hitchhiking) polymorphisms within the flanking sequences and could be linked to either B or T-cell epitope variation. Balancing selection classically arises from the existence of two allelic gene sequences that harbour a "difference" which has an impact on immune recognition of the molecule. When allele A is most common in the population, it is an advantage to be allele B, as this allele will not be recognised by the immune system as well as the dominant allele. Thus, allele B becomes more common until it is the most frequent type, the immune system will become competent for the B allele, at which point it is an advantage to be allele A. First, the presence of balancing selection suggests that the MSP4 protein is the target of an effective immune mechanism. Second, this suggests that to protect people in the field you would need to vaccinate with both alleles, or exclude this region of the protein, forcing the immune system to act against conserved regions. With regard to the recent identification of two PfMSP4 derived peptides capable of specifically binding hepatocytes [34], the first (which represents residues 76-92 of MSP4p40) harbours one semi-conservative polymorphism (A81), and the second (which represents residues 113-135 of MSP4p40) contains one deletion (115-119) and/or one semi-conservative polymorphism (G119). In the existing PfMSP4 data sets, differences within these sequences are present at relatively low frequencies, supporting the idea that these are functionally important sites (Note; these sequences are also represented by SALSA, FIG. 2). Finally, there is one more site potentially under balancing selection, V190, which lies 17 residues upstream of the first cysteine of the EGF-like domain, once again this could be involved in either B or T-cell epitope modifications.

Construction of a Synthetic Gene; PfMSP4

First, to facilitate protein secretion, all sequence starting three residues downstream of the EGF domain was removed. This included the GPI attachment signal, as it is known that the baculovirus system can use such sequences to incorporate insect cell GPI-moieties and results in cell surface localisation of the protein (Bonnet et al. 2005 publication submitted to Vaccine). In addition, the natural signal MSP4 sequence was retained since the baculovirus expression system is known to correctly cleave the native MSP1 signal sequence in recombinant analogs, although the native cleaved N-terminus of MSP4 has not been defined. To prevent N-glycosylation, which is not known to occur in *Plasmodium* but does occur in baculovirus at two potential sites in the PfMSP4 sequence, the serine residues $S_{65}$ and $S_{73}$ substituted for alanine. Both residues have small side chains (Ser=HO—$CH_2$—, Ala=$CH_3$—) and although these sites have not been reported to be naturally polymorphic, these changes are believed to have a minimal effect on the local or macro structure of the protein. Once the remaining features had been added, including a C-terminal hexa-his-tag (SEQ ID NO: 57 and stop codon, the sequence was back translated using the CODOP program set to *Trichoplusia ni* (High Five) cell codon usage (Table 1).

MSP4 Codon Usage of NF54 and Synthetic Gene

| Codon | aa | p.f | H5 |
|---|---|---|---|
| GCA | Ala | 2 | 4 |
| GCC | | 0 | 1 |
| GCG | | 1 | 0 |
| GCT | | 3 | 3 |
| total | | 6 | 8 |
| AGA | Arg | 4 | 0 |
| AGG | | 0 | 1 |
| CGA | | 0 | 0 |
| CGC | | 0 | 1 |
| CGG | | 0 | 0 |
| CGT | | 0 | 2 |
| total | | 4 | 4 |
| AAC | Asn | 2 | 17 |
| AAT | | 15 | 0 |
| total | | 17 | 17 |
| GAC | Asp | 7 | 22 |
| GAT | | 18 | 3 |
| total | | 25 | 25 |
| TGC | Cyc | 0 | 4 |
| TGT | | 7 | 3 |
| total | | 7 | 7 |
| CAA | Gln | 5 | 3 |
| CAG | | 0 | 2 |
| total | | 5 | 5 |
| GAA | Glu | 36 | 25 |
| GAG | | 4 | 15 |
| total | | 40 | 40 |
| GGA | Gly | 11 | 13 |
| GGC | | 1 | 2 |
| GGG | | 3 | 0 |
| GGT | | 4 | 4 |
| total | | 19 | 19 |
| CAC | His | 1 | 12 |
| CAT | | 6 | 1 |
| total | | 7 | 13 |
| ATA | Ile | 5 | 1 |
| ATC | | 2 | 5 |
| ATT | | 3 | 4 |
| total | | 10 | 10 |
| CTA | Leu | 2 | 1 |
| CTC | | 0 | 2 |
| CTG | | 0 | 0 |
| CTT | | 0 | 3 |
| TTA | | 6 | 0 |
| TTG | | 2 | 4 |
| total | | 10 | 10 |
| ATG | Met | 4 | 4 |
| total | | 4 | 4 |
| AAA | Lys | 24 | 5 |
| AAG | | 7 | 26 |
| total | | 31 | 31 |
| TTC | Phe | 0 | 4 |
| TTT | | 4 | 0 |
| total | | 4 | 4 |
| CCA | Pro | 4 | 2 |
| CCC | | 1 | 1 |
| CCG | | 0 | 0 |
| CCT | | 2 | 4 |
| total | | 7 | 7 |
| AGC | Ser | 1 | 3 |
| AGT | | 6 | 4 |
| TCA | | 4 | 1 |
| TCC | | 3 | 1 |
| TCG | | 0 | 1 |
| TCT | | 5 | 7 |
| total | | 19 | 17 |
| TAA | stop | 0 | 1 |
| TAG | | 0 | 0 |
| TGA | | 0 | 0 |
| total | | 0 | 1 |

-continued

| Codon | aa | p.f | H5 |
|---|---|---|---|
| ACA | Thr | 1 | 3 |
| ACC |  | 1 | 3 |
| ACG |  | 0 | 0 |
| ACT |  | 5 | 1 |
| total |  | 7 | 7 |
| TGG | Trp | 1 | 1 |
| total |  | 1 | 1 |
| TAC | Tyr | 0 | 6 |
| TAT |  | 6 | 0 |
| total |  | 6 | 6 |
| GTA | Val | 5 | 3 |
| GTC |  | 0 | 5 |
| GTG |  | 1 | 3 |
| GTT |  | 10 | 5 |
| total |  | 16 | 16 |
|  | p.f. |  |  |
|  |  |  | H5 |
| Codons | 245 |  |  |
|  |  |  | 252 |
| % GC | 30.6 |  | 47.5 |

CODOP is a Unix perl script which implements codon optimization as proposed by Hale and Thompson [35] and is described in detail elsewhere [29]. The re-codoned nucleotide sequence was subsequently optimised by manual intervention to give rise to 38×40 mers with a Tm of 60-65° C. and to contain several unique restriction sites to facilitate sub-cloning (FIG. 3).

The overall GC content of the gene was increased by 15%, vastly increasing the ease and efficiency of sub-cloning and reducing the frequency of replication errors made by E. coli during construct manipulation. The 38 overlapping oligonucleotides, each 40 bases in length, were obtained from Eurogentec (with only standard purification). Gene assembly and amplification were achieved as previously described [29].

Figure 4:
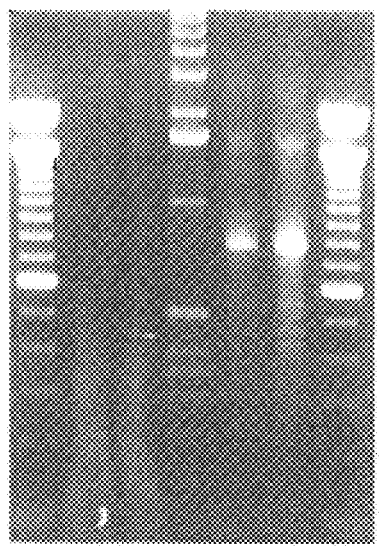

In brief, gene oligonucleotides were mixed in equi-molar quantities (25 µM each), and diluted 10-fold in to a 50 µL PCR reaction containing 1 µL of pfu DNA polymerase (Stratagene), 5 µL of 10× product buffer, 200 µM dNTPs and 2 µL of 25 mM MgSO$_4$. The PCR program consisted of one denaturation step of 94° C. for 1 min, followed by 25 cycles of 94° C. for 30 s, 52° C. for 30 s and 72° C. for 2 min. To amplify the full-length gene product, 5 µL of the gene assembly reaction were diluted 10-fold into a 50 µL PCR reaction containing 1 µL of pfu DNA polymerase (Stratagene), 5 µL of 10× product buffer, 200 µM dNTPs, 2 µL of 25 mM MgSO$_4$ and the outer gene assembly oligonucleotide numbers 1 and 20 at 500 nM each. The PCR program consisted of one cycle of 94° C. for 1 min, 25 cycles of 94° C. for 45 s, 68° C. for 45 s and 72° C. for 2 min and a final elongation step of 72° C. for 10 min. The dominant and correctly sized fragment, shown in FIG. 4, was gel extracted, cloned into pMOSBlue for sequencing and finally transferred into the vector pVL1393 for integration into the Baculoviral genome (Baculogold, PharMingen). This expression construct is called MSP4p40/His.

Modified PfMSP4 Constructs

Two additional MSP4 constructs were also assembled, named MSP4-EGF/His and MSP4p30/His (FIG. 5). The construct MSP4-EFG/His was designed to express the MSP4 EGF-like domain only, mainly for the purpose of crystallisation studies. A PCR fragment containing the predicted signal sequence as described by PlasmoDB (residues 1-20) and 2 downstream residues was generated by high fidelity PCR. Reactions contained gene assembly oligonucleotide 1 and reverse primer MSP4modI (5'-TAT-AGC-AGA-TCT-TTG-TCG-AAG-TTG-ATG-GTG-CA-3') [SEQ ID NO: 23] which contains a Bgl II restriction site. The synthetic gene clone pMosMSP4 was used as a template. The resultant 86 bp PCR product was cleaved with restriction enzymes Bam HI and Bgl II and gel extracted. The product was then ligated (T4 DNA ligase; NEB) into previously prepared pMosMSP4 vector, also digested with Bam HI and Bgl II to remove all sequence upstream of the EGF-like domain, leaving residues D205 to H252.

The MSP4p30/His construct was designed to remove 30 residues from the C-terminal of MSP4 (residue 45 to 74) where the majority of the reported polymorphisms reside (Highlighted in FIG. 5). A PCR fragment encoding residues 1 to 44 was generated using gene assembly oligonucleotide 1, reverse primer MSP4modII (5'-ATA TGG CTG CAG CCA AGA TCC TCA TGT TAA GCA T-3') [SEQ ID NO: 24] and pMosMSP4 vector as a template. The fragment was 154 bp in size and had restriction sites Bam HI and Pst I at the extreme 3' and 5' ends respectively. A fragment of DNA encoding all sequence down stream of residue A75 was cut from vector pMosMSP4 using restriction enzymes Pst I and Spe I (which lies downstream of the MSP4 ORF, within the pMOSBlue vector sequence). The two DNA fragments were combined in equi-molar quantities in a T4 DNA ligase (NEB) reaction and incubated at 4° C. over 3 days. Resolution of 2 µL of the ligase reaction in a 1% agarose gel stained with ethidium bromide revealed the presence of several products, including the required product, 724 bp in length. This product was amplified by high fidelity PCR using gene assembly oligonucleotide 1 and 20 and 1 µL of the ligation reaction as a template, gel extracted and cloned back into pMOSBlue. As with the synthetic gene, the MSP4-EGF/His and MSP4p30/His gene sequences were confirmed before being cloned into the expression vector pVL1393.

A further expression construct was designed and constructed from the synthetic MSP4 gene described above. This expression cassette was designed to allow expression of the non-polymorphic, protease resistant and structurally intact C-terminal region of the protein (called p20 and described in later sections). This construct includes all nucleotide sequence downstream of the xba I cloning site of MSP4p40/His, and thus encodes all residues downstream of Leu$_{130}$ (non-included). To facilitate protein secretion, a PCR fragment encoding the MSP4 signal sequence plus 9 downstream residues (Met$_1$-Pro$_{49}$) was generated using gene assembly oligo 1 and the reverse primer MSP4p21 rev (ATT AAT CTA GAG GCT TTT CTT CAC CCA AGA TCC TCA TG) SEQ ID NO: 25 and ligated into Bam HI/Xba I double digested pMosMSP4p40/His. This construct was named MSP4p21/His and the sequence was confirmed before being ligated into pVL1319 for integration into the Baculovirus genome. Two supplementary similar expression constructs were further designed and constructed from the synthetic MSP4 gene described above. These constructs were named MSP4p21 ss1 and MSP4p21 ss2 and both encode all residues downstream of Leu130. To facilitate protein secretion the same sequence coding for MSP4 signal sequence (Met$_1$-Pro$_{49}$) as in MSP4p21/His was added. Furthermore some codons of MSP4p40/His construct were added, encoding the sequence (Asn$_{50}$-Ser57 and Leu$_{130}$) in MSP4p21 ss1 construct and encoding the amino acid residue Leu$_{130}$ in MSP4p21 ss2.

Construction of the PfMSP5 Synthetic Gene

The same procedure as that described for Pfmsp4 was employed to design the Pfmsp5 synthetic gene. Starting with the GenBank protein sequence of the 3D7 strain, all sequence starting three residues upstream of the GPI-attachment signal was removed and replaced with a hexa-His-tag (SEQ ID NO: 57), three glycosylation sites were disrupted by a serine to alanine mutation (S83, S102 and S126) and the N-terminal signal sequence left intact. The codon modifications implemented by CODOP are documented in Table 2 and the entire synthetic gene sequence is shown in FIG. 6.

MSP5 Codon Usage of 3D7 and Synthetic Gene

| Codon | aa | p.f | H5 |
|---|---|---|---|
| GCA | Ala | 2 | 1 |
| GCC |  | 2 | 2 |
| GCG |  | 0 | 1 |
| GCT |  | 0 | 3 |
| total |  | 4 | 7 |
| AGA | Arg | 6 | 2 |
| AGG |  | 0 | 2 |
| CGA |  | 0 | 0 |
| CGC |  | 0 | 2 |
| CGG |  | 0 | 0 |
| CGT |  | 1 | 1 |
| total |  | 7 | 7 |
| AAC | Asn | 2 | 44 |
| AAT |  | 42 | 0 |
| total |  | 44 | 44 |
| GAC | Asp | 2 | 13 |
| GAT |  | 13 | 2 |
| total |  | 15 | 15 |
| TGC | Cyc | 0 | 4 |
| TGT |  | 7 | 3 |
| total |  | 7 | 7 |
| CAA | Gln | 5 | 4 |
| CAG |  | 1 | 2 |
| total |  | 6 | 6 |
| GAA | Glu | 23 | 23 |
| GAG |  | 6 | 6 |
| total |  | 29 | 29 |
| GGA | Gly | 6 | 5 |
| GGC |  | 0 | 3 |
| GGG |  | 0 | 0 |
| GGT |  | 6 | 4 |
| total |  | 12 | 12 |
| CAC | His | 0 | 9 |
| CAT |  | 4 | 1 |
| total |  | 4 | 10 |
| ATA | Ile | 10 | 0 |
| ATC |  | 1 | 10 |
| ATT |  | 5 | 6 |
| total |  | 16 | 16 |
| CTA | Leu | 3 | 2 |
| CTC |  | 0 | 7 |
| CTG |  | 0 | 2 |
| CTT |  | 2 | 2 |
| TTA |  | 10 | 1 |
| TTG |  | 2 | 3 |
| total |  | 17 | 17 |
| ATG | Met | 6 | 6 |
| total |  | 6 | 6 |
| AAA | Lys | 15 | 5 |
| AAG |  | 3 | 13 |
| total |  | 18 | 18 |
| TTC | Phe | 1 | 6 |
| TTT |  | 5 | 0 |
| total |  | 6 | 6 |
| CCA | Pro | 4 | 3 |
| CCC |  | 0 | 3 |
| CCG |  | 0 | 0 |
| CCT |  | 5 | 3 |
| total |  | 9 | 9 |
| AGC | Ser | 3 | 5 |
| AGT |  | 7 | 8 |
| TCA |  | 8 | 3 |
| TCC |  | 1 | 4 |
| TCG |  | 1 | 1 |
| TCT |  | 5 | 1 |
| total |  | 25 | 25 |
| TAA | stop | 0 | 1 |
| TAG |  | 0 | 0 |
| TGA |  | 0 | 0 |
| total |  | 0 | 1 |
| ACA | Thr | 2 | 0 |
| ACC |  | 1 | 2 |
| ACG |  | 2 | 0 |
| ACT |  | 1 | 4 |
| total |  | 6 | 6 |
| TGG | Trp | 0 | 0 |
| total |  | 0 | 0 |
| TAC | Tyr | 0 | 7 |
| TAT |  | 7 | 0 |
| total |  | 7 | 7 |
| GTA | Val | 3 | 2 |
| GTC |  | 1 | 4 |
| GTG |  | 1 | 2 |
| GTT |  | 4 | 1 |
| total |  | 9 | 9 |
| Codons |  | 247 | 254 |
| % GC |  |  | 45.8 |

Figure 7:
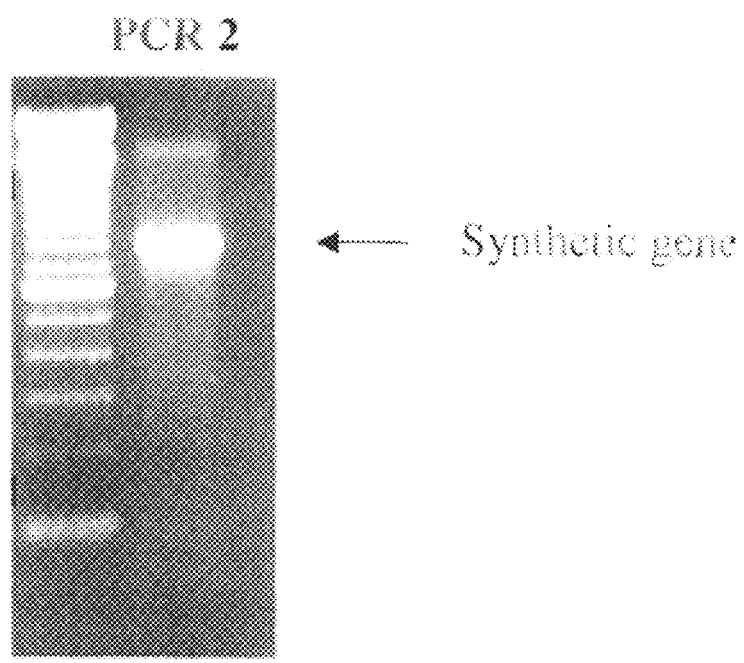
FIG. 7 depicts PCR fabrication of the synthetic gene. A sample of the "Gene amplification reaction" (5 μL) resolved on a 1% agarose gel, flanked by DNA size standards.

PCR assembly of the PfMSP5 synthetic gene was performed as previously described and due to the absence of repeat motifs within the sequence generated a highly pure end product (FIG. 7). The PCR product was gel-extracted, cloned into pMOSBlue and sequenced before being transferred to the pVL1393 vector for integration into the Baculoviral genome (Baculo-gold, Stratagene).

The constructs thus prepared were evaluated, and the results are reported in the following Examples.

EXAMPLE 1

Expression of PfMSP4 in Insect Cells

After generating virus, using standard procedures [36], trial infections were performed in 150 cm² culture flasks (Corning). Infections were performed at a viral multiplicity of 10 for 1 h. Supernatants were harvested after 3 days and batch purified over talon resin. Protein products of the predicted size were seen with constructs MSP4p40/H is (40 kDa) and MSP4p30/H is (30 kDa), but no protein was seen with construct MSP4-EGF/H is (discussed further below). Expression of MSP4p21/His still in preliminary stages of analysis.

Figure 8:
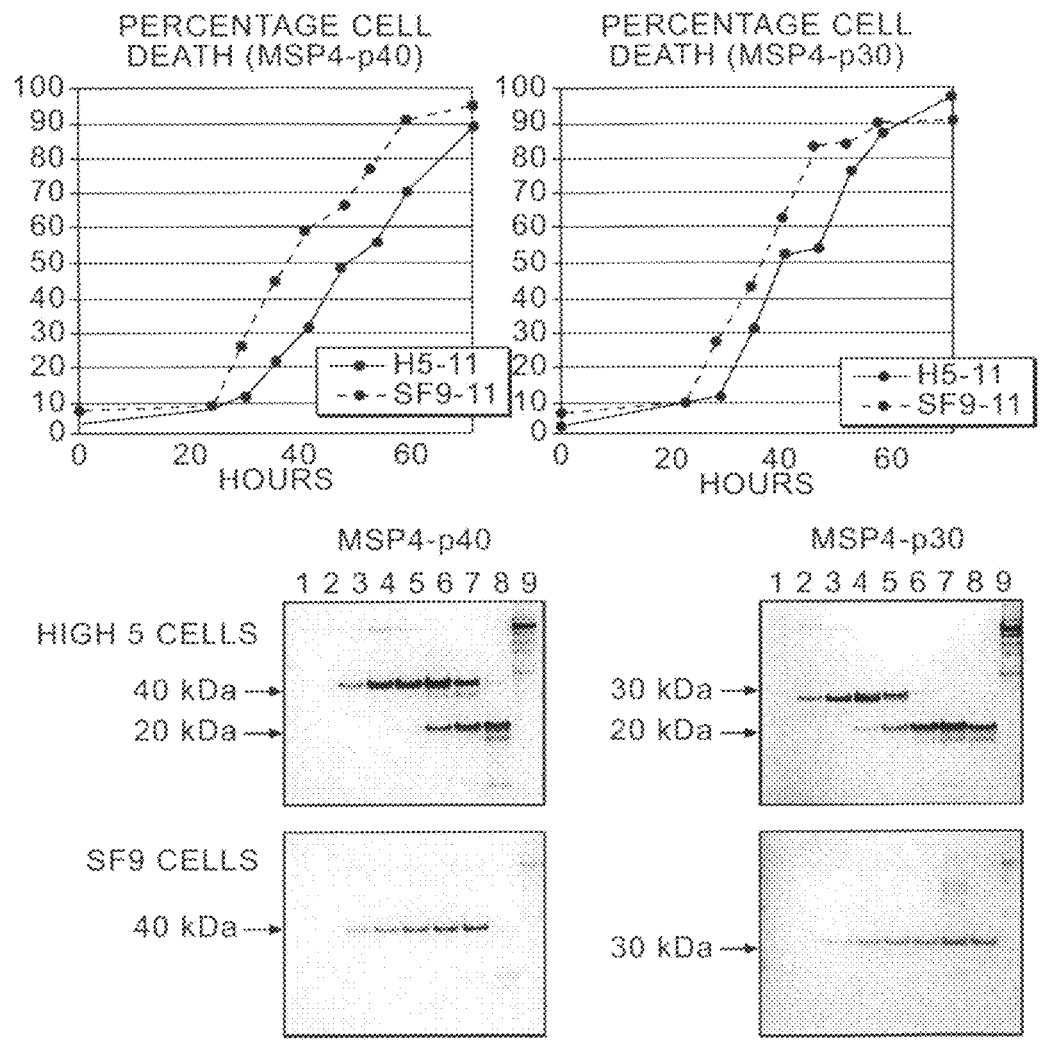
FIG. 8 shows PfMSP4 expression over time in two different insect cell lines. Percentage cell death was calculated by mixing cell suspensions 1:1 with 4% trypan blue and counting total cells and blue cells against a grid under a cover slip. Protein was purified from infected culture SN at 24, 30, 36, 42, 48, 54, 60 and 72 h post infection (lanes 1-8, respectively) and 20 uL of the eluted protein was resolved in 4-12% Bis-Tris™ gels (Invitrogen) and stained with SimplyBlue™ safe stain (Invitrogen). These protein species were not seen in uninfected cell culture (lane 9).

Production of both MSP4p40 and MSP4p30 was scaled up and moved from boxes to spinner flask culture. To optimize protein yields and limit product degradation (frequently seen under the more aggressive conditions of the spinner), a time course experiment was conducted. MSP4p40/His or MSP4p30/His infected spinner cultures (210 mL) were set up for both *Spodoptrea frugiperda* (SF9) insect cells and High Five insect cells. Samples (8 mL) were collected at 24 h, 30 h, 36 h, 42 h, 48 h, 54 h, 60 h and 72 h, analysed microscopically for cell death statistics and then dialysed against 20 mM Tris HCl (pH8); 500 mM NaCl. Proteins were purified over talon resin using a test tube protocol, and eluted into 100 µL of 100 mM imidazole; 20 mM Tris HCl (pH8); 500 mM NaCl. Percentage cell death over time was plotted for each infection and a 20 µL sample of each elution was resolved in parallel for both constructs and cell types (FIG. 8).

As expected the High five cells generated far higher protein yields than the SF9 cells. However, it was observed that after long expression periods (more than 48 hrs) when protein degradation had begun, the MSP4 protein did not degrade completely, but rather degraded into a smaller, stable product of approximately 20 kDa (MSP4p20). This product was also seen in later stages of the MSP4p30 infection. Since all protein was purified via the C-terminal his-tag, this product must include the EGF-like domain and some up stream sequence forming a tight structure that is resistant to protease. This agrees with finding of Wang et. al. (2001) [13], that the region upstream of the EGF-like domain harbours reduction sensitive B-cell epitopes.

EXAMPLE 2

N-Terminal Sequencing and Mass Spectrometry

Using the information obtained from the time course experiment, three different pure MSP4 protein preparations have been generated by collecting the culture SN at different time points. Firstly, the full length MSP4, denoted MSP4p40, secondly, the full length modified product, MSP4p30, and thirdly, the breakdown product MSP4p20. Average protein yields for each product in standard High Five spinner culture has been found to be 8 mg/L, 6 mg/L and 15 mg/L respectively, and reflects the time of harvest, with products harvested at earlier time points yielding less protein. In light of recent developments made in commercial Baculovirus competence (Henogen) it is believed that these yields are minimal estimates N-terminal sequencing of each product generated a strong and clear signal (p40: starting at residue 41-MRILG, p30: starting at residue 41-MRILA, p20: starting at residue 132-KSPKE) and revealed that the in vivo *P. falciparum* signal sequence may in fact be twice as long (40 residues as opposed to 20) as that predicted by PlasmoDB (available on the internet). The identity of MSP4p40 and MSP4p20 has also been confirmed by Mass Spectrometry, and the proteins have actual molecular masses of 23.554 kDa and 13.714 kDa, respectively.

The N-terminal sequence of the baculovirus-expressed MSP4 likely identifies the signal sequence used by the parasite. Firstly, the MSP4-EGF/His construct contains the PlasmoDB predicted signal sequence plus 3 downstream residues and was never detected in culture SN. Secondly, the N-terminal cluster of polymorphic sites identified within the Pfmsp4 gene starts at the 45th codon. As suggested by the analysis documented in Polson et al., 2005 [33] the region of the gene downstream of codon 45 is the target of an effective immune response for which it would appear to have evolved an evasion mechanism through balancing allelic types within the population (involving residues 52 and 74; see FIG. 5). Thus it seems likely that the processed N-terminus of PfMSP4 consists of 4 conserved residues that contribute to the signal sequence cleavage site (MRIL) (SEQ ID NO: 46) followed directly by a cluster of polymorphic sites capable of reducing the effectiveness of immune responses directed preferentially to this more accessible region of the protein.

EXAMPLE 3

Signal Sequence Hydrophobicity

Figure 10:
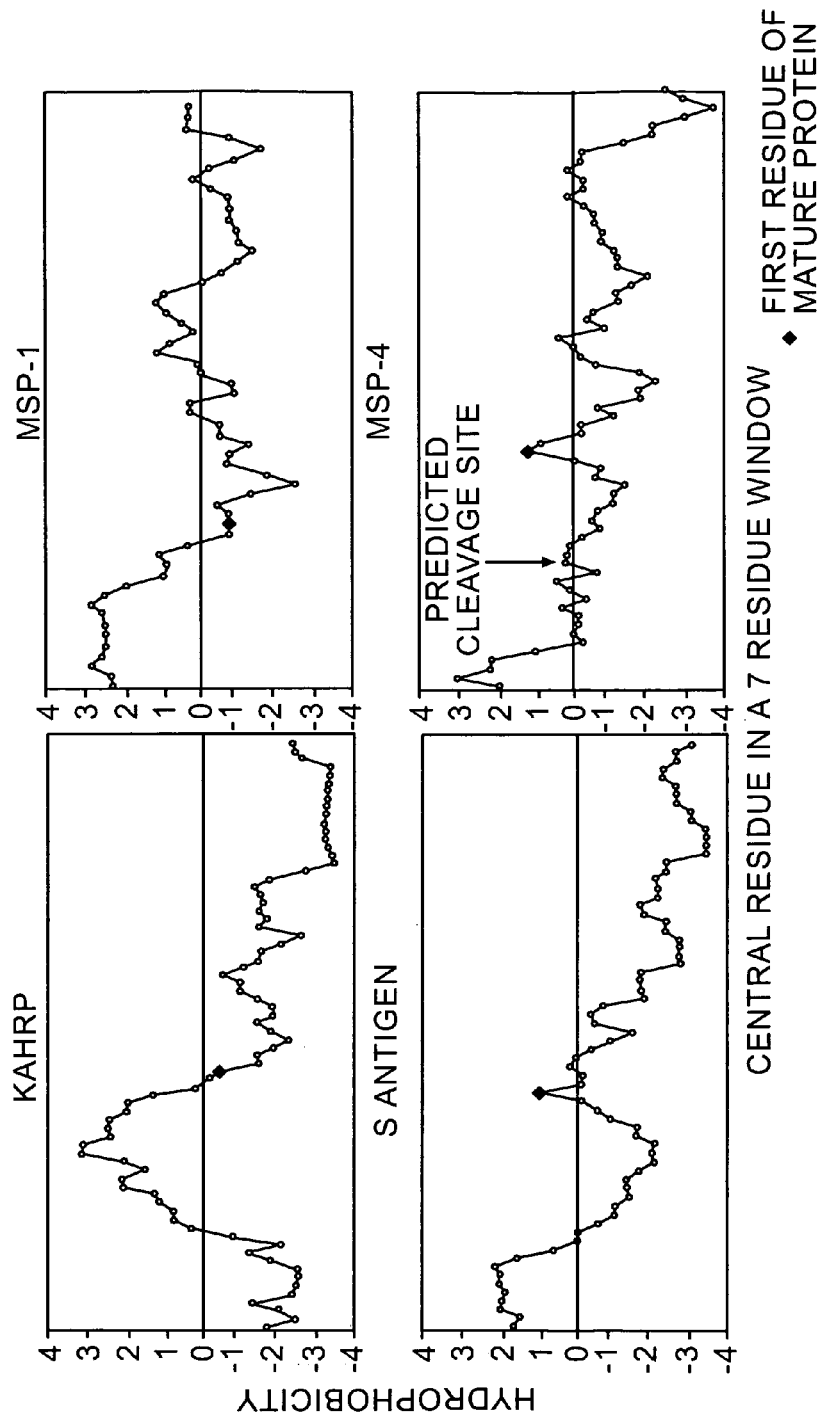
FIG. 10 shows the hydrophobicity profile of approximately 80 amino acid residues centered around the reported signal cleavage sites for three known malaria antigens. The first residue of the mature protein is indicated by a black diamond. The profile of S-antigen signal sequence cleavage is comparable to that seen for MSP4 in the baculovirus system. A hydrophobicity analysis of the approximately 80 residue sequence was performed using PEPWINDOW software. The hydrophobicity of a 7 residue window was calculated. See Nancer et al. "*Plasmodium falciparum* signal sequences: simply sequences or special signals?" *Inter. J. Parasitology* 31:1371-9 (2001).

To further corroborate that the signal cleavage site used for MSP4 constructs by the Baculovirus-system reproduces natural cleavage, a bioinformatics study was conducted looking at previously reported natural *P. falciparum* signal sequences. In 2001 a study was published comparing known *P. falciparum* signal sequence cleavage sites [37]. Due to the technical difficulties involved in obtaining such data, only 10 such sequences exist. For the purposes of this study, eighty residues of protein sequence, centred around the reported signal sequence cleavage site, of each protein were chosen and submitted (via the Pasteur server) to calculate values of local hydrophobicity. The hydrophobicity profile of three protein cleavage sites reported in Nacer 2001 and that of MSP4p40 in the baculovirus-system are shown in FIG. 10. In the top panel, both the KAHRP and MSP1 signal sequences display a classic hydrophobicity profile, with cleavage occurring just after values of hydrophobicity traverse the line of neutrality (positive to negative). It is known that the cleavage of the PfMSP1 signal is faithfully performed by the Baculovirus-system (Bonnet et. al. 2005). The same marked change in local hydrophobicity if not present within the N-terminal of the MSP4p40 protein sequence at the predicted cleavage site and cleavage actually occurs further downstream after the biggest local change in hydrophobicity (negative to positive). This profile matches that seen with the S-antigen and is thus not unique, adding weight to the finding that the MSP4p40 signal sequence is 40 residues in length.

EXAMPLE 4

Expression of PfMSP5 in Insect Cells

MSP5/His viral stocks were generated as previously described, and trial infections and a time course study were conducted as described for MSP4p40/His. As shown in FIG. 11, three different PfMSP5 derived products were detected migrating at approximately 45, 35 and 10 kDa under SDS-page gel electrophoresis. Interestingly, the two larger products were seen to appear simultaneously during the early stages of the time course experiment, rather than the larger being generated and subsequently degrading to form the smaller. Another striking difference to the situation seen with PfMSP4 was the inversed protein production capabilities of the two cell lines studied, with SF9 cells far out performing the faster growing and more fragile High Five cells. This in itself was the first piece of evidence suggesting that PfMSP5 possesses very different properties to PfMSP4. The second came from the N-terminal sequencing data.

EXAMPLE 5

N-Terminal Sequencing and Mass Spectrometry

It has not been possible to obtain a signal for the N-terminal of the two largest products of MSP5 expression suggesting that they both harbour an N-terminal modification that blocks the breakdown of the peptide backbone, an essential event in N-terminal sequencing. Sequencing of the smaller 10 kDa product was successful and has defined the N-terminal of this product to start at residue 189: YNKVE [SEQ ID NO: 26]. The identity of this product has also been confirmed by Mass Spectrometry and it has an actual molecular mass of 7.746 kDa. In addition the sequence of the MSP5 viral genome has been confirmed and the residues YNKVE [SEQ ID NO: 27] are only present in the correct ORF, thus these as yet undefined products must be PfMSP5.

The mass values obtained by MALDI-MS for the two largest MSP5 products are 24.679 and 20.551 kDa, respectively, and did not match any polypeptide derived from the MSP5 protein sequence alone, supporting the idea that these protein are carrying a post-transcriptional modification. To investigate possible N-terminal blocking modifications, the MSP5 sequence was submitted to prosite via the ExPASY home page. This revealed the presence of two N-myristoylation sites that could direct co-translational addition of a C14 fatty acid (at residue 42:GGFTSK (SEQ ID NO: 47) and at residue 66: GSLPTK (SEQ ID NO: 48)) [38]. However, while these modifications are exclusively N-terminal and could block N-terminal sequencing, they do not give rise to the appropriate mass values (24,015 and 21,301, respectively). However, motif guided N-terminal modification of glycine residues is not the only form of myristoylation that is performed by eukaryotic cells. They can also post-transcriptionally modify any N-terminal glycine and any lysine with a myristoyl group (review below). Working with these possibilities, close matches are obtained at 24.673 kDa and 20.553 kDa by assuming that each MSP5 product (p45 and p35) carries two fatty acid modifications, although the putative positions are at present undefined.

EXAMPLE 6

Fatty Acid Modifications and *Plasmodium*

There are several different types of extra translational modification that are used by eukaryotic cells, including glycosylation, palmitoylation, N-myristoylation and myristoylation. Of these, the first is not present in the MSP5 protein expressed here. All glycosylation sites were removed from the protein sequence during the construction of the synthetic gene, as it is known that this type of modification is not performed by *P. falciparum*. The second type of modification is less well understood in eukaryotes as a whole and it is believed that palmitoylation can occur via both enzyme dependent and enzyme independent pathways [39]. To date there has been no report of any palmitolyated *P. falciparum* proteins. However, protein N-myristoylation has been shown to be important in *Plasmodium*. A Pf N-myristoyltransferase gene homolog has been identified (PlasmoDB PF14_10127) and found to be highly homologous to the human and yeast gene orthologues [40,41]. If this enzyme is as important to *Plasmodium* as it is to other parasitic protozoa such as *Trypanosoma brucei* and *Leishmania major*, the N-myristoylation of multiple proteins can be expected to be essential for parasite growth [41]. Indeed, N-terminal myristoylation of PfADF (a ribosomal factor) has been shown to be important to mediate binding of GTP and facilitate enzyme activity [42]. This fatty acid modification (both at an N-terminal glycine and an internal lysine) has been shown to play a variety of roles in higher eukaryotes involving the localization of proteins to membranes and the stabilization of protein-protein interactions [39, 43-45].

EXAMPLE 7

In the Baculo-System

Since baculovirus infection of insect cells is a higher order eukaryotic system it is capable of performing many types of more evolved protein modification. Indeed, this system has been specifically employed to generate several N-myristoylated proteins, the best described being NAP-22 [46].

EXAMPLE 8

Raising Antibodies

Figure 12A:
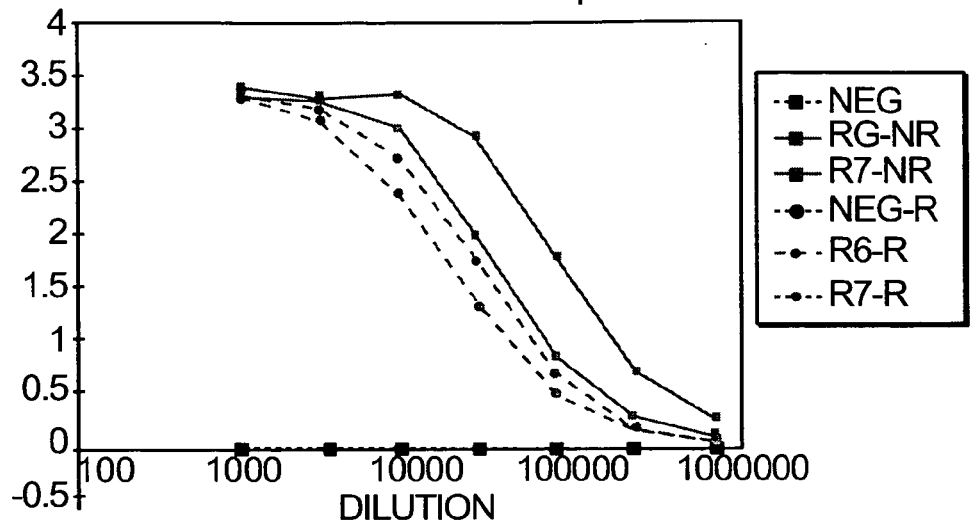
FIG. 12 relates to polyclonal antisera raised in Rabbits. ELISA endpoint titres of sera raised against (A) the full-length MSP4p40 (R6-7) and (B) the MSP4 breakdown product p20 (R8-9), analysed using native (NR) or irreversibly reduced (R) MSP4-p40, as the coating antigen. Serum R8 loses over 50% binding activity when the MSP4 antigen is reduced. Pre-immune sera is marked as NEG. Panel (C) shows the titres of anti-MSP5 sera (56-57) analysed using MSP5-p45 and p35 as the coating antigen
Figure 12B:
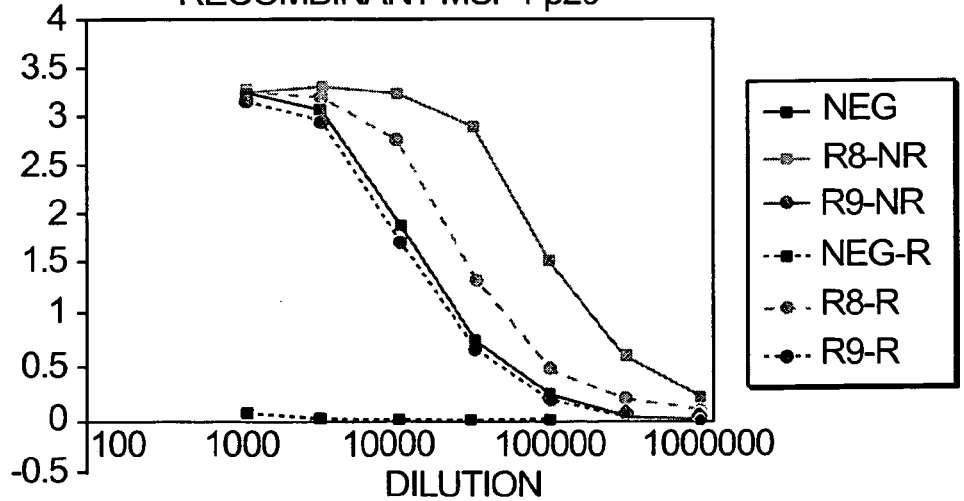
Figure 12C:
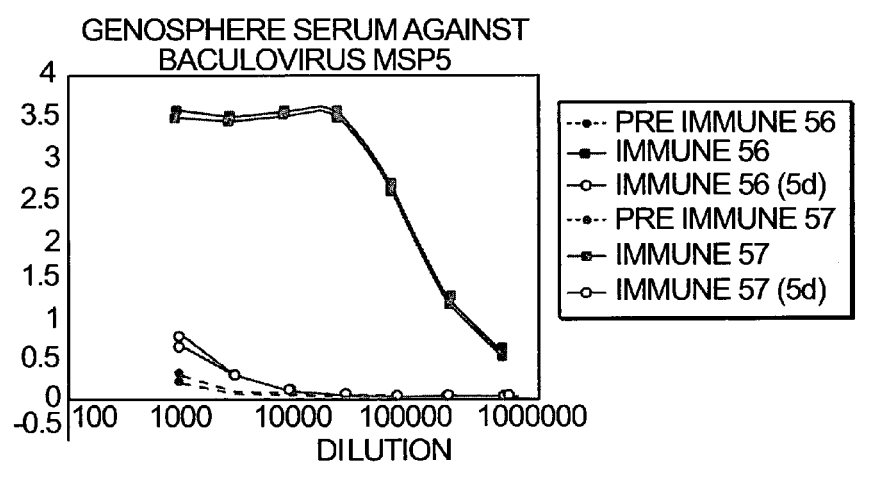

Rabbit polyclonal antiserum was generated by EUROGENTEC, using standard immunization procedures, for recombinant MSP4p40, MSP4p20 and MSP5 (p45 and p35). All rabbits were negative for MSP4 or MSP5 before immunization (two rabbits per antigen) and produced high titres of specific serum antibodies as determined by ELISA after 3 or 4 immunizations. Endpoint titres against reduced and non-reduced recombinant protein are shown in FIG. 12. As shown in panel B, recognition of MSP4p20 by antibodies from rabbit No. 8 is reduced by more than 50% when the antigen is reduced, indicating that many of the epitopes of the MSP4p20 protein are conformational. Since reduction primarily affects disulfide bonded structures, this data shows that the EGF-like domain of MSP4p20 is intact and involved in forming at least one B-cell epitopes.

EXAMPLE 9

Parasite Derived MSP4

Figure 13:
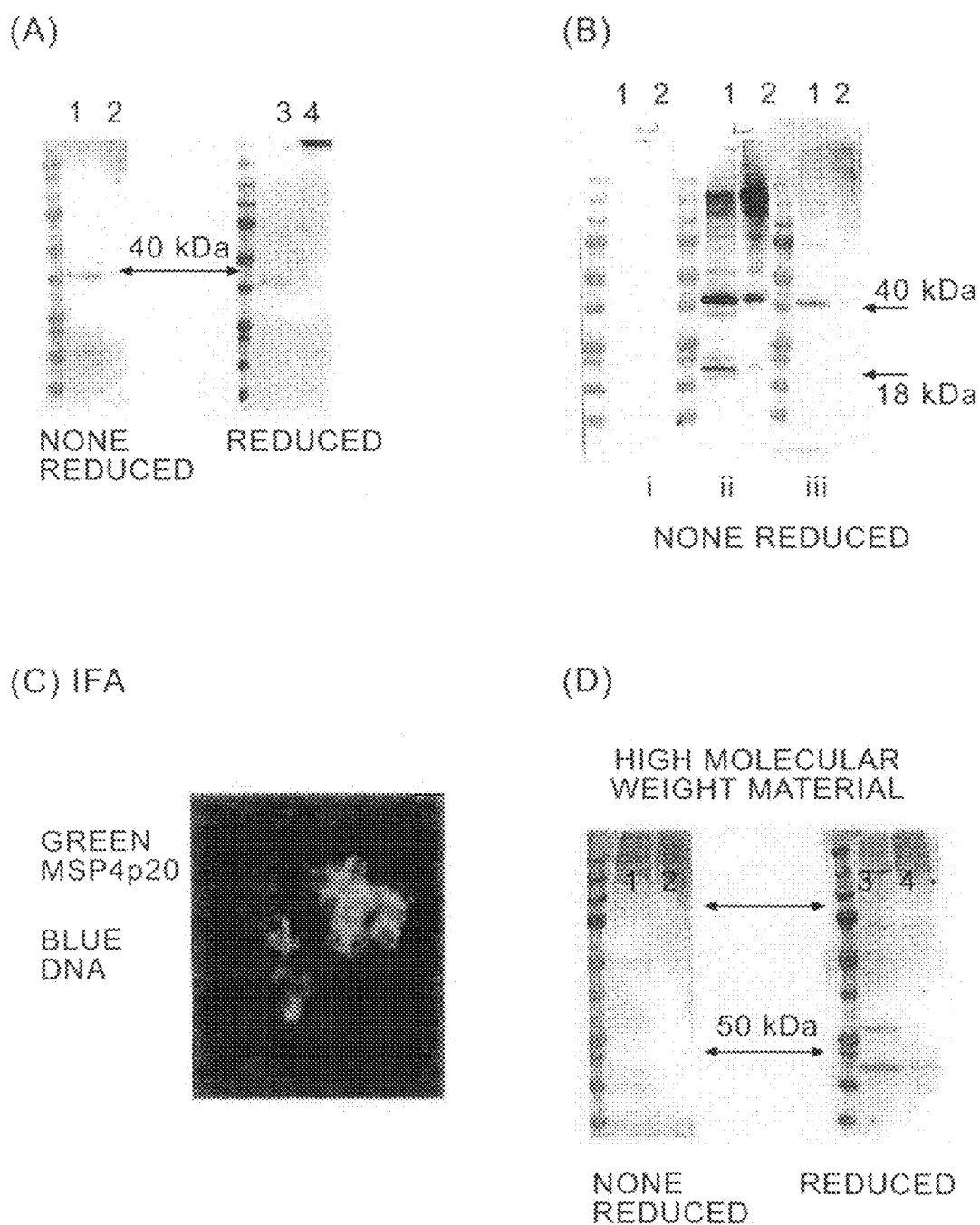
FIG. 13 depicts the results obtained by probing parasite material with polyclonal sera raised against the baculovirus expressed antigens and MSP4p40 affinity purified sera from either a pool of human sera from Dielmo or a pool of antiMSP4 rabbit sera. Asynchronously growing parasites were extracted from iRBC and crudely fractionated using the protocol of Wang et al (2003) [9]. Each lane 1 of each immune-blot was loaded with a non-reduced Triton X100™ soluble parasite fraction, lane 2 with a non-reduced membrane fraction, lane 3 with a reduced Triton X100™ soluble parasite fraction and lane 4 with a reduced membrane fraction (Panels A, B and D). Panel C shows IFA data obtained with air-dried *P. falciparum* infected RBC.

Preliminary immuno-blot data has been generated using the previously described polyclonal immune serum and is shown in FIG. 13. The data for MSP4 is in agreement with results published by the group of R. Coppel [9] where a 40 kDa protein is detected exclusively in the Triton X100™ solubilised fraction of late stage parasite preparations (FIG. 13A). To investigate the properties of the C-terminal region of MSP4, MSP4p20, a pool of rabbit sera (R6-9) and human sera collected in Dielmo, Senegal in 2002, were affinity purified against immobilized MSP4p20 (Amersham: NHS-activated Sepharose 4 fast Flow™). When asynchronous parasite material (separated by SDS-page and transferred to a nitrocellulose membrane) was probed with these sera, in addition to the previously observed band at 40 kDa, a band of approximately 18 kDa was also seen (FIG. 13B), suggesting that in natural infection the MSP4 antigen may either undergoes proteolytic processing similar to MSP1p42 or may be degraded by proteases in a self-limiting fashion as obtained in the later stages of baculovirus infection. To further confirm the natural existence of MSP4p20 epitopes on *P. falciparum* merozoites, an indirect immunoflourescence assay (IFA) was performed on air-dried asynchronously growing parasite cultures. Merozoite specific staining was seen with the human anti-MSP4p20, when no staining was seen with the secondary antibody alone or with malaria naive sera (FIG. 13C).

EXAMPLE 10

Parasite Derived MSP5

Immuno-blot data obtained using polyclonal sera raised against baculovirus expressed MSP5 shows a very different profile to that published by other groups [9]. who have had apparent problems detecting MSP5 and suggest that it is expressed at low levels. Immuno-blot data of this invention show strong signals with antiMSP5 specific sera (FIG. 13D). Unlike MSP4, parasite derived MSP5 is also present in the membrane fraction of crudely prepared parasite extracts suggesting that it does not fractionate in a fashion consistent of a protein that is only carrying a GPI anchor. Indeed, when looking at reduced parasite material it is possible to conclude that the polyclonal sera raised against the putatively N-myristoylated MSP5 can cross react with other N-myristoylated proteins, further supporting the idea that this is a important and frequently used post-translational modification in *P. falciparum*.

EXAMPLE 11

The Analysis of Human Immune Serum

Figure 14:
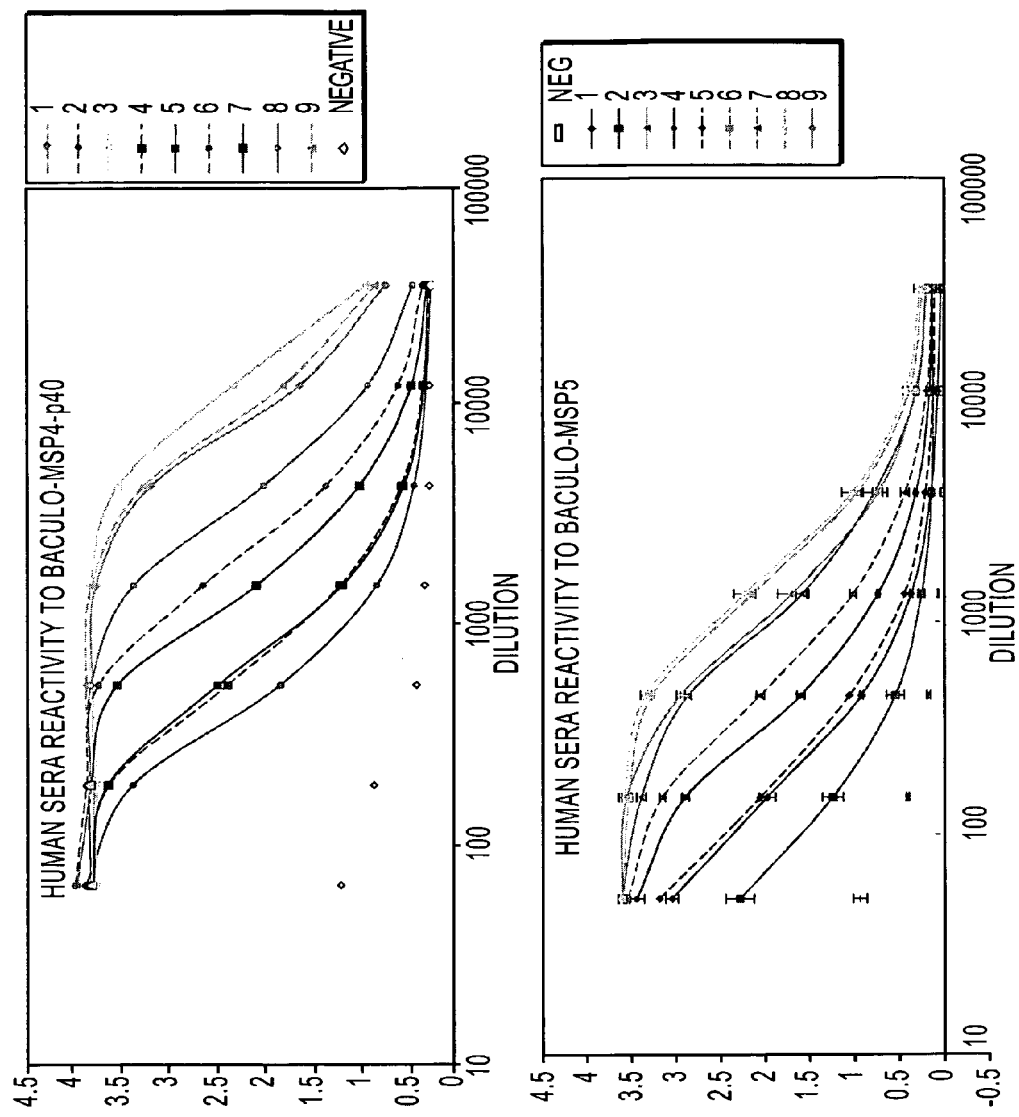
FIG. 14 shows the ELISA analysis of sera from 9 immune adults (18-49 yrs) from Dielmo collected in 1990 at the peak of the rainy season. Plates were coated with MSP4p40 (A) or MSP5p45 and p35 (B).
Figure 15A:
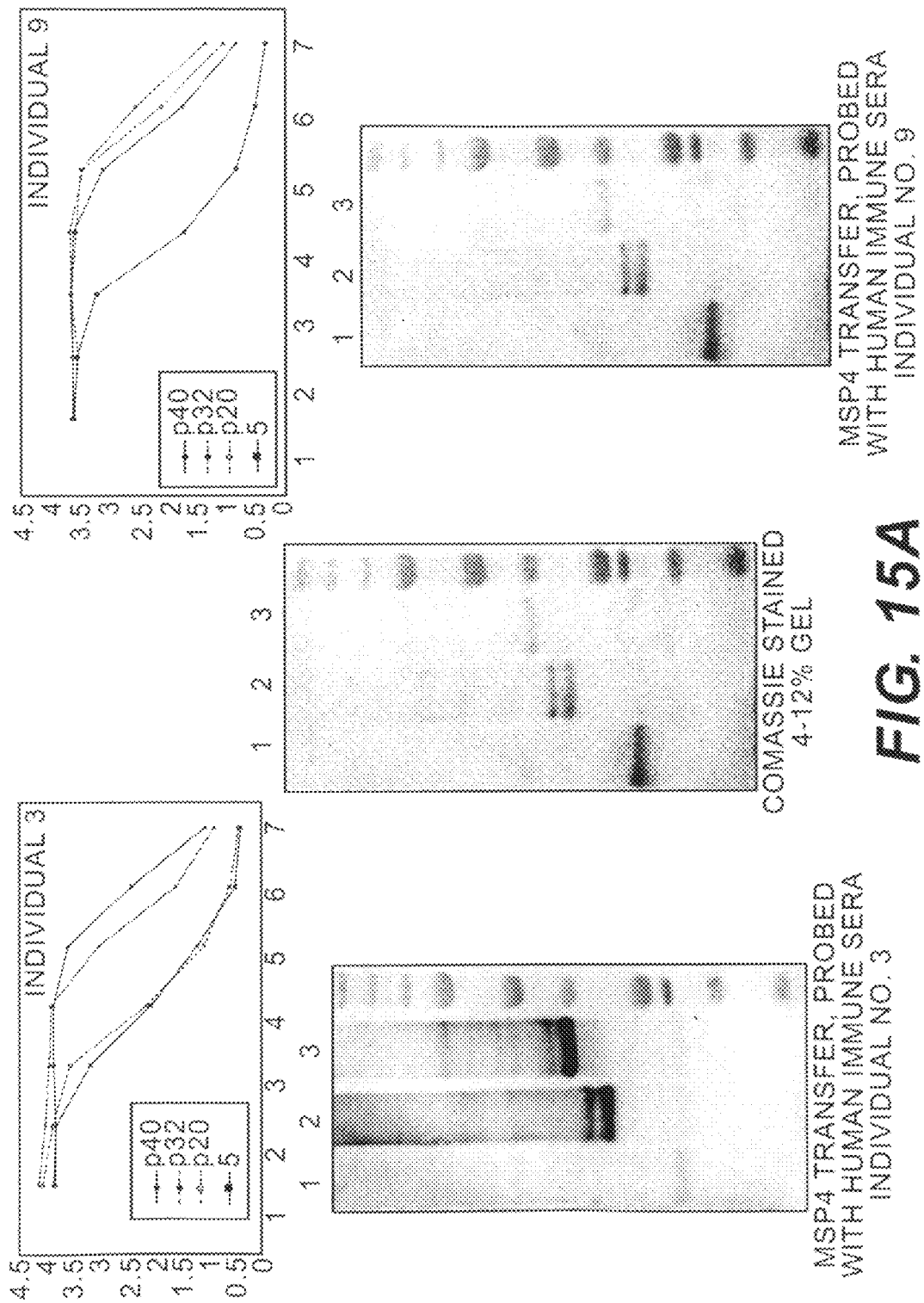
FIG. 15 is an immune-blot of (A) recombinant MSP4p40, p30 and p20 (lanes 3, 2 and 1, respectively) using human immune sera from individuals No. 3 and 9. (B) Immune blot analysis of recombinant MSP5 using human immune sera from individual No. 8.

To confirm that the protein products of the invention are recognized by the antibodies of malaria-infected individuals, the sera of 9 randomly selected semi-immune adults living in an endemic village in Senegal (Dielmo) were analysed by ELISA (FIG. 14). All individuals were positive for all protein products (having OD values greater than control sera plus three times the standard deviation). Relative titres varied between individuals and from product to product, but overall end point titres were $1\times10^5$ for MSP4 and $1\times10^4$ for MSP5. Western blot analysis (FIG. 15) was performed using the sera from two individuals highly positive for MSP4 (individuals 3 and 9) and one individual highly positive for MSP5 (individual 8). As previously seen with anti-MSP1p19, the human antibodies to EGF-containing merozoite surface proteins has particular affinity for aggregated material (FIG. 15).

EXAMPLE 12

Anti-MSP4 Antibodies in Senegal; A Role in Protection

To further investigate a putative role for anti-MSP4 antibodies in natural infection, an epidemiological study was conducted. The three different purified forms of MSP4, p40, p30 and p20, were evaluated into a large prospective study that has been documented elsewhere (see reference [47]) and is detailed below in Example 16.

In summary, each form of the recombinant MSP4 protein was strongly recognized, with a sero-prevalence of >90%, but showed significantly different mean IgG OD ratios (p40=20±10, p30=12.3±7.3 and p20 17.3±10). As seen with all malaria antigens, antibody titres increase with age and correlates of protection must be addressed using an age adjusted progression model. Using this form of analysis anti-MSP4-p30 and anti-MSP4-p20 but not MSP4p40 antibodies were positively correlated with a reduced incidence of clinical malaria episodes (P=0.036, P=0.018+0.067 respectively). These findings reinforce the identification of potentially balancing polymorphisms within the N-terminal region of MSP4 protein [33] and more specifically support the concept of deleting this region of the protein in MSP4 based vaccine constructs.

EXAMPLE 13

Anti-MSP5 Antibodies in Senegal; A Role in Protection

To further investigate the role of antiMSP5 antibodies in natural infection, an epidemiological study was conducted. A preparation containing the two high molecular weight forms of MSP5 was analyzed as described elsewhere (see reference [47]).

While sero-prevalence was lower for MSP5 than for MSP4 (59%), a highly significant statistical correlation with reduced numbers of clinical malaria episodes was observed using the age adjusted progression model (P=0.0028). As discussed previously, this antigen may carry a fatty acid modification with potential implications for lipid induced immunogenicity and immune responses in anti-infection immunity, as seen for GPI modifications [48]; Bonnet et al 2005, publication in preparation).

In summary, PfMSP4 has a C-terminal EGF-like domain and is bound to the merozoite surface by a GPI anchor. Its function, although unknown, appears to be essential for parasite survival, since no viable PfMSP4 "knock-out" mutants have been observed. Three recombinant PfMSP4 constructs have been expressed as soluble, secreted proteins in the baculovirus-insect cell expression system, to optimize reproduction of the native antigen, including proper folding of the EGF-like domain. Two constructs correspond to the MSP4 exo-antigen (minus C-terminal hydrophobic residues to permit secretion), with or without the deletion of 30 amino acids from a polymorphic region near the N-terminus (MSP4p30) and MSP4p40, respectively. A third 20 kDa protein corresponds approximately to the C-terminal half of MSP4 including, the EGF domain (MSP4p20). Expression of this antigen in a more direct fashion is being evaluated using the previously described construct MSP4p21/His. Anti-MSP4 antibody responses to the 3 different antigens were compared with regard to naturally acquired immunity in humans exposed to malaria, in a cross-sectional study of 205 individuals living in a mesoendemic village where transmission is seasonal.

Before the transmission season, the 3 constructs were strongly recognized: with a sero-prevalence >90%, but with significantly different (P<0.01) mean IgG OD ratios of 20±10, 12.3±7.3 and 17.3±10 for MSP4p40, MSP4p30 and MSP4p20, respectively (approx. titres $5\times10^{-3}$). Antibody responses to the MSP4 constructs were age-associated with individuals <15 yr. old having significantly lower IgG levels than adults (P<0.001, Rho 0.25-0.33). Analysis of clinical attacks during the subsequent six-month period, including the transmission season, in an age-adjusted model, showed that the presence of IgG responses to MSP4p30 and MSP4p20, both lacking the polymorphic region, but not MSP4p40 with the polymorphic region, was significantly associated with a reduced incidence of malaria clinical episodes (P<0.05, rate #0.75). Together, these results indicate: (i) there is a strong naturally acquired IgG response to PfMSP4, monitored using the baculovirus recombinant antigen; (ii) anti-MSP4 IgG correlates with protection against clinical malaria, and; (iii) the IgG response to the variable region, may interfere with otherwise protection-associated anti-MSP4 IgGs.

EXAMPLE 14

PfMSP4 Monoclonal Antibodies

Four monoclonal antibodies (mAb) specific for PfMSP4 recognize 3 different epitopes.

Monoclonal antibody L11-16 is representative of 2 others induced by p40 (complete PfMSP4 polymorphic ecto-domain). Its reduction insensitive epitope (17B) is located in the N-terminal half of PfMSP4 (non-p20; 16A). It is particularly reactive with heterogeneous aggregates of PfMSP4, the formation of which are reduction sensitive (FIG. 16A), and serves to demonstrate that high molecular weight material in non-reduced (nR), and partially reduced. (R) SDS-PAGE is indeed PfMSP4 (as seen previously for baculovirus PfMSP1p19).

Monoclonal antibody F12-7 was induced by PfMSP4p30 (lacking the polymorphic region) and recognizes a reduction insensitive epitope in the p20 C-terminal half of PfMSP4 (FIGS. 16B and 17B). Its apparent reduced reactivity with aggregates compared to L11-16 may be due to its considerably lower affinity:

| Clone | Isotype | KD/MSP5 | epitope |
|---|---|---|---|
| L11-16 | Ig G1 | $3.2\ 10^{-9}$ M | A |
| F12-7 | Ig G1 | $1.0\ 10^{-7}$ M | C |

EXAMPLE 15

PfMSP5 Monoclonal Antibodies

Seven monoclonal antibodies (mAb) specific for PfMSP5 (p45+p35) recognize 5 different epitopes.

Monoclonal antibody G21-2 recognizes both the p45 and p35 PfMSP5 products (FIG. 18A) and its epitope is not reduction sensitive (FIGS. 18A and 19A). It reacts with discrete higher molecular weight aggregates (FIG. 18A, nR), the formation of which are reduction sensitive (FIG. 18A, R).

Monoclonal antibody J18-14 recognizes only the p45, and its epitope is reduction sensitive (FIG. 19B). It is also reactive with aggregates.

Since these antigens were purified via a C-terminal hexa-histidine tag, the p45 and p35 are thought to differ on the N-terminus. These characteristics suggest that the J18-14 epitope may correspond to a conformational structure involving both the C-terminal EGF domain and the N-terminus. Both mAbs have similar affinities:

| Clone | Isotype | KD/PfMSP5 | epitope |
|---|---|---|---|
| G21-2 | Ig G1 | $2.8\ 10^{-8}$ M | B |
| J18-14 | Ig G1 | $4.2\ 10^{-8}$ M | D |

The reactivities of these 2 mAbs can be used to define the PfMSP5 product.

EXAMPLE 16

Immune Sera and Cohort of Exposed Individuals

The following results were obtained using (A) a control pool of hyper-immune sera taken from individuals living in endemic areas who do not manifest disease symptoms (B) individual sera from the village of Dielmo (holo-endemic transmission) collected in June 2005 and (C) a cohort of 205 sera collected in the village of Ndiop (meso-endemic transmission) in July and August 2000 before the beginning of the transmission season. The cohort included 108 males and 97 females between the age of 3 and 75 yrs old. Clinical accesses were actively recorded during the 5 following months and a total of 278 clinical episodes were treated (Perraut et al, JID 2005 191 264-271).

Analysis Protocol (1) Optimization of antigen coating (2) selection of standard sera dilution to be tested (3) systematic analysis of a cohort of sera (4) calculation of the median OD ratio value (5) stratification of the results by age (6) functional analysis of select sera for invasion and growth inhibition (7) iso-typing for a select group of sera (8) statistical analysis of results, stratified as a function of the median OD ratio, against clinical episode data.

(1) Calibration: Testing a Dilution Series of "Sera Hyper Immune" (SHI) and Selected Individuals from the Village of Dielmo (2005) Using 2 Antigen Coating Concentrations of 1 and 0.5 µg/ml.

RESULT: Coating with 0.5 µg/ml was found to be optimal as the results were the same as seen with 1 µg/ml of antigen for individuals from both villages and the SHI. The responses of selected individuals were stronger in Dielmo than Ndiop and MSP5 showed lower magnitude Ab responses than MSP4. See FIGS. 20A and 20B.

(2) Calibration: Titration of Shi and Positive Serum from Dielmo

RESULTS: Referring to FIGS. 21A, 21B, 21C, and 21D, when using serum from Dielmo (60605), anti-MSP4 responses were highly positive (>SHI). However, the OD's were relatively low compared to the OD's obtained later with the Ndiop cohort of 2000, nevertheless, the titres of the SHI were comparable. It would appear at first glance that the Ab's detected have a relatively low affinity as shown by the sharp angle of the curves (compared to those against MSP1 from previous studies)

| SHI titre against | MSP5 = 1/1600 |
|---|---|
|  | MSP4-40 – MSP4-30 – MSP4-20 = 1/3200 |

(3) Analyses of the Ndiop Cohort 2000: Primary Results

The SHI was systematically titrated in each assay. OD ratios were calculated with respect to the SHI control series on each plate. For this cohort, the OD ratios at 1/200 dilution were all high, although the actual titres were average (OD ratio values of between 4-6 give end point titres of around 1/2000)

(Result Below)

Results of Titres/OD Ratio

|  |  | MSP5 | | MSP4 K40 | | MSP4 K20 | | MSP4 MOD II | |
|---|---|---|---|---|---|---|---|---|---|
|  |  | SHI | 60605 | SHI | 60605 | SHI | 60605 | SHI | 60605 |
| calib2 | OD_r | 4.0 | 13.6 | 31.0 | 36.1 | 14.9 | 30.0 | 19.1 | 29.5 |
|  | titre | 1600 | 6400 | 6400 | 25600 | 6400 | 25600 | 6400 | 25600 |
| calib 1 | OD_r | 5.1 |  | 36.8 |  | 22.5 |  | 26.1 |  |
|  | titre | 3200 |  | 12800 |  | 3200 |  | 12800 |  |
| Ndiop_00 | OD_r | 6.6 |  | 28.4 |  | 24.4 |  | 18.6 |  |
|  | titre | 1600 |  | 12800 |  | 6400 |  | 12800 |  |

(4) Incidence of Responders

In the following table are shown the characteristics of the Ab responses from the cohort of individuals from Ndiop 2000.

Positive responders were considered with an OD ratio of greater than

2. As shown below, MSP4 was recognised by almost all individuals (>90%) and MSP5 recognition was substantially lower (approx. 60%).

| | Statistiques descriptives n = 205 | | | | | | | |
|---|---|---|---|---|---|---|---|---|
| | MPS4-20 | | MSP4-40 | | MSP4-mod2 | | MSP5 | |
| | DO | rtDO | DO | rtDO | DO | rtDO | DO | rtDO |
| Moy | 1.30 | 16.8 | 1.50 | 19.9 | 1.28 | 12.3 | 0.38 | 3.9 |
| Médiane | 1.33 | 17.3 | 1.83 | 24.3 | 1.35 | 12.9 | 0.21 | 2.4 |
| Dév. Std | 0.82 | 10.0 | 0.78 | 10.0 | 0.80 | 7.3 | 0.45 | 3.8 |
| Minimum | 0.02 | 1 | 0.02 | 1 | 0.01 | 1 | 0.01 | 1 |
| Maximum | 2.63 | 32.4 | 2.47 | 32.2 | 2.72 | 26.9 | 2.63 | 23.2 |
| incidence rep | 94% | | 97% | | 90% | | 59% | |
| incid <15 ans | 89% | | 93% | | 80% | | 49% | |
| incid >15 ans | 98% | | 100% | | 97% | | 66% | |

(5) Correlation with Age and with Other Anti-MSP Responses

Referring to FIGS. 22A, 22B, 22C, and 22D, there was a significant correlation with other anti-MSP responses
 With MSP1 significant Rho # 0.27-0.36
 Between various MSP4 antigens Rho >0.9
 Between MSP4 and MSP5 Rho # 0.44-0.47

There was a significant correlation with age of individuals in the Ndiop cohort (P<0.001, Rho from 0.33 to 0.22), however, slightly less marked than with MSP1. The anti-MSP5 Ab response was the least correlated with age, but individuals <15 yrs old had significantly lower level of Ab.

Focusing on MSP4: Differences in MSP4 Antigens

Referring to FIG. 23, there are highly significant differences in the levels of recognition of the different fragments of MSP4 (P<0.001). Paradoxically, the smallest and biggest antigens (p20 and p40) are better recognized than the antigen MSP4-30 (or MSP4md2), which itself is only 30 residues smaller than the full-length MSP4 (MSP4-40). This result is interesting, as it seems to correspond with the existence of an immune evasion strategy, where antibody responses are focalized against the variable domains. This could explain the absence of a correlation between IgG responses and invasion inhibition (see below).

(6) Relationship to Functional Tests

Figure 24A:
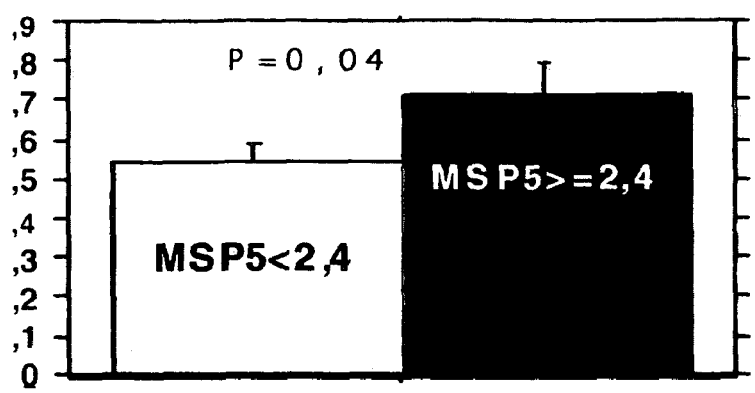
Figure 24B:
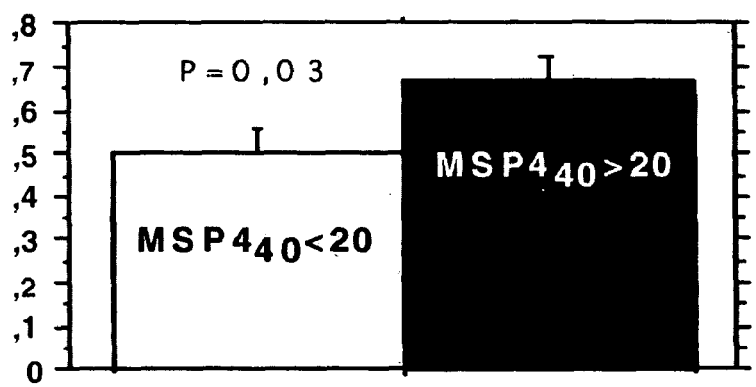

Referring to FIGS. 24A and 24B, there is not a significant difference in growth or invasion inhibition on the basis of a dichotomised comparison between median OD ratio values for MSP4p40, MSP4p20, MSP4_mod (p30) (<20>) or MSP5 (<2.4>). (This property appeared only to be statistically significant for anti-MSP1p19 Ab's in this cohort). However, there is a significant difference regarding merozoite phagocytosis. This functional correlate with merozoite phagocytosis was expected, as this phenomenon is associated with an overall increase in specific Ab titres (thus OD ratio), which are known to increase as a function of age in endemic area. See figure below:—

(7) Isotyping

Figure 25A:
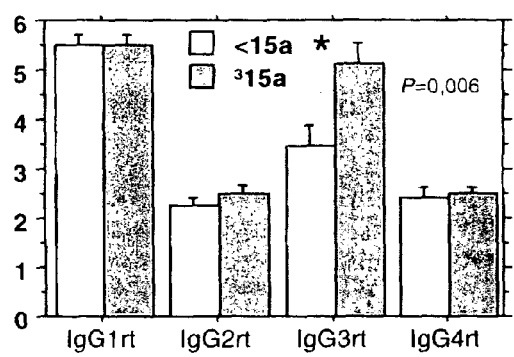
Figure 25B:
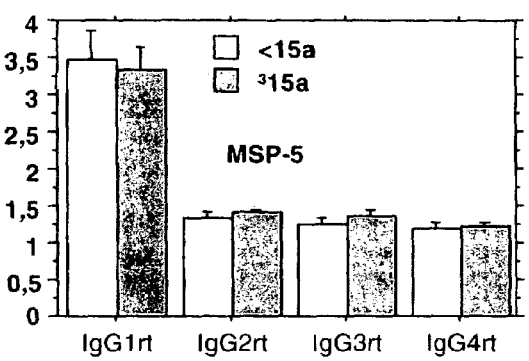

Analysis was limited to a limited number of sera for MSP4-40 and MSP5. The results are shown in FIGS. 25A and 25B. For MSP-p40 the isotype profile was IgG1+, IgG3+ and non-negligible amounts of IgG4:

There is no correlation between titres and recent circulating parasitaemia

IgG3 levels were higher for individuals >15 yrs old (P=0.006) and equal to those who had recently suffered malaria episodes (P=0.03), which is an expected result as accesses is an age related event in endemic area.

IgG1 and IgG3 were significant components of the IgG response, representing 40% and 30% of the IgG respectively.

For the strong responders, there exists a significant relationship between the IgG response and invasion inhibition (IgG subclass independent).

For MSP-5, the isotype profile is predominantly IgG1

There is no difference in relation with recent circulating parasitaemia (close to significance P=0.06) or with age.

IgG1 was a significant main component of the IgG response, totaling 75% of the response.

There was no correlation between IgG response and invasion or growth inhibition (no particular isotype was associated).

(8) Correlation with Malaria Episodes

An age-adjusted Poisson regression model was used to analyze the relationship between Ab responses against the Ag constructs and the incidence of malaria episodes during the follow-up period. These antigens showed a significant association with protection against clinical episodes in the prospective study cohort of 205 individuals from the village of Ndiop (2000).

Concerning MSP4

In agreement with the previously noted observations, where significant differences were seen between IgG titres to MSP4-p40 and MSP4-p30, the Ab responses against the full-length antigen (MSP4-p40) are not associated with protection. However, Ab responses directed to the construct missing the 30 residue variable domain of the antigen (MSP4-p30) and the smallest antigen (MSP4p20) are significantly associated with protection (P<0.05). These findings reinforce the idea that residue polymorphisms at the N-terminal of the protein are involved in immune evasion and that antibodies directed to this region of the protein have (A) limited affinity (B) exhibit strain specificity, thus have limited effect on a majority of strains or/and (C) due the presence of APL never achieve affinity maturation or lack the required T-cell help. Regardless of the mechanisms involved, this data supports the idea that conserved protein subunits have a better chance of inducing broad specificity immunity than full entities, which frequently contain regions of polymorphism believed to function in immune evasion.

| MSP4-40 | Coefficient | Std. Error | p-value | Rate Ratio | Lower (C.I.) | Upper (C.I.) |
|---|---|---|---|---|---|---|
| % GM | −6.049 | 0.1935 | <0.001 | 0.00236 | 0.001615 | 0.003449 |
| AgeCl3 | 1.215 | 0.1021 | <0.001 | 3.37 | 2.759 | 4.116 |
| m4 40cl2 | −0.2279 | 0.1245 | 0.067 | 0.7962 | 0.6238 | 1.016 |

| MSP4-30 | Coefficient | Std. Error | p-value | Rate Ratio | Lower (C.I.) | Upper (C.I.) |
|---|---|---|---|---|---|---|
| % GM | −6.031 | 0.1931 | <0.001 | 0.002403 | 0.001646 | 0.003508 |
| AgeCl3 | 1.218 | 0.1017 | <0.001 | 3.38 | 2.769 | 4.125 |
| M4md cl2 | −0.2546 | 0.1216 | 0.036 | 0.7752 | 0.6108 | 0.9839 |

| MSP4-20 | Coef-ficient | Std. Error | p-value | Rate Ratio | Lower (C.I.) | Upper (C.I.) |
|---|---|---|---|---|---|---|
| % GM | −6.017 | 0.1914 | <0.001 | 0.002438 | 0.001676 | 0.003548 |
| AgeCl3 | 1.216 | 0.1013 | <0.001 | 3.373 | 2.766 | 4.114 |
| m4_20cl2 | −0.2888 | 0.1223 | 0.018 | 0.7491 | 0.5895 | 0.9521 | episodes was found. In view of the fatty acid modification predicted to be carried by the antigen, these results have interesting implications with regards to disease severity and anti-lipid responses.

| MSP5 | Coef-ficient | Std. Error | p-value | Rate Ratio | Lower (C.I.) | Upper (C.I.) |
|---|---|---|---|---|---|---|
| % GM | −5.964 | 0.1917 | <0.001 | 0.00257 | 0.001765 | 0.003741 |
| AgeCl3 | 1.201 | 0.1016 | <0.001 | 3.324 | 2.724 | 4.057 |
| msp5cl2 | −0.3706 | 0.1243 | 0.0028 | 0.6904 | 0.541 | 0.8809 |

The primary conclusions that can be drawn from the above presented data are (1) Baculovirus expressed MSP4 and MSP5 are useful as vaccines with activities in line with those seen for MSP1p19, (2) these antigens are strongly recognized by immune individuals (3) higher than median values of IgG recognition of the conserved domains of MSP4 (p30 and more so p20) and that of the highly conserved MSP5 antigen are correlated with natural protection against clinical malaria.

EXAMPLE 17

MSP4p20 Expression Constructs

Two constructs have been designed from *Plasmodium falciparum* MSP4 synthetic gene sequence for the expression of MSP4p20. One construct is identified as MSP4p21ss1 other named PfMSP4p21ss1 [SEQ ID NO: 28]. The orf [SEQ ID NO:19] encoded by construct MSP4p21ss1 and the predicted amino acid sequence [SEQ ID NO: 20] are described below:

Nucleotide Sequence of Construct MSP4p21 ss1

```
>MSP4p21 ss1
                                              [SEQ ID NO: 28]
ATGTGGATCGTAAAGTTCTTGATTGTGGTCCACTTCTTCATCATATGCAC

CATCAACTTCGACAAGCTCTACATTAGTTACTCTTACAACATCGTCCCTG

AAAACGGACGTATGCTTAACATGAGGATCTTGGGTGAAGAAAAGCCTAAC

GTTGACGGTGTGTCAACATCTctaGAAAAGAGTCCCAAGGAGAGTCAAAT

GGTCGACGACAAGAAGAAGACCGAGGCCATTCCAAAGAAAGTCGTGCAGC

CAAGCTCGAGCAACTCTGGAGGTCACGTCGGTGAAGAAGAAGACCACAAC

GAAGGAGAGGGAGAGCACGAAGAGGAGGAAGAACACGAAGAAGACGATGA

CGACGAGGACGACGACACATACAACAAAGACGACTTGGAGGACGAAGATC

TTTGCAAGCACAACAACGGAGGATGTGGAGATGACAAGCTCTGCGAGTAC

GTTGGAAACCGTCGCGTAAAATGTAAATGTAAGGAAGGATACAAGTTGGA

AGGAATTGAGTGCGTTGAACACCACCACCACCATCACTAA
```

ORF Encoded by Construct MSP4p21 ss1

```
>MSP4p21 ss1
                                              [SEQ ID NO: 19]
MWIVKFLIVVHFFIICTINFDKLYISYSYNIVPENGRMLN

MRIL GEEKPNVDGVSTS EKSPKESQMVDDKKKTEAIPKKVV

QPSSSNSGGHVGEEEDHNEGEGEHEEEEEHEEDDDDEDDD

TYNKDDLEDEDLCKHNNGGCGDDKLCEYVGNRRVKCKCKE

GYKLEGIECVEHHHHHH
```

In light grey: added amino acids directly following the residues MRIL in the sequence of MSP4p40
In dark grey: added amino acid L directly preceding the start of MSP4p20 sequence in the sequence of MSP4p40

Expected Protein Product MSP4p21 ss1

```
                                              [SEQ ID NO: 20]
MRILGEEKPNVDGVSTSLEKSPKESQMVDDKKKTEAIPKKVVQPSSSNSG

GHVGEEEDHNEGEGEHEEEEEHEEDDDDEDDDTYNKDDLEDEDLCKHNNG

GCGDDKLCEYVGNRRVKCKCKEGYKLEGIECVEHHHHHH
```

The other construct is identified as MSP4p21 ss2 other named PfMSP4p21ss2 [SEQ ID NO: 29]. The orf [SEQ ID NO: 21] encoded by construct MSP4p21ss2 and the predicted amino acid sequence [SEQ ID NO: 22] are described herein.

Nucleotide Sequence of Construct MSP4p21 ss2

```
>MSP4p21 ss2
                                              [SEQ ID NO: 29]
ATGTGGATCGTAAAGTTCTTGATTGTGGTCCACTTCTTCATCATATGCAC

CATCAACTTCGACAAGCTCTACATTAGTTACTCTTACAACATCGTCCCTG

AAAACGGACGTATGCTTAACATGAGGATCTTGGGTGAAGAAAAGCCTCTA

GAAAAGAGTCCCAAGGAGAGTCAAATGGTCGACGACAAGAAGAAGACCGA

GGCCATTCCAAAGAAAGTCGTGCAGCCAAGCTCGAGCAACTCTGGAGGTC

ACGTCGGTGAAGAAGAAGACCACAACGAAGGAGAGGGAGAGCACGAAGAG

GAGGAAGAACACGAAGAAGACGATGACGACGAGGACGACGACACATACAA

CAAAGACGACTTGGAGGACGAAGATCTTTGCAAGCACAACAACGGAGGAT

GTGGAGATGACAAGCTCTGCGAGTACGTTGGAAACCGTCGCGTAAAATGT

AAATGTAAGGAAGGATACAAGTTGGAAGGAATTGAGTGCGTTGAACACCA

CCACCACCATCACTAA
```

ORF Encoded by Construct MSP4p21 ss2

```
>MSP4p21 ss2
                                              [SEQ ID NO: 21]
MWIVKFLIVVHFFIICTINFDKLYISYSYNIVPENGRMLN

MRIL GEEKP EKSPKESQMVDDKKKTEAIPKKVVQPSSSN

SGGHVGEEEDHNEGEGEHEEEEEHEEDDDDEDDDTYNKDD

LEDEDLCKHNNGGCGDDKLCEYVGNRRVKCKCKEGYKLEG

IECVEHHHHHH
```

In light grey: added amino acids directly following the cleavage site MRIL in the sequence of MSP4p40
In dark grey: added amino acid L directly preceding the start of MSP4p20 sequence in the sequence of MSP4p40

Expected Protein Product MSP4p21 ss2

[SEQ ID NO: 22]
MRILGEEKPLEKSPKESQMVDDKKKTEAIPKKVVQPSSSNSGGHVGEEED

HNEGEGEHEEEEEHEEDDDDEDDDTYNKDDLEDEDLCKHNNGGCGDDKLC

EYVGNRRVKCKCKEGYKLEGIECVEHHHHHH

EXAMPLE 18

Evolutionary Conservation of MSP4 Features

When the amino acid sequence of MSP4 from *P. falciparum* and *P. vivax* are aligned using a common alignment program (ClustalX) several striking observations can be made. See FIG. 26. Firstly, the residues downstream of the signal sequence cleavage site of *P. falciparum* (as defined here) are nearly 100% conserved between the species (Pf MRILGE (SEQ ID NO: 55) and Pv GRILGE (SEQ ID NO: 56)). This finding once again strongly supports the idea that the mature PfMSP4 protein starts at residue 41 and the residues directly proceeding are part of a conserved cleavage site. Secondly, the sequence element known as SALSA (underlined) is not present in the *P. vivax* protein. This would suggest that hepatocyte binding (if mediated by PfMSP4 in vivo) is not a conserved, thus vital function of this protein. Instead this region of the *P. vivax* protein is completely divergent from that of *P. falciparum* and contains very low complexity sequence. While not visibly comparable to the sequence of *P. falciparum*, one could imagine that the effect on the immune system is similar. In *P. falciparum*, there is an N-terminal hyper-variable region at the extreme N-terminal of the protein. Statistical analysis of polymorphism frequencies indicates two sites within this region that could be involved in immune evasion. This would be achieved through the modification or ablation of B and T cell epitopes leading to strain specific responses and/or immune tolerance when exposed to variant sequences. This type of immune modulation is also a property of repeat sequences. (A) They contain their own altered peptide ligands and (B) they can induce T-cell independent B-cell activation which classically leads to the generation of short lived and low affinity responses. The Third observation that can be made from the aligned sequences is that the primary sequence elements of the MSP4p20 are present in both species. Unsurprisingly, both the core EFG-domain and GPI-attachments signals are conserved, more interestingly the acidic repeats appear to be arranged in a comparable fashion. This lends weight to the idea that in natural infection MSP4 is either degraded or cleaved in a manor that leaves a membrane associated, small structural entity on the surface of the merozoite. Whether this entity will enter the freshly invaded RBC, as seen with MSP1p19, has not yet been confirmed, but the model seems to fit. On the bases of this comparison, the following protein sequence could be proposed as an anti-*P. vivax* malaria vaccine candidate.

EXAMPLE 19

Role of Antibodies to MSP4p20 in Antibody Dependent Phagocytosis of Merozoites by Polymorphonuclear Neutrophils Neutrophils internalize pathogens and destroy them using reactive oxygen species (ROS) and granule hydrolytic proteins. Activated neutrophils are highly effective at generating ROS like $O_2^-$, $H_2O_2$, ..., by a process known as the respiratory burst operating via an NADPH oxydase. ROS can be detected by a chemiluminescence dye and used as a measure of antibody induced phagocytic activity. The chemiluminescence dye is luminol, and in the presence of ROS, it emits light, which is quantified with a luminometer (Microlumat+) linked to a computer.

Using a new functional assay based on antibody dependent phagocytosis of merozoites (ADPm) by polymorphonuclear neutrophils (PMN), phagocytosis of *Plasmodium falciparum* merozoites induced by naturally acquired and vaccination-induced antibodies was measured. Using immune sera from individuals in malaria endemic areas and frozen merozoite preparations, this test was shown to be highly specific, with negligible non-immune background signals, and good intra-assay reproducibility. Inter-assay comparisons are made by using a standard positive control.

Data from individuals living in an area of seasonal transmission showed that ADPm activity was significantly correlated with age and IgG antibody responses to merozoite and MSP recombinant antigens as measured by ELISA. Depletion of antibodies specific for baculovirus recombinant MSP1p19 and MSP4p20 from endemic immune sera of residents of Dielmo and Ndiop villages in Senegal, showed that antibodies against these antigens are substantial components of ADPm activity.

More particularly, *P. falciparum* merozoites were harvested by centrifugation of culture supernatants and stored as frozen aliquots. Polymorpho-nuclear neutrophils, obtained from fresh donated blood, were isolated with a simple Ficoll-Hystopaque 1077 gradient, and used in the ADPm assay immediately. Endemic immune sera were obtained from inhabitants of Ndiop (mesoendemic) and Dielmo (holoendemic). Recombinant MSP1p19 and MSP4p20 antigens with C-terminal hexa-histidine tags (SEQ ID NO: 57) were produced in the baculovirus expression system and purified by immobilized-metalo-affinity chromatography. Sera were depleted of anti-MSP1p19 or/and anti-MSP4p20 antibodies using a TALON metal affinity resin charged with the corresponding recombinant antigens. Merozoites were incubated with sera in 96-well plates before addition of luminol and PMN ($5 \cdot 10^6$ cells per well) to initiate the reaction. Luminescence output was measured for 1 hour using a Berthold MicroLumat Plus 96 wells. A positive standard human immune sera control (HIS) was used to quantify the response:

Antigen-specific IgG opsonisation (binding) of merozoites (with or without the complement) is required for a positive readout in this assay, since decomplemented sera (treatment at 56° C. for 30 minutes) or total IgG purified with protein-G induces a similar response to the initial sera, and serum depleted of total IgG no longer produces a response (FIG. 34). However, the magnitude of the chemiluminescence effect generated by specific IgG is variable. The FIG. 35 shows that antibodies specific for baculovirus MSP4p20 and MSP1p19 are both functional in this assay, but not to the same extent. The chemiluminescence signal is reduced 67% following MSP4p20 antibody depletion, compared to 34% reduction by MSP1p19 antibody depletion. Depletion of antibodies specific for both MSP4p20 and MSP1p19 reduced the chemiluminescence signal by 78%.

These results show that natural antibodies recognizing the baculovirus MSP4p20 and MSP1p19 recombinant proteins are important components mediating merozoite phagocytosis and destruction by PMN immune effectors, strongly supporting the use of these antigens as vaccines.

EXAMPLE 20

PfMSP5 Modification

To look at the nature of the N-terminal blocking modification seen to be present on Baculovirus expressed PfMSP5, radiolabelling experiments were performed. Since mass spectrometry suggested that the entity was a covalently associated myristoyl group, incorporation of Myristoyl was initially examined. Insect cell infections were performed in T25 cell culture flasks using SF9 cells as previously described in Example 1. At 24 h post infection, 200 µCi of $[9,10_{(n)}-^3H]$ Myristic acid (Amersham) in complex with fatty acid free BSA was added to the culture supernatant. At 70 h post infection, culture supernatants were harvested, dialysed against 20 mM Tris pH8; 500 mM NaCl, and batch purified over Talon® resin. On blue stained SDS-PAGE gels, protein expression was seen to be identical for the non-labelled control and the culture performed in the presence of radiolabel. When analysed by autoradiography, both PfMSP5 Baculovirus expressed proteins (35 and 45 kDa) had incorporated the tritiated myristoyl (FIG. 27). No background activity was seen with un-labelled protein, and the two PfMSP5 protein bands were not seen with the null virus infection.

These results show that recombinant PfMSP5 protein expressed in baculovirus is myristoyled. These data confirm the previous data in Examples 4 to 7 related to expression of PfMSP5 in insect cells.

EXAMPLE 21

The Fate of PfMSP4

To follow the natural fate of PfMSP4, several different purified sera were generated. Firstly, a pool of anti-sera collected from 4 MSP4-vaccinated rabbits was affinity purified against NHS-activated sepharose fixed Baculovirus expressed PfMSP4p20. This process was repeated using two different pools of 5 human immune sera known to be positive for PfMSP4 from either Ndiop or Dielmo. Using these antibody reagents, the fate of PfMSP4 was followed by IFA and western blot in the culture adapted strain 3D7 and the finding was compared to those seen with a monoclonal antibody specific for PfMSP1p19 (G17.12). As shown in FIG. 28A, PfMSP4 was detected at the surface of late stage parasites and free merozoites but not in acetone fixed ring stage parasites in which PfMSP1p19 could be identified. In addition, when looking at parallel analysis of equal quantities of parasite extract by western blot (FIG. 28B), PfMSP4 levels seem to be far less on free merozoites collected from parasite culture supernatants than on mature schizonts and the protein is not detected in ring stage parasite extracts. This data is consistent with the idea that PfMSP4 is shed from the merozoite surface in a manner similar to Apical Membrane Antigen-1 rather than being proteolytically processed and carried into the freshly invaded RBC, as seen for MSP1p19.

Interestingly, both affinity-purified sera (rabbit and human) recognise multiple high molecular weight protein bands exclusive to the mature schizont extract. This could be antigens present in the mature schizont that contain cross-reactive epitopes as previously found with MSP3 and MSP6, or, since the parasite extract is not reduced, this could be natural PfMSP4 protein trimers.

To investigate PfMSP4 expression in pre-hepatic stage parasites, IFA was performed on *P. falciparum* sporozoites using anti-PfMSP4p20 affinity purified rabbit sera. While the positive control anti-CSP monoclonal antibody gave strong and clear surface staining, no staining was achieved with the anti-PfMSP4p20 antibodies.

These results show that natural MSP4 protein is localized on merozoite's surface and is no more present upon reinvasion of blood cells by the parasite (see IFA on ring-stage infected blood cells, FIG. 28A). The western blot of FIG. 28B shows identical patterns with antibodies directed against natural MSP4 (human sera) and with antibodies directed against recombinant MSP4 (rabbit sera). So it can be deduced from this that antibodies directed against baculovirus recombinant antigen are able to recognize natural forms of antigen.

EXAMPLE 22

Expression of the p20 Sub-Domain Independently of p40

To facilitate direct expression of the p20 sub-domain, a series of new expression constructs were built (FIG. 29 and Example 17) and tested. As shown in FIG. 30, the construct encoding the minimum signal sequence (PfMSP4p21) did not lead to protein secretion, though high levels of intracellular protein were detected (data not shown). Better levels of expression were achieved with constructs PfMSP4p21ss1 and ss2 and as seen in FIG. 30, and as revealed by N-terminal sequencing (see FIG. 29), both proteins rapidly lose the remaining N-terminal residues to produce the same stable p20 entity that is seen with baculovirus PfMSP4p40. However, when comparing protein expression at 66 h post infection from parallel infections conducted using baculovirus PfMSP4p40 and PfMSP4p21ss1, the original construct leads to far superior protein yields (2-fold). These results complement Example 17, supra.

EXAMPLE 23

Expression of PvMSP4 in the Baculovirus Expression System

To obtain the PvMSP4 open reading frame (ORF), nested PCR was performed on genomic DNA from the parasite strain Belem. As *P. vivax* genomic DNA is around 50% GC rich, it was not necessary to make a synthetic gene. The entire ORF was cloned into pMosBLUE and sequenced. Next, both exons were amplified by PCR with the GPI attachment signal at the 3' end of exon 2 replaced by a hexa-his tag (SEQ ID NO: 57. In addition, a suitable restriction site was introduced at the 3' or 5' end of exon 1 and 2, respectively, and these were sequentially cloned into the pMosBLUE vector to form a continuous ORF ending in a his-tag (FIG. 31).

A PvMSP4 encoding Baculovirus was generated using the standard protocol and protein expression over time was assessed using High Five insect cells as previously described. As shown in FIG. 32, protein expression was detectable at around 30 h post infection.

N-terminal sequence analysis performed on this protein band revealed an N-terminal of GIAAC (SEQ ID NO: 49). Protein expression peaked at around 54 h post infection and at this time point some protein degradation was visible. However, PvMSP4 does not degrade in a manner similar to PfMSP4. N-terminal sequencing of the final product showed that the protein had degraded by 13 or 30-32 amino acids giving the N-terminal sequence of EGGEQ (SEQ ID NO: 50)

and a mixed signal giving GDSSG (SEQ ID NO: 51), DSSGG (SEQ ID NO: 52) and SSGGL (SEQ ID NO: 53). The smallest protein product detected, around 8 kDa in size, carries the N-terminal sequence LDNNG (SEQ ID NO: 54).

EXAMPLE 24

Human Immune Sera Recognition of PvMSP4

At the end of the time course analysis (66 h as shown in FIG. 32) 130 mL of culture supernatant was purified by HPLC over Talon™ resin. The purified product consists of the 30, 25 kDa, and 8 kDa bands seen in FIG. 32.

To look at human sera recognition, ELISA plates were coated with the Baculovirus expressed PvMSP4 at 0.5 µg/mL.

A total of 24 Sera samples collected in Sri Lanka from individuals having experienced at least one episode of *P. vivax* malaria, were tested in parallel. Seventeen of these samples were sera positive for PvMSP4 with end-point titre of between 1/25,000 and 1/200,000 (FIG. 33A). These seventeen positive sera were tested at 1/2700 dilution on ELISA plates coated with baculovirus PvMSP4 irreversibly reduced by treatment with DTT and iodoacetamide. Of the 17 positive sera, 11 showed a degree of reduction sensitivity ranging from 12-80% whether calculated at a fixed dilution of 1/2700 or using the dilution falling in the mid point of each curve (FIG. 33B).

Examples 23 and 24, relating to *Plasmodium vivax* MSP4 (PvMSP4), complement Example 18. As shown in FIG. 33B, while sera No 2, 3, 4, 6, 7, 8, 9, 10, 11, 14, and 17 have less affinity for DTT-reduced antigen than for non-reduced antigen, sera Nos. 12 and 15 have a better affinity for reduced antigen than for the non-reduced one. It can be concluded that antigen conformation affects antibody-antigen binding, but, the protective capacity of each of the tested sera against a *Plasmodium* infection being not established, antibodies affinity for reduced or non-reduced antigen can not be correlated with the protective value of the two types of antibody.

The following PfMSP5/His, PfMSP4p30/His and PfMSP4p40/His baculovirus were deposited at the Collection Nationale de Cultures de Microorganismes (C.N.C.M.), of Institut Pasteur, 28, rue du Docteur Roux, 75724 Paris, Cedex 15, FRANCE, on Nov. 10, 2005, and assigned the following Accession Nos.

| MATERIAL | ACCESSION NO. |
|---|---|
| PfMSP5/His | I-3512 |
| PfMSP4p30/His | I-3513 |
| PfMSP4p40/His | I-3514 |

The following F12-7, G21-2, J18-14 and L11-6 hybridomas were deposited at the Collection Nationale de Cultures de Microorganismes (C.N.C.M.), of Institut Pasteur, 28, rue du Docteur Roux, 75724 Paris, Cedex 15, FRANCE, on Nov. 16, 2005, and assigned the following Accession Nos.

| MATERIAL | ACCESSION NO. |
|---|---|
| F12-7 | I-3517 |
| G21-2 | I-3518 |
| J18-14 | I-3519 |
| L11-16 | I-3520 |

The following PfMSP4p21ss1/His, PfMSP4p21ss2/His, and PvMSP4/His were deposited at the Collection Nationale de Cultures de Microorganismes (C.N.C.M.), of Institut Pasteur, 28, rue du Docteur Roux, 75724 Paris, Cedex 15, FRANCE, on Nov. 21, 2006, and assigned the following Accession Nos.

| MATERIAL | ACCESSION NO. |
|---|---|
| PfMSP4p21ss1/His | I-3695 |
| PfMSP4p21ss2/His | I-3696 |
| PvMSP4/His | I-3694 |

Following are amino acid and nucleic acid sequences of peptides and polynucleotides described, supra:

```
MSP5p10 (breakdown product of MSP5, residue
186-253)
YNKVEKNVTDEMLLYNMMSDQNRKSCAINNGGCSDDQICININNIGVKCI

CKDGYLLGTKCIHHHHHH (SEQ ID NO: 15)

Nucleic acid sequence encoding MSP5p10
>readseq-48009_tmp_1 207 bp
TACAACAAGGTCGAGAAGAACGTAACCGACGAGATGCTCTTGTACAACAT

GATGTCCGACCAAAACCGCAAAAGCTGTGCTATCAACAACGGTGGCTGCA

GTGACGACCAGATCTGCATCAACATCAACAACATCGGTGTGAAGTGCATT

TGTAAGGATGGATACCTACTTGGTACCAAGTGCATTCACCACCAGCACCA

CCACTGA (SEQ ID NO: 5)

SEQ ID NO: 1 = nucleic acid encoding breakdown
product MSP4p20 of SEQ ID NO: 9 (residue 132-251)
>readseq-41112_tmp_1 363 bp
AAGAGTCCCAAGGAGAGTCAAATGGTCGACGACAAGAAGAAGACCGAGGC

CATTCCAAAGAAAGTCGTGCAGCCAAGCTCGAGCAACTCTGGAGGTCACG

TCGGTGAAGAAGAAGACCACAACGAAGGAGAGGGAGAGCACGAAGAGGAG

GAAGAACACGAAGAAGACGATGACGACGAGGACGACGACACATACAACAA

AGACGACTTGGAGGACGAAGATCTTTGCAAGCACAACAACGGAGGATGTG

GAGATGACAAGCTCTGCGAGTACGTTGGAAACCGTCGCGTAAAATGTAAA

TGTAAGGAAGGATACAAGTTGGAAGGAATTGAGTGCGTTGAACACCACCA

CCACCATCACTAA (SEQ ID NO: 1)

MSP5
>readseq.input(1), 762 bases, 6761DE71 checksum.
ATGAACATTCTCTGTATTCTCAGCTACATTTACTTCTTCGTCATCTTCTA

CAGTTTAAACCTCAACAACAAAAACGAGAACTTCTTGGTGGTCCGCAGAC

TCATGAACGACGAAAAGGGAGAAGGTGGCTTCACTAGTAAGAACAAGGAA

AACGGAAACAACAACAGGAACAACGAGAACGAACTCAAAGAAGAAGGATC

TTTGCCCACTAAGATGAACGAGAAAACAGTAACTCCGCGGATAAGCAAC

CAAACGACATCTCCCACGACGAAAGCAAGAGCAACAGTAACAACGCCCAA

AACATCCAAAAGGAACCTGAAGAGAAGGAAAACTCAAACCCCAACCTCGA

CTCGAGTGAAAACTCCGCTGAAAGTGCTACTAGAAGCGTCGACATCAGTG

AACACAACTCAAACAACCCCGAAACTAAAGAAGAAAACGGAGAAGAACCT

CTAGACCTGGAAATTAACGAAAACGCAGAAATCGGCCAGGAACCTCCAAA
```

CCGTCTTCACTTCGACAACGTTGACGACGAAGTACCACATTACTCAGGCC

TGAGGTACAACAAGGTCGAGAAGAACGTAACCGACGAGATGCTCTTGTAC

AACATGATGTCCGACCAAAACCGCAAAAGCTGTGCTATCAACAACGGTGG

CTGCAGTGACGACCAGATCTGCATCAACATCAACAACATCGGTGTGAAGT

GCATTTGTAAGGATGGATACCTACTTGGTACCAAGTGCATTCACCACCAC

CACCACCACTGA (SEQ ID NO: 4)

PROTEIN ENCODED BY OAF
>readseq.input(1), 253 bases, 7870B947 checksum.
MNILCILSYIYFFVIFYSLNLNNKNENFLVVRRLMNDEKGEGGFTSKNKE

NGNNNRNNENELKEEGSLPTKMNEKNSNSADKQPNDISHDESKSNSNNAQ

NIQKEPEEKENSNPNLDSSENSAESATRSVDISEHNSNNPETKEENGEEP

LDLEINENAEIGQEPPNRLHFDNVDDEVPHYSALRYNKVEKNVTDEMLLY

NMMSDQNRKSCAINNGGCSDDQICININNIGVKCICKDGYLLGTKCIHHH

HHH (SEQ ID NO: 14)

MSP4p40
>readseq.input(1), 756 bases, 733F5E48 checksum.
ATGTGGATCGTAAAGTTCTTGATTGTGGTCCACTTCTTCATCATATGCAC

CATCAACTTCGACAAGCTCTACATTAGTTACTCTTACAACATCGTCCCTG

AAAACGGACGTATGCTTAACATGAGGATCTTGGGTGAAGAAAAGCCTAAC

GTTGACGGTGTGTCAACATCTAACACACCTGGCGGAAACGAGGCATCTAG

TGCTTCTCCTAACCTTGCTGACGCTGCAGAAAAGAAGGACGAAAAGGAAG

CAAGCGAGCAAGGCGAAGAATCCCACAAGAAGGAAAACTCTCAGGAATCT

GCAAACGGAAAAGACGACGTTAAGGAGGAGAAGAAGACCAACGAGAAGAA

GGACGACGGAAAGACTGACAAGGTACAAGAAAAGGTTCTAGAAAAGAGTC

CCAAGGAGAGTCAAATGGTCGACGACAAGAAGAAGACCGAGGCCATTCCA

AAGAAAGTCGTGCAGCCAAGCTCGAGCAACTCTGGAGGTCACGTCGGTGA

AGAAGAAGACCACAACGAAGGAGAGGGAGAGCACGAAGAGGAGGAAGAAC

ACGAAGAAGACGATGACGACGAGGACGACGACACATACAACAAAGACGAC

TTGGAGGACGAAGATCTTTGCAAGCACAACAACGGAGGATGTGGAGATGA

CAAGCTCTGCGAGTACGTTGGAAACCGTCGCGTAAAATGTAAATGTAAGG

AAGGATACAAGTTGGAAGGAATTGAGTGCGTTGAACACOACCACCACCAT

CACTAA (SEQ ID NO: 3)

PROTEIN ENCODED BY ORF
>readseq.input(1), 251 bases, 1EFAEF35 checksum.
MWIVKFLIVVHFFIICTINFDKLYISYSYNIVPENGRMLNMRILGEEKPN

VDGVSTSNTPGGNEASSASPNLADAAEKKDKEASEQGEESHKKENSQES

ANGKDDVKEEKKTNEKKDDGKTDKVQEKVLEKSPKESQMVDDKKKTEAIP

KKVVQPSSSNSGGHVGEEEDHNEGEGEHEEEEHEEDDDDEDDDTYNKDD

LEDEDLCKHNNGGCGDDKLCEYVGNRRVKCKCKEGYKLEGIECVEHHHH

H (SEQ ID NO: 12)

FINAL PRODUCED PROTEIN
>readseq.input(1), 211 bases, 67EAFE8C checksum.
MRILGEEKPNVDGVSTSNTPGGNEASSASPNLADAAEKKDKEASEQGEE

SHKKENSQESANGKDDVKEEKKTNEKKDDGKTDKVQEKVLEKSPKESQMV

DDKKKTEAIPKKVVQPSSSNSGGHVGEEEDHNEGEGEHEEEEHEEDDDD

EDDDTYNKDDLEDEDLCKHNNGGCGDDKLCEYVGNRRVKCKCKEGYKLEG

IECVEHHHHHH (SEQ ID NO: 13)

P20 PROTEIN secreted with the FINAL PRODUCED
PROTEIN
>readseq.input(1), 120 bases, 9358BD28 checksum.
KSPKESQMVDDKKKTEAIPKKVVQPSSSNSGGHVGEEEDHNEGEGEHEEE

EEHEEDDDDEDDDTYNKDDLEDEDLCKHNNGGCGDDKLCEYVGNRRVKCK

CKEGYKLEGIECVEHHHHHH (SEQ ID NO: 9)

MSP4p30
>readseq.input(1), 666 bases, A9B2DCBC checksum.
ATGTGGATCGTAAAGTTCTTGATTGTGGTCCACTTCTTCATCATATGCAC

CATCAACTTCGACAAGCTCTACATTAGTTACTCTTACAACATCGTCCCTG

AAAACGGACGTATGCTTAACATGAGGATCTTGGCTGCAGAAAAGAAGGAC

GAAAAGGAAGCAAGCGAGCAAGGCGAAGAATCCCACAAGAAGGAAAACTC

TCAGGAATCTGCAAACGGAAAAGACGACGTTAAGGAGGAGAAGAAGACCA

ACGAGAAGAAGGACGACGGAAAGACTGACAAGGTACAAGAAAAGGTTCTA

GAAAAGAGTCCCAAGGAGAGTCAAATGGTCGACGACAAGAAGAAGACCGA

GGCCATTCCAAAGAAAGTCGTGCAGCCAAGCTCGAGCAACTCTGGAGGTC

ACGTCGGTGAAGAAGAAGACCACAACGAAGGAGGGAGAGCACGAAGAG

GAGGAAGAACACGAAGAAGACGATGACGACGAGGACGACGACACATACAA

CAAAGACGACTTGGAGGACGAAGATCTTTGCAAGCACAACAACGGAGGAT

GTGGAGATGACAAGCTCTGCGAGTACGTTGGAAACCGTCGCGTAAAATGT

AAATGTAAGGAAGGATACAAGTTGGAAGGAATTGAGTGCGTTGAACACCA

CCACCACCATCACTAA (SEQ ID NO: 2)

PROTEIN ENCODED BY ORF
>readseq.input(1), 221 bases, F982D7F0 checksum.
MWIVKFLIVVHFFIICTINFDKLYISYSYNIVPENGRMLNMRILAAEKKD

EKEASEQGEESHKKENSQESANGKDDVKEEKKTNEKKDDGKTDKVQEKVL

EKSPKESQMVDDKKKTEAIPKKVVQPSSSNSGGHVGEEEDHNEGEGEHEE

EEHEEDDDDEDDDTYNKDDLEDEDLCKHNNGGCGDDKLCEYVGNRRVKC

KCKEGYKLEGIECVEHHHHHH (SEQ ID NO: 10)

FINAL PRODUCED PROTEIN
>readseq.input(1), 181 bases, FB2C49DD checksum.
MRILAAEKKDEKEASEQGEESHKKENSQESANGKDDVKEEKKTNEKKDDG

KTDKVQEKVLEKSPKESQMVDDKKKTEAIPKKVVQPSSSNSGGHVGEEED

HNEGEGEHEEEEHEEDDDDEDDDTYNKDDLEDEDLCKHNNGGCGDDKLC

EYVGNRRVKCKCKEGYKLEGIECVEHHHHHH (SEQ ID NO: 11)

MSP4p21
>readseq.input(1), 498 bases, C2453A47 checksum.
ATGTGGATCGTAAAGTTCTTGATTGTGGTCCACTTCTTCATCATATGCAC

CATCAACTTCGACAAGCTCTACATTAGTTACTCTTACAACATCGTCCCTG

AAAACGGACGTATGCTTAACATGAGGATTCTAGAAAAGAGTCCCAAGGAG

AGTCAAATGGTCGACGACAAGAAGAAGACCGAGGCCATTCCAAAGAAAGT

CGTGCAGCCAAGCTCGAGCAACTCTGGAGGTCACGTCGGTGAAGAAGAAG

ACCACAACGAAGGAGGGAGAGCACGAAGAGGAGGAAGAACACGAAGAA

```
GACGATGACGACGAGGACGACGACACATACAACAAAGACGACTTGGAGGA

CGAAGATCTTTGCAAGCACAACAACGGAGGATGTGGAGATGACAAGCTCT

GCGAGTACGTTGGAAACCGTCGCGTAAAATGTAAATGTAAGGAAGGATAC

AAGTTGGAAGGAATTGAGTGCGTTGAACACCACCACCACCATCACTAA
  (SEQ ID NO: 6)

PROTEIN ENCODED BY ORF
>readseq.input(1), 165 bases, 27BB4F2E checksum.
MWIVKFLIVVHFFIICTINFDKLYISYSYNIVPENGRMLNMRILEKSPKE

SQMVDDKKKTEAIPKKVVQPSSSNSGGHVGEEEDHNEGEGEHEEEEEHEE

DDDDEDDDTYNKDDLEDEDLCKHNNGGCGDDKLCEYVGNRRVKCKCKEGY

KLEGIECVEHHHHHH (SEQ ID NO: 17)

FINAL PRODUCED PROTEIN
readseq.input(1), 125 bases, 50D64DD2 checksum.
MRILEKSPKESQMVDDKKKTEAIPKKVVQPSSSNSGGHVGEEEDHNEGEG

EHEEEEEHEEDDDDEDDDTYNKDDLEDEDLCKHNNGGCGDDKLCEYVGNR

RVKCKCKEGYKLEGIECVEHHHHHH (SEQ ID NO: 18)

MSP4p21 ss1
>readseq.input(1), 540 bases, 96DADE5 checksum.
ATGTGGATCGTAAAGTTCTTGATTGTGGTCCACTTCTTCATCATATGCAC

CATCAACTTCGACAAGCTCTACATTAGTTACTCTTACAACATCGTCCCTG

AAAACGGACGTATGCTTAACATGAGGATCTTGGGTGAAGAAAAGCCTAAC

GTTGACGGTGTGTCAACATCTctaGAAAAGAGTCCCAAGGAGAGTCAAAT

GGTCGACGACAAGAAGAAGACCGAGGCCATTCCAAAGAAAGTCGTGCAGC

CAAGCTCGAGCAACTCTGGAGGTCACGTCGGTGAAGAAGAAGACCACAAC

GAAGGAGAGGGAGAGCACGAAGAGGAGGAAGAACACGAAGAAGACGATGA

CGACGAGGACGACGACACATACAACAAAGACGACTTGGAGGACGAAGATC

TTTGCAAGCACAACAACGGAGGATGTGGAGATGACAAGCTCTGCGAGTAC

GTTGGAAACCGTCGCGTAAAATGTAAATGTAAGGAAGGATACAAGTTGGA

AGGAATTGAGTGCGTTGAACACCACCACCACCATCACTAA
  (SEQ ID NO: 7)

PROTEIN ENCODED BY ORF
>readseq.input(1), 179 bases, F0D6C58 checksum.
MWIVKFLIVVHFFIICTINFDKLYISYSYNIVPENGRMLNMRILGEEKPN

VDGVSTSLEKSPKESQMVDDKKKTEAIPKKVVQPSSSNSGGHVGEEEDHN

EGEGEHEEEEHEEDDDDEDDDTYNKDDLEDEDLCKHNNGGCGDDKLCEY

VGNRRVKCKCKEGYKLEGIECVEHHHHHH (SEQ ID NO: 19)

FINAL PRODUCED PROTEIN
>readseq.input(1), 139 bases, 4D5C3E0F checksum.
MRILGEEKPNVDGVSTSLEKSPKESQMVDDKKKTEAIPKKVVQPSSSNSG

GHVGEEEDHNEGEGEHEEEEHEEDDDDEDDDTYNKDDLEDEDLCKHNNG

GCGDDKLCEYVGNRRVKCKCKEGYKLEGIECVEHHHHHH
  (SEQ ID NO: 20)

MSP4p21 ss2
>readseq.input(1), 516 bases, 1B3CABBA checksum.
ATGTGGATCGTAAAGTTCTTGATTGTGGTCCACTTCTTCATCATATGCAC

CATCAACTTCGACAAGCTCTACATTAGTTACTCTTACAACATCGTCCCTG

AAAACGGACGTATGCTTAACATGAGGATCTTGGGTGAAGAAAAGCCTCTA

GAAAAGAGTCCCAAGGAGAGTCAAATGGTCGACGACAAGAAGAAGACCGA

GGCCATTCCAAAGAAAGTCGTGCAGCCAAGCTCGAGCAACTCTGGAGGTC

ACGTCGGTGAAGAAGAAGACCACAACGAAGGAGAGGGAGAGCACGAAGAG

GAGGAAGAACACGAAGAAGACGATGACGACGAGGACGACGACACATACAA

CAAAGACGACTTGGAGGACGAAGATCTTTGCAAGCACAACAACGGAGGAT

GTGGAGATGACAAGCTCTGCGAGTACGTTGGAAACCGTCGCGTAAAATGT

AAATGTAAGGAAGGATACAAGTTGGAAGGAATTGAGTGCGTTGAACACCA

CCACCACCATCACTAA (SEQ ID NO: 8)

EXPECTED PROTEIN ENCODED BY ORF
>readseq.input(1), 171 bases, EB09D214 checksum.
MWIVKFLIVVHFFIICTINFDKLYISYSYNIVPENGRMLNMRILGEEKPL

EKSPKESQMVDDKKKTEAIPKKVVQPSSSNSGGHVGEEEDHNEGEGEHEE

EEEHEEDDDDEDDDTYNKDDLEDEDLCKHNNGGCGDDKLCEYVGNRRVKC

KCKEGYKLEGIECVEHHHHHH (SEQ ID NO: 21)

FINAL PRODUCED PROTEIN
>readseq.input(1), 131 bases, 6B6B091D checksum.
MRILGEEKPLEKSPKESQMVDDKKKTEAIPKKVVQPSSSNSGGHVGEEED

HNEGEGEHEEEEHEEDDDDEDDDTYNKDDLEDEDLCKHNNGGCGDDKLC

EYVGNRRVKCKCKEGYKLEGIECVEHHHHHH (SEQ ID NO: 22)
```

REFERENCES

The entire disclosures of each of the following publications are relied upon and incorporated by reference herein.

1. Genton, B., Al-Yaman, F., Betuela, I. et al. Safety and immunogenicity of a three-component blood-stage malaria vaccine (MSP1, MSP2, RESA) against *Plasmodium falciparum* in Papua New Guinean children. *Vaccine* 2003, 22(1), 30-41.
2. Stowers, A. W., Kennedy, M. C., Keegan, B. P., Saul, A., Long, C. A. & Miller, L. H. Vaccination of monkeys with recombinant *Plasmodium falciparum* apical membrane antigen 1 confers protection against blood-stage malaria. *Infect Immun* 2002, 70(12), 6961-6967.
3. O'Donnell, R. A., de Koning-Ward, T. F., Burt, R. A. et al. Antibodies against merozoite surface protein (MSP)-1 (19) are a major component of the invasion-inhibitory response in individuals immune to malaria. *J Exp Med* 2001, 193 (12), 1403-1412.
4. Hughes, M. K. & Hughes, A. L. Natural selection on *Plasmodium* surface proteins. *Mol Biochem Parasitol* 1995, 71 (1), 99-113.
5. Escalante, A. A., Lal, A. A. & Ayala, F. J. Genetic polymorphism and natural selection in the malaria parasite *Plasmodium falciparum*. *Genetics* 1998, 149(1), 189-202.
6. Volkman, S. K., Hartl, D. L., Wirth, D. F. et al. Excess polymorphisms in genes for membrane proteins in *Plasmodium falciparum*. *Science* 2002, 298(5591), 216-218.
7. Rayner, J. C., Corredor, V., Feldman, D. et al. Extensive polymorphism in the *Plasmodium vivax* merozoite surface coat protein MSP-3alpha is limited to specific domains. *Parasitology* 2002, 125(Pt 5), 393-405.
8. Taylor, R. R., Smith, D. B., Robinson, V. J., McBride, J. S. & Riley, E. M. Human antibody response to *Plasmodium falciparum* merozoite surface protein 2 is serogroup specific and predominantly of the immunoglobulin G3 subclass. *Infect Immun* 1995, 63(11), 4382-4388.
9. Wang, L., Mohandas, N., Thomas, A. & Coppel, R. L. Detection of detergent-resistant membranes in asexual blood-stage parasites of *Plasmodium falciparum*. *Mol Biochem Parasitol* 2003, 130(2), 149-153.
10. Marshall, V. M., Silva, A., Foley, M. et al. A second merozoite surface protein (MSP-4) of *Plasmodium falciparum* that contains an epidermal growth factor-like domain. *Infect Immun* 1997, 65(11), 4460-4467.
11. Wu, T., Black, C. G., Wang, L., Hibbs, A. R. & Coppel, R. L. Lack of sequence diversity in the gene encoding merozoite surface protein 5 of *Plasmodium falciparum*. *Mol Biochem Parasitol* 1999, 103(2), 243-250.
12. Wang, L., Black, C. G., Marshall, V. M. & Coppel, R. L. Structural and antigenic properties of merozoite surface protein 4 of *Plasmodium falciparum*. *Infect Immun* 1999, 67(5), 2193-2200.
13. Wang, L., Richie, T. L., Stowers, A., Nhan, D. H. & Coppel, R. L. Naturally acquired antibody responses to *Plasmodium falciparum* merozoite surface protein 4 in a population living in an area of endemicity in Vietnam. *Infect Immun* 2001, 69(7), 4390-4397.
14. Black, C. G., Wang, L., Hibbs, A. R., Werner, E. & Coppel, R. L. Identification of the *Plasmodium chabaudi* homologue of merozoite surface proteins 4 and 5 of *Plasmodium falciparum*. *Infect Immun* 1999, 67(5), 2075-2081.
15. Black, C. G. & Coppel, R. L. Synonymous and non-synonymous mutations in a region of the *Plasmodium chabaudi* genome and evidence for selection acting on a malaria vaccine candidate. *Mol Biochem Parasitol* 2000, 111 (2), 447-451.
16. Kedzierski, L. Black, C. G. & Coppel, R. L. Characterization of the merozoite surface protein 4/5 gene of *Plasmodium berghei* and *Plasmodium yoelii*. *Mol Biochem Parasitol* 2000, 105(1), 137-147.
17. Kedzierski, L., Black, C. G., Goschnick, M. W., Stowers, A. W. & Coppel, R. L. Immunization with a Combination of Merozoite Surface Proteins 4/5 and 1 Enhances Protection against Lethal Challenge with *Plasmodium yoelii*. *Infect Immun* 2002, 70(12), 6606-6613.
18. Kedzierski, L., Black, C. G. & Coppel, R. L. Immunization with recombinant *Plasmodium yoelii* merozoite surface protein 4/5 protects mice against lethal challenge. *Infect Immun* 2000, 68(10), 6034-6037.
19. Kedzierski, L., Black, C. G., Stowers, A. W., Goschnick, M. W., Kaslow, D. C. & Coppel, R. L. Comparison of the protective efficacy of yeast-derived and *Escherichia coli*-derived recombinant merozoite surface protein 4/5 against lethal challenge by *Plasmodium yoelii*. *Vaccine* 2001, 19(32), 4661-4668.
20. Wang, L., Goschnick, M. W. & Coppel, R. L. Oral Immunization with a Combination of *Plasmodium yoelii* Merozoite Surface Proteins 1 and 4/5 Enhances Protection against Lethal Malaria Challenge. *Infect Immun* 2004, 72(10), 6172-6175.
21. Goschnick, M. W., Black, C. G., Kedzierski, L., Holder, A. A. & Coppel, R. L. Merozoite Surface Protein 4/5 Provides Protection against Lethal Challenge with a Heterologous Malaria Parasite Strain. *Infect Immun* 2004, 72(10), 5840-5849.
22. Marshall, V. M., Tieqiao, W. & Coppel, R. L. Close linkage of three merozoite surface protein genes on chromosome 2 of *Plasmodium falciparum*. *Mol Biochem Parasitol* 1998, 94(1), 13-25.
23. Nishimura, Y., Chen, Y. Z., Uemura, Y. et al. Degenerate recognition and response of human CD4+ Th cell clones: implications for basic and applied immunology. *Mol Immunol* 2004, 40(14-15), 1089-1094.
24. Brady, C. P., Shimp, R. L., Miles, A. P., Whitmore, M. & Stowers, A. W. High-level production and purification of P30P2MSP1 (19), an important vaccine antigen for malaria, expressed in the methylotropic yeast *Pichia pastoris*. *Protein Expr Purif* 2001, 23(3), 468-475.
25. Epp, C., Kauth, C. W., Bujard, H. & Lutz, R. Expression and purification of *Plasmodium falciparum* MSP-1 (42): A malaria vaccine candidate. *J Chromatogr B Analyt Technol Biomed Life Sci* 2003, 786(1-2), 61-72.
26. Withers-Martinez, C., Saldanha, J. W., Ely, B. et al. Expression of recombinant *Plasmodium falciparum* subtilisin-like protease-1 in insect cells. Characterization, comparison with the parasite protease, and homology modeling PCR-based gene synthesis as an efficient approach for expression of the A+T-rich malaria genome. *J Biol Chem* 2002, 277(33), 29698-29709. Epub 22002 June 29696.
27. Zhou, Z., Schnake, P., Xiao, L. & Lal, A. A. Enhanced expression of a recombinant malaria candidate vaccine in *Escherichia coli* by codon optimization. *Protein Expr Purif* 2004, 34(1), 87-94.
28. Weber, J. L. Molecular Biology of Malaria Parasites. *Exp. Parasitol.* 1988, 66, 143-170.
29. Withers-Martinez, C., Carpenter, E. P., Hackett, F. et al. PCR-based gene synthesis as an efficient approach for expression of the A+T-rich malaria genome. *Protein Eng* 1999, 12(12), 1113-1120.
30. Ballou, W. R., Arevalo-Herrera, M., Carucci, D. et al. Update on the clinical development of candidate malaria vaccines. *Am J Trop Med Hyg* 2004, 71(2 Suppl), 239-247.
31. Wang, L., Marshall, V. M. & Coppel, R. L. Limited polymorphism of the vaccine candidate merozoite surface protein 4 of *Plasmodium falciparum*. *Mol Biochem Parasitol* 2002, 120(2), 301-303.
32. Jongwutiwes, S., Putaporntip, C., Friedman, R. & Hughes, A. L. The Extent of Nucleotide Polymorphism is Highly Variable Across a 3-kb Region on *Plasmodium falciparum* Chromosome 2. *Mol Biol Evol* 2002, 19(9), 1585-1590.
33. Polson, H. E., Conway, D. J., Fandeur, T., Mercereau-Puijalon, O. & Longacre, S. Gene polymorphism of *Plasmodium falciparum* merozoite surface proteins 4 and 5. *Mol Biochem Parasitol* 2005, 142(1), 110-115.
34. Puentes, A. G., J. Vera, R. Oopez, R. Suarez, J. Rodriguez, L. Curtidor, H. Sporozoite and Liver Stage Antigen *Plasmodium falciparum* peptides bind specifically to human hepatocytes. *Vaccine* 2004, 22, 1150-1156.
35. Hale, R. S. & Thompson, G. Codon optimization of the gene encoding a domain from human type 1 neurofibromin protein results in a threefold improvement in expression level in *Escherichia coli*. *Protein Expr Purif* 1998, 12(2), 185-188.
36. Longacre, S., Mendis, K. N. & David, P. H. *Plasmodium vivax* merozoite surface protein 1 C-terminal recombinant proteins in baculovirus. *Mol Biochem Parasitol* 1994, 64(2), 191-205.
37. Nacer, A., Berry, L., Slomianny, C. & Mattei, D. *Plasmodium falciparum* signal sequences: simply sequences or special signals? *Int J Parasitol* 2001, 31(12), 1371-1379.
38. Utsumi, T., Nakano, K., Funakoshi, T. et al. Vertical-scanning mutagenesis of amino acids in a model N-myristoylation motif reveals the major amino-terminal sequence requirements for protein N-myristoylation. *Eur J Biochem* 2004, 271(4), 863-874.
39. Resh, M. D. Fatty acylation of proteins: new insights into membrane targeting of myristoylated and palmitoylated proteins. *Biochim Biophys Acta* 1999, 1451(1), 1-16.

40. Gunaratne, R. S., Sajid, M., Ling, I. T., Tripathi, R., Pachebat, J. A. & Holder, A. A. Characterization of N-myristoyltransferase from *Plasmodium falciparum*. *Biochem J* 2000, 348 Pt 2, 459-463.
41. Price, H. P., Menon, M. R., Panethymitaki, C., Goulding, D., McKean, P. G. & Smith, D. F. Myristoyl-CoA:protein N-myristoyltransferase, an essential enzyme and potential drug target in kinetoplastid parasites. *J Biol Chem* 2003, 278(9), 7206-7214.
42. Stafford, W. H., Stockley, R. W., Ludbrook, S. B. & Holder, A. A. Isolation, expression and characterization of the gene for an ADP-ribosylation factor from the human malaria parasite, *Plasmodium falciparum*. *Eur J Biochem* 1996, 242(1), 104-113.
43. Stevenson, F. T., Bursten, S. L., Locksley, R. M. & Lovett, D. H. Myristyl acylation of the tumor necrosis factor alpha precursor on specific lysine residues. *J Exp Med* 1992, 176(4), 1053-1062.
44. Farazi, T. A., Waksman, G. & Gordon, J. I. The biology and enzymology of protein N-myristoylation. *J Biol Chem* 2001, 276(43), 39501-39504.
45. Hayashi, N., Nakagawa, C., Ito, Y. et al. Myristoylation-regulated direct interaction between calcium-bound calmodulin and N-terminal region of pp60v-src. *J Mol Biol* 2004, 338(1), 169-180.
46. Maekawa, S., Matsuura, Y. & Nakamura, S. Expression and myristoylation of NAP-22 using a baculovirus transfer vector system. *Biochim Biophys Acta* 1994, 1218(1), 119-122.
47. Perraut, R., Marrama, L., Diouf, B. et al. Distinct surrogate markers for protection against *Plasmodium falciparum* infection and clinical malaria identified in a Senegalese community after radical drug cure. *J Infect Dis* 2003, 188(12), 1940-1950.
48. Schofield, L., Hewitt, M. C., Evans, K., Siomos, M. A. & Seeberger, P. H. Synthetic GPI as a candidate anti-toxic vaccine, in a model of malaria. *Nature* 2002, 418(6899), 785-789.

What is claimed is:

1. A purified nucleic acid molecule comprising SEQ ID NO: 7.

2. A purified nucleic acid molecule encoding an amino acid sequence comprising SEQ ID NO: 19 or 20.

3. A recombinant vector that directs the expression of the nucleic acid molecule of claim 1 or 2.

4. An isolated host cell transfected, transduced or infected with the vector of claim 3.

5. A recombinant baculovirus deposited at the Collection Nationale de Cultures de Microorganismes (C.N.C.M.) under Accession No. I-3695.

6. A purified nucleic acid molecule consisting of SEQ ID NO: 7.

7. A purified nucleic acid molecule encoding an amino acid sequence consisting of SEQ ID NO: 19.

8. A purified nucleic acid molecule encoding an amino acid sequence consisting of SEQ ID NO: 20.

9. A method of producing a recombinant polypeptide comprising the amino acid sequence of SEQ ID NO: 19 or SEQ ID NO: 20 comprising culturing the host cell of claim 4 in a culture medium under conditions that promote expression of said polypeptide and recovering the polypeptide from the culture medium.

10. A recombinant vector that directs the expression of the nucleic acid molecule of claim 6, 7 or 8.

11. An isolated host cell transfected, transduced or infected with the vector of claim 10.

* * * * *

UNITED STATES PATENT AND TRADEMARK OFFICE
CERTIFICATE OF CORRECTION

PATENT NO.        : 8,026,354 B2
APPLICATION NO.   : 11/603310
DATED             : September 27, 2011
INVENTOR(S)       : Shirley Longacre et al.

Page 1 of 1

It is certified that error appears in the above-identified patent and that said Letters Patent is hereby corrected as shown below:

Title page, item (75), lines 1-3, inventors:
"Hannah Polson, Paris (FR); Ronald Perraut, ointe a Pitre Cedex (FR);"
should read -- Hannah Polson, London (GB); Ronald Perraut, Abymes Cedex (FR); --.

Signed and Sealed this
Twenty-ninth Day of November, 2011

David J. Kappos
*Director of the United States Patent and Trademark Office*

SEQUENCE LISTING

<160> NUMBER OF SEQ ID NOS: 57

<210> SEQ ID NO 1
<211> LENGTH: 363
<212> TYPE: DNA
<213> ORGANISM: Plasmodium falciparum

<400> SEQUENCE: 1

```
aagagtccca aggagagtca aatggtcgac gacaagaaga agaccgaggc cattccaaag      60
aaagtcgtgc agccaagctc gagcaactct ggaggtcacg tcggtgaaga agaagaccac     120
aacgaaggag agggagagca cgaagaggag gaagaacacg aagaagacga tgacgacgag     180
gacgacgaca catacaacaa agacgacttg gaggacgaag atctttgcaa gcacaacaac     240
ggaggatgtg gagatgacaa gctctgcgag tacgttggaa accgtcgcgt aaaatgtaaa     300
tgtaaggaag gatacaagtt ggaaggaatt gagtgcgttg aacaccacca ccaccatcac     360
taa                                                                   363
```

<210> SEQ ID NO 2
<211> LENGTH: 666
<212> TYPE: DNA
<213> ORGANISM: Plasmodium falciparum

<400> SEQUENCE: 2

```
atgtggatcg taaagttctt gattgtggtc cacttcttca tcatatgcac catcaacttc      60
gacaagctct acattagtta ctcttacaac atcgtccctg aaaacggacg tatgcttaac     120
atgaggatct tggctgcaga aaagaaggac gaaaaggaag caagcgagca aggcgaagaa     180
tcccacaaga aggaaaactc tcaggaatct gcaaacggaa aagacgacgt taaggaggag     240
aagaagacca acgagaagaa ggacgacgga aagactgaca aggtacaaga aaaggttcta     300
gaaaagagtc ccaaggagag tcaaatggtc gacgacaaga agaagaccga ggccattcca     360
aagaaagtcg tgcagccaag ctcgagcaac tctggaggtc acgtcggtga agaagaagac     420
cacaacgaag gagagggaga gcacgaagag gaggaagaac acgaagaaga cgatgacgac     480
gaggacgacg acacatacaa caaagacgac ttggaggacg aagatctttg caagcacaac     540
aacggaggat gtggagatga caagctctgc gagtacgttg gaaaccgtcg cgtaaaatgt     600
```

```
aaatgtaagg aaggatacaa gttggaagga attgagtgcg ttgaacacca ccaccaccat    660
cactaa                                                              666

<210> SEQ ID NO 3
<211> LENGTH: 756
<212> TYPE: DNA
<213> ORGANISM: Plasmodium falciparum

<400> SEQUENCE: 3
atgtggatcg taaagttctt gattgtggtc cacttcttca tcatatgcac catcaacttc     60
gacaagctct acattagtta ctcttacaac atcgtccctg aaaacggacg tatgcttaac    120
atgaggatct tgggtgaaga aaagcctaac gttgacggtg tgtcaacatc taacacacct    180
ggcggaaacg aggcatctag tgcttctcct aaccttgctg acgctgcaga aaagaaggac    240
gaaaaggaag caagcgagca aggcgaagaa tcccacaaga aggaaaactc tcaggaatct    300
gcaaacggaa aagacgacgt taaggaggag aagaagacca cgagaagaa ggacgacgga     360 aagactgaca aggtacaaga aaaggttcta gaaaagagtc ccaaggagag tcaaatggtc    420
gacgacaaga agaagaccga ggccattcca agaaagtcg tgcagccaag ctcgagcaac     480
tctggaggtc acgtcggtga agaagaagac cacaacgaag gagagggaga gcacgaagag    540
gaggaagaac acgaagaaga cgatgacgac gaggacgacg acacatacaa caaagacgac    600
ttggaggacg aagatctttg caagcacaac aacggaggat gtggagatga caagctctgc    660
gagtacgttg gaaaccgtcg cgtaaaatgt aaatgtaagg aaggatacaa gttggaagga    720
attgagtgcg ttgaacacca ccaccaccat cactaa                              756

<210> SEQ ID NO 4
<211> LENGTH: 762
<212> TYPE: DNA
<213> ORGANISM: Plasmodium falciparum

<400> SEQUENCE: 4
atgaacattc tctgtattct cagctacatt tacttcttcg tcatcttcta cagtttaaac     60
ctcaacaaca aaaacgagaa cttcttggtg gtccgcagac tcatgaacga cgaaaaggga    120
gaaggtggct tcactagtaa gaacaaggaa acggaaaaca caacaggaa caacgagaac     180 gaactcaaag aagaaggatc tttgcccact aagatgaacg agaaaaacag taactccgcg    240
gataagcaac caaacgacat ctcccacgac gaaagcaaga gcaacagtaa caacgcccaa    300
aacatccaaa aggaacctga agagaaggaa aactcaaacc ccaacctcga ctcgagtgaa    360
aactccgctg aaagtgctac tagaagcgtc gacatcagtg aacacaactc aaacaacccc    420
gaaactaaag aagaaaacgg agaagaacct ctagacctgg aaattaacga aaacgcagaa    480
atcggccagg aacctccaaa ccgtcttcac ttcgacaacg ttgacgacga agtaccacat    540
tactcagccc tgaggtacaa caaggtcgag aagaacgtaa ccgacgagat gctcttgtac    600
aacatgatgt ccgaccaaaa ccgcaaaagc tgtgctatca caacggtgg ctgcagtgac     660 gaccagatct gcatcaacat caacaacatc ggtgtgaagt gcatttgtaa ggatggatac    720
ctacttggta ccaagtgcat tcaccaccac caccaccact ga                       762

<210> SEQ ID NO 5
<211> LENGTH: 207
<212> TYPE: DNA
<213> ORGANISM: Plasmodium falciparum
```

-continued

```
<400> SEQUENCE: 5
tacaacaagg tcgagaagaa cgtaaccgac gagatgctct tgtacaacat gatgtccgac    60
caaaaccgca aaagctgtgc tatcaacaac ggtggctgca gtgacgacca gatctgcatc   120
aacatcaaca catcggtgt gaagtgcatt tgtaaggatg gatacctact tggtaccaag    180
tgcattcacc accaccacca ccactga                                       207

<210> SEQ ID NO 6
<211> LENGTH: 498
<212> TYPE: DNA
<213> ORGANISM: Plasmodium falciparum

<400> SEQUENCE: 6
atgtggatcg taaagttctt gattgtggtc cacttcttca tcatatgcac catcaacttc    60
gacaagctct acattagtta ctcttacaac atcgtccctg aaaacggacg tatgcttaac   120
atgaggattc tagaaaagag tcccaaggag agtcaaatgg tcgacgacaa gaagaagacc   180
gaggccattc caagaaagt cgtgcagcca agctcgagca actctggagg tcacgtcggt    240
gaagaagaag accacaacga aggagaggga gagcacgaag aggaggaaga acacgaagaa   300
gacgatgacg acgaggacga cgacacatac aacaaagacg acttggagga cgaagatctt   360
tgcaagcaca acaacggagg atgtggagat gacaagctct gcgagtacgt tggaaaccgt   420
cgcgtaaaat gtaaatgtaa ggaaggatac aagttggaag gaattgagtg cgttgaacac   480
caccaccacc atcactaa                                                 498

<210> SEQ ID NO 7
<211> LENGTH: 540
<212> TYPE: DNA
<213> ORGANISM: Plasmodium falciparum

<400> SEQUENCE: 7
atgtggatcg taaagttctt gattgtggtc cacttcttca tcatatgcac catcaacttc    60
gacaagctct acattagtta ctcttacaac atcgtccctg aaaacggacg tatgcttaac   120
atgaggatct tgggtgaaga aaagcctaac gttgacggtg tgtcaacatc tctagaaaag   180
agtcccaagg agagtcaaat ggtcgacgac aagaagaaga ccgaggccat tccaagaaa    240 gtcgtgcagc caagctcgag caactctgga ggtcacgtcg gtgaagaaga agaccacaac   300
gaaggagagg gagagcacga gaggaggaa gaacacgaag aagacgatga cgacgaggac   360
gacgacacat acaacaaaga cgacttggag gacgaagatc tttgcaagca acaacggga   420 ggatgtggag atgacaagct ctgcgagtac gttggaaacc gtcgcgtaaa atgtaaatgt   480
aaggaaggat acaagttgga aggaattgag tgcgttgaac accaccacca ccatcactaa  540

<210> SEQ ID NO 8
<211> LENGTH: 516
<212> TYPE: DNA
<213> ORGANISM: Plasmodium falciparum

<400> SEQUENCE: 8
atgtggatcg taaagttctt gattgtggtc cacttcttca tcatatgcac catcaacttc    60
gacaagctct acattagtta ctcttacaac atcgtccctg aaaacggacg tatgcttaac   120
atgaggatct tgggtgaaga aaagcctcta gaaaagagtc ccaaggagag tcaaatggtc   180
gacgacaaga agaagaccga ggccattcca agaaagtcg tgcagccaag ctcgagcaac    240
tctggaggtc acgtcggtga agaagaagac cacaacgaag gagagggaga gcacgaagag   300
```

```
gaggaagaac acgaagaaga cgatgacgac gaggacgacg acacatacaa caaagacgac    360
ttggaggacg aagatctttg caagcacaac aacggaggat gtggagatga caagctctgc    420
gagtacgttg aaaccgtcg cgtaaaatgt aaatgtaagg aaggatacaa gttggaagga    480
attgagtgcg ttgaacacca ccaccaccat cactaa                              516

<210> SEQ ID NO 9
<211> LENGTH: 120
<212> TYPE: PRT
<213> ORGANISM: Plasmodium falciparum

<400> SEQUENCE: 9

Lys Ser Pro Lys Glu Ser Gln Met Val Asp Asp Lys Lys Thr Glu
  1               5                  10                  15

Ala Ile Pro Lys Lys Val Val Gln Pro Ser Ser Asn Ser Gly Gly
                 20                  25                  30

His Val Gly Glu Glu Asp His Asn Glu Gly Glu Gly Glu His Glu
             35                  40                  45

Glu Glu Glu Glu His Glu Glu Asp Asp Asp Glu Asp Asp Asp Thr
         50                  55                  60

Tyr Asn Lys Asp Asp Leu Glu Asp Glu Asp Leu Cys Lys His Asn Asn
 65                  70                  75                  80

Gly Gly Cys Gly Asp Asp Lys Leu Cys Glu Tyr Val Gly Asn Arg Arg
                 85                  90                  95

Val Lys Cys Lys Cys Lys Glu Gly Tyr Lys Leu Glu Gly Ile Glu Cys
                100                 105                 110

Val Glu His His His His His His
            115                 120

<210> SEQ ID NO 10
<211> LENGTH: 221
<212> TYPE: PRT
<213> ORGANISM: Plasmodium falciparum

<400> SEQUENCE: 10

Met Trp Ile Val Lys Phe Leu Ile Val Val His Phe Phe Ile Ile Cys
  1               5                  10                  15

Thr Ile Asn Phe Asp Lys Leu Tyr Ile Ser Tyr Ser Tyr Asn Ile Val
                 20                  25                  30

Pro Glu Asn Gly Arg Met Leu Asn Met Arg Ile Leu Ala Ala Glu Lys
             35                  40                  45

Lys Asp Glu Lys Glu Ala Glu Gln Gly Glu Glu Ser His Lys Lys
         50                  55                  60

Glu Asn Ser Gln Glu Ser Ala Asn Gly Lys Asp Asp Val Lys Glu Glu
 65                  70                  75                  80

Lys Lys Thr Asn Glu Lys Lys Asp Asp Gly Lys Thr Asp Lys Val Gln
                 85                  90                  95

Glu Lys Val Leu Glu Lys Ser Pro Lys Glu Ser Gln Met Val Asp Asp
                100                 105                 110

Lys Lys Lys Thr Glu Ala Ile Pro Lys Lys Val Val Gln Pro Ser Ser
            115                 120                 125

Ser Asn Ser Gly Gly His Val Gly Glu Glu Asp His Asn Glu Gly
        130                 135                 140

Glu Gly Glu His Glu Glu Glu Glu Glu His Glu Glu Asp Asp Asp Asp
145                 150                 155                 160

Glu Asp Asp Asp Thr Tyr Asn Lys Asp Asp Leu Glu Asp Glu Asp Leu
                165                 170                 175
```

-continued

```
Cys Lys His Asn Asn Gly Gly Cys Gly Asp Asp Lys Leu Cys Glu Tyr
            180                 185                 190

Val Gly Asn Arg Arg Val Lys Cys Lys Cys Glu Gly Tyr Lys Leu
        195                 200                 205

Glu Gly Ile Glu Cys Val Glu His His His His His
    210                 215                 220

<210> SEQ ID NO 11
<211> LENGTH: 181
<212> TYPE: PRT
<213> ORGANISM: Plasmodium falciparum

<400> SEQUENCE: 11

Met Arg Ile Leu Ala Ala Glu Lys Lys Asp Glu Lys Glu Ala Ser Glu
1               5                   10                  15

Gln Gly Glu Glu Ser His Lys Lys Glu Asn Ser Gln Glu Ser Ala Asn
            20                  25                  30

Gly Lys Asp Asp Val Lys Glu Lys Lys Thr Asn Glu Lys Lys Asp
        35                  40                  45

Asp Gly Lys Thr Asp Lys Val Gln Glu Lys Val Leu Glu Lys Ser Pro
    50                  55                  60

Lys Glu Ser Gln Met Val Asp Asp Lys Lys Thr Glu Ala Ile Pro
65              70                  75                  80

Lys Lys Val Val Gln Pro Ser Ser Asn Ser Gly Gly His Val Gly
            85                  90                  95

Glu Glu Glu Asp His Asn Glu Gly Glu Gly His Glu Glu Glu
        100                 105                 110

Glu His Glu Glu Asp Asp Asp Glu Asp Asp Thr Tyr Asn Lys
    115                 120                 125

Asp Asp Leu Glu Asp Glu Asp Leu Cys Lys His Asn Asn Gly Gly Cys
130                 135                 140

Gly Asp Asp Lys Leu Cys Glu Tyr Val Gly Asn Arg Arg Val Lys Cys
145                 150                 155                 160

Lys Cys Lys Glu Gly Tyr Lys Leu Glu Gly Ile Glu Cys Val Glu His
                165                 170                 175

His His His His His
        180

<210> SEQ ID NO 12
<211> LENGTH: 251
<212> TYPE: PRT
<213> ORGANISM: Plasmodium falciparum

<400> SEQUENCE: 12

Met Trp Ile Val Lys Phe Leu Ile Val Val His Phe Phe Ile Ile Cys
1               5                   10                  15

Thr Ile Asn Phe Asp Lys Leu Tyr Ile Ser Tyr Ser Tyr Asn Ile Val
            20                  25                  30

Pro Glu Asn Gly Arg Met Leu Asn Met Arg Ile Leu Gly Glu Glu Lys
        35                  40                  45

Pro Asn Val Asp Gly Val Ser Thr Ser Asn Thr Pro Gly Gly Asn Glu
    50                  55                  60

Ala Ser Ser Ala Ser Pro Asn Leu Ala Asp Ala Glu Lys Lys Asp
65              70                  75                  80
```

```
Glu Lys Glu Ala Ser Glu Gln Gly Glu Ser His Lys Lys Glu Asn
                 85                  90                  95

Ser Gln Glu Ser Ala Asn Gly Lys Asp Asp Val Lys Glu Lys Lys
            100                 105                 110

Thr Asn Glu Lys Lys Asp Asp Gly Lys Thr Asp Lys Val Gln Glu Lys
            115                 120                 125

Val Leu Glu Lys Ser Pro Lys Glu Ser Gln Met Val Asp Asp Lys
130                 135                 140

Lys Thr Glu Ala Ile Pro Lys Lys Val Val Gln Pro Ser Ser Asn
145                 150                 155                 160

Ser Gly Gly His Val Gly Glu Glu Asp His Asn Glu Gly Glu Gly
                165                 170                 175

Glu His Glu Glu Glu Glu His Glu Asp Asp Asp Asp Glu Asp
            180                 185                 190

Asp Asp Thr Tyr Asn Lys Asp Asp Leu Glu Asp Glu Asp Leu Cys Lys
            195                 200                 205

His Asn Asn Gly Gly Cys Gly Asp Asp Lys Leu Cys Glu Tyr Val Gly
    210                 215                 220

Asn Arg Arg Val Lys Cys Lys Cys Lys Gly Tyr Lys Leu Glu Gly
225                 230                 235                 240

Ile Glu Cys Val Glu His His His His His
                245                 250

<210> SEQ ID NO 13
<211> LENGTH: 211
<212> TYPE: PRT
<213> ORGANISM: Plasmodium falciparum

<400> SEQUENCE: 13

Met Arg Ile Leu Gly Glu Glu Lys Pro Asn Val Asp Gly Val Ser Thr
1               5                   10                  15

Ser Asn Thr Pro Gly Gly Asn Glu Ala Ser Ser Ala Ser Pro Asn Leu
            20                  25                  30

Ala Asp Ala Ala Glu Lys Lys Asp Glu Lys Glu Ala Ser Glu Gln Gly
        35                  40                  45

Glu Glu Ser His Lys Lys Glu Asn Ser Gln Glu Ser Ala Asn Gly Lys
    50                  55                  60

Asp Asp Val Lys Glu Lys Lys Thr Asn Glu Lys Lys Asp Asp Gly
65                  70                  75                  80

Lys Thr Asp Lys Val Gln Glu Lys Val Leu Glu Lys Ser Pro Lys Glu
                85                  90                  95

Ser Gln Met Val Asp Asp Lys Lys Thr Glu Ala Ile Pro Lys Lys
            100                 105                 110

Val Val Gln Pro Ser Ser Asn Ser Gly Gly His Val Gly Glu Glu
        115                 120                 125

Glu Asp His Asn Glu Gly Glu Gly Glu His Glu Glu Glu Glu His
    130                 135                 140

Glu Glu Asp Asp Asp Asp Glu Asp Asp Asp Thr Tyr Asn Lys Asp Asp
145                 150                 155                 160

Leu Glu Asp Glu Asp Leu Cys Lys His Asn Asn Gly Gly Cys Gly Asp
                165                 170                 175

Asp Lys Leu Cys Glu Tyr Val Gly Asn Arg Arg Val Lys Cys Lys Cys
            180                 185                 190
```

```
Lys Glu Gly Tyr Lys Leu Glu Gly Ile Glu Cys Val Glu His His
        195                 200                 205
His His His
    210

<210> SEQ ID NO 14
<211> LENGTH: 253
<212> TYPE: PRT
<213> ORGANISM: Plasmodium falciparum

<400> SEQUENCE: 14

Met Asn Ile Leu Cys Ile Leu Ser Tyr Ile Tyr Phe Phe Val Ile Phe
  1               5                  10                  15

Tyr Ser Leu Asn Leu Asn Asn Lys Asn Glu Asn Phe Leu Val Val Arg
             20                  25                  30

Arg Leu Met Asn Asp Glu Lys Gly Glu Gly Gly Phe Thr Ser Lys Asn
         35                  40                  45

Lys Glu Asn Gly Asn Asn Arg Asn Glu Asn Glu Leu Lys Glu
     50                  55                  60

Glu Gly Ser Leu Pro Thr Lys Met Asn Glu Lys Asn Ser Asn Ser Ala
 65                  70                  75                  80

Asp Lys Gln Pro Asn Asp Ile Ser His Asp Glu Ser Lys Ser Asn Ser
                 85                  90                  95

Asn Asn Ala Gln Asn Ile Gln Lys Glu Pro Glu Lys Glu Asn Ser
            100                 105                 110

Asn Pro Asn Leu Asp Ser Ser Glu Asn Ser Ala Glu Ser Ala Thr Arg
        115                 120                 125

Ser Val Asp Ile Ser Glu His Asn Ser Asn Asn Pro Glu Thr Lys Glu
    130                 135                 140

Glu Asn Gly Glu Glu Pro Leu Asp Leu Glu Ile Asn Glu Asn Ala Glu
145                 150                 155                 160

Ile Gly Gln Glu Pro Pro Asn Arg Leu His Phe Asp Asn Val Asp Asp
                165                 170                 175

Glu Val Pro His Tyr Ser Ala Leu Arg Tyr Asn Lys Val Glu Lys Asn
            180                 185                 190

Val Thr Asp Glu Met Leu Leu Tyr Asn Met Met Ser Asp Gln Asn Arg
        195                 200                 205

Lys Ser Cys Ala Ile Asn Asn Gly Gly Cys Ser Asp Asp Gln Ile Cys
    210                 215                 220

Ile Asn Ile Asn Asn Ile Gly Val Lys Cys Ile Cys Lys Asp Gly Tyr
225                 230                 235                 240

Leu Leu Gly Thr Lys Cys Ile His His His His His
                245                 250

<210> SEQ ID NO 15
<211> LENGTH: 68
<212> TYPE: PRT
<213> ORGANISM: Plasmodium falciparum

<400> SEQUENCE: 15

Tyr Asn Lys Val Glu Lys Asn Val Thr Asp Glu Met Leu Leu Tyr Asn
  1               5                  10                  15

Met Met Ser Asp Gln Asn Arg Lys Ser Cys Ala Ile Asn Asn Gly Gly
             20                  25                  30

Cys Ser Asp Asp Gln Ile Cys Ile Asn Ile Asn Asn Ile Gly Val Lys
         35                  40                  45
```

```
Cys Ile Cys Lys Asp Gly Tyr Leu Leu Gly Thr Lys Cys Ile His His
         50                  55                  60

His His His His
 65
```

<210> SEQ ID NO 16
<211> LENGTH: 212
<212> TYPE: PRT
<213> ORGANISM: Plasmodium vivax

<400> SEQUENCE: 16

```
Met Lys Val Ala Tyr Phe Leu Ser Val Leu Asp Leu Leu Ile Ile Phe
 1               5                  10                  15

Ser Leu Tyr Phe Asp Gly Arg Arg Ser Ala Phe Ala Gly Ile Ala Ala
             20                  25                  30

Cys Ile Arg His Gly Arg Ile Leu Gly Glu Gly Gly Glu Gln Ser Gly
         35                  40                  45

Gly Ala Ser Gly Gly Ser Ser Gly Gly Ser Ser Gly Asp Ser Ser Gly
     50                  55                  60

Gly Leu Ser Gly Gly Ser Ser Gly Gly Pro Ser Pro Pro Ala Gly Ser
 65                  70                  75                  80

Ser Gly Ser Gly Gly Ser Asp Pro Ala Asn Ser Ala Thr Gly Pro Gln
                 85                  90                  95

Asn Ser Thr Pro Gly Ser Gly Gln Thr Gly Asp His Ser Ala Glu
            100                 105                 110

Ala Glu Asn Gly Asp Tyr Asn Glu Gln Gly Asp Asp His Gly Asp Asp
        115                 120                 125

His Gly Asp Asp His Gly Asp His Gly Asp Glu Gln Asp Gly Glu
    130                 135                 140

Asp Tyr Asp Asp Ala Glu Asp Asp Leu Tyr Glu Leu Ser Glu Val
145                 150                 155                 160

Asp Glu Asn Ala Asn Leu Cys Leu Asp Asn Asn Gly Gly Cys Gly Asp
                165                 170                 175

Asp Lys Ile Cys Glu Asn Leu Gly Lys Gly Ile Val Lys Cys Leu Cys
            180                 185                 190

Lys Pro Gly Tyr Lys Leu Val Gly Thr Glu Cys Val Glu Ser His His
        195                 200                 205

His His His His
        210
```

<210> SEQ ID NO 17
<211> LENGTH: 165
<212> TYPE: PRT
<213> ORGANISM: Plasmodium falciparum

<400> SEQUENCE: 17

```
Met Trp Ile Val Lys Phe Leu Ile Val Val His Phe Phe Ile Ile Cys
 1               5                  10                  15

Thr Ile Asn Phe Asp Lys Leu Tyr Ile Ser Tyr Ser Tyr Asn Ile Val
             20                  25                  30

Pro Glu Asn Gly Arg Met Leu Asn Met Arg Ile Leu Glu Lys Ser Pro
         35                  40                  45

Lys Glu Ser Gln Met Val Asp Asp Lys Lys Thr Glu Ala Ile Pro
     50                  55                  60

Lys Lys Val Val Gln Pro Ser Ser Asn Ser Gly Gly His Val Gly
 65                  70                  75                  80
```

```
Glu Glu Glu Asp His Asn Glu Gly Gly Glu His Glu Glu Glu
            85                  90                  95

Glu His Glu Glu Asp Asp Asp Glu Asp Asp Thr Tyr Asn Lys
            100                 105                 110

Asp Asp Leu Glu Asp Glu Asp Leu Cys Lys His Asn Asn Gly Gly Cys
        115                 120                 125

Gly Asp Asp Lys Leu Cys Glu Tyr Val Gly Asn Arg Arg Val Lys Cys
    130                 135                 140

Lys Cys Lys Glu Gly Tyr Lys Leu Glu Gly Ile Glu Cys Val Glu His
145                 150                 155                 160

His His His His His
            165

<210> SEQ ID NO 18
<211> LENGTH: 125
<212> TYPE: PRT
<213> ORGANISM: Plasmodium falciparum

<400> SEQUENCE: 18

Met Arg Ile Leu Glu Lys Ser Pro Lys Glu Ser Gln Met Val Asp Asp
1               5                   10                  15

Lys Lys Lys Thr Glu Ala Ile Pro Lys Lys Val Val Gln Pro Ser Ser
            20                  25                  30

Ser Asn Ser Gly Gly His Val Gly Glu Glu Asp His Asn Glu Gly
            35                  40                  45

Glu Gly Glu His Glu Glu Glu Glu His Glu Asp Asp Asp Asp
    50                  55                  60

Glu Asp Asp Asp Thr Tyr Asn Lys Asp Asp Leu Glu Asp Glu Asp Leu
65                  70                  75                  80

Cys Lys His Asn Asn Gly Gly Cys Gly Asp Asp Lys Leu Cys Glu Tyr
            85                  90                  95

Val Gly Asn Arg Arg Val Lys Cys Lys Cys Lys Glu Gly Tyr Lys Leu
            100                 105                 110

Glu Gly Ile Glu Cys Val Glu His His His His His His
        115                 120                 125

<210> SEQ ID NO 19
<211> LENGTH: 179
<212> TYPE: PRT
<213> ORGANISM: Plasmodium falciparum

<400> SEQUENCE: 19

Met Trp Ile Val Lys Phe Leu Ile Val Val His Phe Phe Ile Ile Cys
1               5                   10                  15

Thr Ile Asn Phe Asp Lys Leu Tyr Ile Ser Tyr Ser Tyr Asn Ile Val
            20                  25                  30

Pro Glu Asn Gly Arg Met Leu Asn Met Arg Ile Leu Gly Glu Glu Lys
            35                  40                  45

Pro Asn Val Asp Gly Val Ser Thr Ser Leu Glu Lys Ser Pro Lys Glu
        50                  55                  60

Ser Gln Met Val Asp Asp Lys Lys Lys Thr Glu Ala Ile Pro Lys Lys
65                  70                  75                  80

Val Val Gln Pro Ser Ser Ser Asn Ser Gly Gly His Val Gly Glu Glu
            85                  90                  95

Glu Asp His Asn Glu Gly Gly Glu His Glu Glu Glu Glu His
            100                 105                 110
```

```
Glu Glu Asp Asp Asp Glu Asp Asp Thr Tyr Asn Lys Asp Asp
    115                 120                 125

Leu Glu Asp Glu Asp Leu Cys Lys His Asn Asn Gly Cys Gly Asp
130                 135                 140

Asp Lys Leu Cys Glu Tyr Val Gly Asn Arg Arg Val Lys Cys Lys Cys
145                 150                 155                 160

Lys Glu Gly Tyr Lys Leu Glu Gly Ile Glu Cys Val Glu His His His
                165                 170                 175

His His His

<210> SEQ ID NO 20
<211> LENGTH: 139
<212> TYPE: PRT
<213> ORGANISM: Plasmodium falciparum

<400> SEQUENCE: 20

Met Arg Ile Leu Gly Glu Glu Lys Pro Asn Val Asp Gly Val Ser Thr
1               5                   10                  15

Ser Leu Glu Lys Ser Pro Lys Glu Ser Gln Met Val Asp Asp Lys Lys
            20                  25                  30

Lys Thr Glu Ala Ile Pro Lys Lys Val Val Gln Pro Ser Ser Ser Asn
        35                  40                  45

Ser Gly Gly His Val Gly Glu Glu Glu Asp His Asn Glu Gly Glu Gly
    50                  55                  60

Glu His Glu Glu Glu Glu Glu His Glu Asp Asp Asp Asp Glu Asp
65                  70                  75                  80

Asp Asp Thr Tyr Asn Lys Asp Asp Leu Glu Asp Glu Asp Leu Cys Lys
                85                  90                  95

His Asn Asn Gly Gly Cys Gly Asp Asp Lys Leu Cys Glu Tyr Val Gly
            100                 105                 110

Asn Arg Arg Val Lys Cys Lys Cys Lys Glu Gly Tyr Lys Leu Glu Gly
        115                 120                 125

Ile Glu Cys Val Glu His His His His His His
    130                 135

<210> SEQ ID NO 21
<211> LENGTH: 171
<212> TYPE: PRT
<213> ORGANISM: Plasmodium falciparum

<400> SEQUENCE: 21

Met Trp Ile Val Lys Phe Leu Ile Val Val His Phe Phe Ile Ile Cys
1               5                   10                  15

Thr Ile Asn Phe Asp Lys Leu Tyr Ile Ser Tyr Ser Tyr Asn Ile Val
            20                  25                  30

Pro Glu Asn Gly Arg Met Leu Asn Met Arg Ile Leu Gly Glu Glu Lys
        35                  40                  45

Pro Leu Glu Lys Ser Pro Lys Glu Ser Gln Met Val Asp Asp Lys Lys
    50                  55                  60

Lys Thr Glu Ala Ile Pro Lys Lys Val Val Gln Pro Ser Ser Ser Asn
65                  70                  75                  80

Ser Gly Gly His Val Gly Glu Glu Asp His Asn Glu Gly Glu Gly
                85                  90                  95

Glu His Glu Glu Glu Glu Glu His Glu Asp Asp Asp Asp Glu Asp
            100                 105                 110

Asp Asp Thr Tyr Asn Lys Asp Asp Leu Glu Asp Glu Asp Leu Cys Lys
        115                 120                 125
```

-continued

His Asn Asn Gly Gly Cys Gly Asp Asp Lys Leu Cys Glu Tyr Val Gly
    130                    135                   140

Asn Arg Arg Val Lys Cys Lys Cys Lys Glu Gly Tyr Lys Leu Glu Gly
145                    150                    155                   160

Ile Glu Cys Val Glu His His His His His His
              165                    170

<210> SEQ ID NO 22
<211> LENGTH: 131
<212> TYPE: PRT
<213> ORGANISM: Plasmodium falciparum

<400> SEQUENCE: 22

Met Arg Ile Leu Gly Glu Glu Lys Pro Leu Glu Lys Ser Pro Lys Glu
1                 5                    10                   15

Ser Gln Met Val Asp Asp Lys Lys Lys Thr Glu Ala Ile Pro Lys Lys
              20                    25                   30

Val Val Gln Pro Ser Ser Asn Ser Gly His Val Gly Glu Glu
            35                    40                   45

Glu Asp His Asn Glu Gly Glu Gly Glu His Glu Glu Glu Glu His
     50                   55                    60

Glu Glu Asp Asp Asp Asp Glu Asp Asp Thr Tyr Asn Lys Asp Asp
65                  70                    75                   80

Leu Glu Asp Glu Asp Leu Cys Lys His Asn Asn Gly Gly Cys Gly Asp
              85                    90                   95

Asp Lys Leu Cys Glu Tyr Val Gly Asn Arg Arg Val Lys Cys Lys Cys
            100                   105                 110

Lys Glu Gly Tyr Lys Leu Glu Gly Ile Glu Cys Val Glu His His His
            115                   120                 125

His His His
    130

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 23
tatagcagat ctttgtcgaa gttgatggtg ca                                            32

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 24
atatggctgc agccaagatc ctcatgttaa gcat                                        34

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic
     primer -continued

```
<400> SEQUENCE: 25
attaatctag aggcttttct tcacccaaga tcctcatg                             38

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Tyr Asn Lys Val Glu
 1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Asn Lys Val Glu
 1               5

<210> SEQ ID NO 28
<211> LENGTH: 540
<212> TYPE: DNA
<213> ORGANISM: Plasmodium falciparum

<400> SEQUENCE: 28
atgtggatcg taaagttctt gattgtggtc cacttcttca tcatatgcac catcaacttc     60
gacaagctct acattagtta ctcttacaac atcgtccctg aaaacggacg tatgcttaac    120
atgaggatct tgggtgaaga aaagcctaac gttgacggtg tgtcaacatc tctagaaaag    180
agtcccaagg agagtcaaat ggtcgacgac aagaagaaga ccgaggccat tccaaagaaa    240
gtcgtgcagc caagctcgag caactctgga ggtcacgtcg gtgaagaaga agaccacaac    300
gaaggagagg gagagcacga gaggaggaa gaacacgaag aagacgatga cgacgaggac    360
gacgacacat acaacaaaga cgacttggag gacgaagatc tttgcaagca caacaacgga    420
ggatgtggag atgacaagct ctgcgagtac gttggaaacc gtcgcgtaaa atgtaaatgt    480
aaggaaggat acaagttgga aggaattgag tgcgttgaac accaccacca ccatcactaa    540

<210> SEQ ID NO 29
<211> LENGTH: 516
<212> TYPE: DNA
<213> ORGANISM: Plasmodium falciparum

<400> SEQUENCE: 29
atgtggatcg taaagttctt gattgtggtc cacttcttca tcatatgcac catcaacttc     60
gacaagctct acattagtta ctcttacaac atcgtccctg aaaacggacg tatgcttaac    120
atgaggatct tgggtgaaga aaagcctcta gaaaagagtc ccaaggagag tcaaatggtc    180
gacgacaaga gaagaccga ggccattcca agaaagtcg tgcagccaag ctcgagcaac    240
tctggaggtc acgtcggtga agaagaagac cacaacgaag gagagggaga gcacgaagag    300
gaggaagaac acgaagaaga cgatgacgac gaggacgacg acacatacaa caaagacgac    360
ttggaggacg aagatctttg caagcacaac aacggaggat gtggagatga caagctctgc    420
```

-continued

```
gagtacgttg gaaaccgtcg cgtaaaatgt aaatgtaagg aaggatacaa gttggaagga      480
attgagtgcg ttgaacacca ccaccaccat cactaa                                516
```

<210> SEQ ID NO 30
<211> LENGTH: 161
<212> TYPE: PRT
<213> ORGANISM: Plasmodium falciparum

<400> SEQUENCE: 30

```
Met Lys Val Ala Tyr Phe Leu Ser Val Leu Asp Leu Leu Ile Ile Phe
  1               5                  10                  15

Ser Leu Tyr Phe Asp Gly Arg Arg Ser Ala Phe Ala Gly Ile Ala Ala
                 20                  25                  30

Cys Ile Arg His Gly Arg Ile Leu Gly Glu Gly Gly Glu Gln Asn Ser
             35                  40                  45

Thr Pro Gly Ser Gly Gly Gln Thr Gly Asp His Ser Ala Glu Ala Glu
         50                  55                  60

Asn Gly Asp Tyr Asn Glu Gln Gly Asp His Gly Asp His Gly
 65                  70                  75                  80

Asp Asp His Gly Asp His Gly Asp Glu Gln Asp Gly Glu Asp Tyr
                 85                  90                  95

Asp Asp Ala Glu Asp Asp Leu Tyr Glu Leu Ser Glu Val Asp Glu
            100                 105                 110

Asn Ala Asn Leu Cys Leu Asp Asn Asn Gly Gly Cys Gly Asp Asp Lys
        115                 120                 125

Ile Cys Glu Asn Leu Gly Lys Gly Ile Val Lys Cys Leu Cys Lys Pro
    130                 135                 140

Gly Tyr Lys Leu Val Gly Thr Glu Cys Val Glu His His His His His
145                 150                 155                 160

His
```

<210> SEQ ID NO 31
<211> LENGTH: 83
<212> TYPE: PRT
<213> ORGANISM: Plasmodium falciparum

<400> SEQUENCE: 31

```
Arg Val Ser Thr Ser Asp Thr Pro Gly Gly Asn Glu Ser Ser Ser Ala
  1               5                  10                  15

Phe Pro Gln Phe Ile Trp Ser Ala Glu Lys Lys Asp Glu Lys Glu Ala
                 20                  25                  30

Ser Glu Gln Gly Glu Glu Ser His Lys Lys Glu Asn Ser Gln Glu Ser
             35                  40                  45

Ala Asn Gly Lys Asp Asp Val Lys Glu Glu Lys Thr Asn Glu Lys
         50                  55                  60

Lys Asp Asp Gly Lys Thr Asp Lys Val Gln Glu Lys Val Leu Glu Lys
 65                  70                  75                  80

Ser Pro Lys
```

<210> SEQ ID NO 32
<211> LENGTH: 272
<212> TYPE: PRT
<213> ORGANISM: Plasmodium falciparum -continued

<400> SEQUENCE: 32

Met Trp Ile Val Lys Phe Leu Ile Val Val His Phe Phe Ile Ile Cys
1               5                   10                  15

Thr Ile Asn Phe Asp Lys Leu Tyr Ile Ser Tyr Ser Tyr Asn Ile Val
            20                  25                  30

Pro Glu Asn Gly Arg Met Leu Asn Met Arg Ile Leu Gly Glu Glu Lys
        35                  40                  45

Pro Asn Val Asp Gly Val Ser Thr Ser Asp Thr Pro Gly Gly Asn Glu
    50                  55                  60

Ser Ser Ser Ala Ser Pro Asn Leu Ser Asp Ala Ala Glu Lys Lys Asp
65                  70                  75                  80

Glu Lys Glu Ala Ser Glu Gln Gly Glu Ser His Lys Lys Glu Asn
                85                  90                  95

Ser Gln Glu Ser Ala Asn Gly Lys Asp Asp Val Lys Glu Glu Lys Lys
            100                 105                 110

Thr Asn Glu Lys Lys Asp Asp Gly Lys Thr Asp Lys Val Gln Glu Lys
        115                 120                 125

Val Leu Glu Lys Ser Pro Lys Glu Ser Gln Met Val Asp Asp Lys Lys
    130                 135                 140

Lys Thr Glu Ala Ile Pro Lys Lys Val Val Gln Pro Ser Ser Ser Asn
145                 150                 155                 160

Ser Gly Gly His Val Gly Glu Glu Glu Asp His Asn Glu Gly Glu Gly
                165                 170                 175

Glu His Glu Glu Glu Glu Glu His Glu Glu Asp Asp Asp Asp Glu Asp
            180                 185                 190

Asp Asp Thr Tyr Asn Lys Asp Asp Leu Glu Asp Glu Asp Leu Cys Lys
        195                 200                 205

His Asn Asn Gly Gly Cys Gly Asp Asp Lys Leu Cys Glu Tyr Val Gly
    210                 215                 220

Asn Arg Arg Val Lys Cys Lys Cys Lys Glu Gly Tyr Lys Leu Glu Gly
225                 230                 235                 240

Ile Glu Cys Val Glu Leu Leu Ser Leu Ala Ser Ser Ser Leu Asn Leu
                245                 250                 255

Ile Phe Asn Ser Phe Ile Thr Ile Phe Val Val Ile Leu Leu Ile Asn
            260                 265                 270

<210> SEQ ID NO 33
<211> LENGTH: 760
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (10)..(759)

<400> SEQUENCE: 33 ccaggatcc atg tgg atc gta aag ttc ttg att gtg gtc cac ttc ttc atc      51
          Met Trp Ile Val Lys Phe Leu Ile Val Val His Phe Phe Ile
          1               5                   10 ata tgc acc atc aac ttc gac aag ctc tac att agt tac tct tac aac       99
Ile Cys Thr Ile Asn Phe Asp Lys Leu Tyr Ile Ser Tyr Ser Tyr Asn
15              20                  25                  30 atc gtc cct gaa aac gga cgt atg ctt aac atg agg atc ttg ggt gaa      147
Ile Val Pro Glu Asn Gly Arg Met Leu Asn Met Arg Ile Leu Gly Glu
            35                  40                  45

```
gaa aag cct aac gtt gac ggt gtg tca aca tct aac aca cct ggc gga      195
Glu Lys Pro Asn Val Asp Gly Val Ser Thr Ser Asn Thr Pro Gly Gly
             50                  55                  60 aac gag gca tct agt gct tct cct aac ctt gct gac gct gca gaa aag      243
Asn Glu Ala Ser Ser Ala Ser Pro Asn Leu Ala Asp Ala Ala Glu Lys
         65                  70                  75 aag gac gaa aag gaa gca agc gag caa ggc gaa gaa tcc cac aag aag      291
Lys Asp Glu Lys Glu Ala Ser Glu Gln Gly Glu Glu Ser His Lys Lys
     80                  85                  90 gaa aac tct cag gaa tct gca aac gga aaa gac gac gtt aag gag gag      339
Glu Asn Ser Gln Glu Ser Ala Asn Gly Lys Asp Asp Val Lys Glu Glu
 95                 100                 105                 110 aag aag acc aac gag aag aag gac gac gga aag act gac aag gta caa      387
Lys Lys Thr Asn Glu Lys Lys Asp Asp Gly Lys Thr Asp Lys Val Gln
                115                 120                 125 gaa aag gtt cta gaa aag agt ccc aag gag agt caa atg gtc gac gac      435
Glu Lys Val Leu Glu Lys Ser Pro Lys Glu Ser Gln Met Val Asp Asp
            130                 135                 140 aag aag aag acc gag gcc att cca aag aaa gtc gtg cag cca agc tcg      483
Lys Lys Lys Thr Glu Ala Ile Pro Lys Lys Val Val Gln Pro Ser Ser
        145                 150                 155 agc aac tct gga ggt cac gtc ggt gaa gaa gaa gac cac aac gaa gga      531
Ser Asn Ser Gly Gly His Val Gly Glu Glu Glu Asp His Asn Glu Gly
    160                 165                 170 gag gga gag cac gaa gag gag gaa gaa cac gaa gaa gac gat gac gac      579
Glu Gly Glu His Glu Glu Glu Glu His Glu Glu Asp Asp Asp Asp
175                 180                 185                 190 gag gac gac gac aca tac aac aaa gac gac ttg gag gac gaa gat ctt      627
Glu Asp Asp Asp Thr Tyr Asn Lys Asp Asp Leu Glu Asp Glu Asp Leu
                195                 200                 205 tgc aag cac aac aac gga gga tgt gga gat gac aag ctc tgc gag tac      675
Cys Lys His Asn Asn Gly Gly Cys Gly Asp Asp Lys Leu Cys Glu Tyr
            210                 215                 220 gtt gga aac cgt cgc gta aaa tgt aaa tgt aag gaa gga tac aag ttg      723
Val Gly Asn Arg Arg Val Lys Cys Lys Cys Lys Glu Gly Tyr Lys Leu
        225                 230                 235 gaa gga att gag tgc gtt gaa cac cac cac cac cat c                    760
Glu Gly Ile Glu Cys Val Glu His His His His His
    240                 245                 250

<210> SEQ ID NO 34
<211> LENGTH: 250
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 34

Met Trp Ile Val Lys Phe Leu Ile Val Val His Phe Phe Ile Ile Cys
 1               5                  10                  15

Thr Ile Asn Phe Asp Lys Leu Tyr Ile Ser Tyr Ser Tyr Asn Ile Val
             20                  25                  30

Pro Glu Asn Gly Arg Met Leu Asn Met Arg Ile Leu Gly Glu Glu Lys
         35                  40                  45

Pro Asn Val Asp Gly Val Ser Thr Ser Asn Thr Pro Gly Gly Asn Glu
     50                  55                  60

Ala Ser Ser Ala Ser Pro Asn Leu Ala Asp Ala Ala Glu Lys Lys Asp
65                  70                  75                  80
```

```
Glu Lys Glu Ala Ser Glu Gln Gly Glu Ser His Lys Lys Glu Asn
             85                  90                  95
Ser Gln Glu Ser Ala Asn Gly Lys Asp Asp Val Lys Glu Lys Lys
            100                 105                 110
Thr Asn Glu Lys Lys Asp Asp Gly Lys Thr Asp Lys Val Gln Glu Lys
        115                 120                 125
Val Leu Glu Lys Ser Pro Lys Glu Ser Gln Met Val Asp Asp Lys Lys
130                 135                 140
Lys Thr Glu Ala Ile Pro Lys Lys Val Val Gln Pro Ser Ser Ser Asn
145                 150                 155                 160
Ser Gly Gly His Val Gly Glu Glu Asp His Asn Glu Gly Glu Gly
            165                 170                 175
Glu His Glu Glu Glu Glu Glu His Glu Asp Asp Asp Asp Glu Asp
            180                 185                 190
Asp Asp Thr Tyr Asn Lys Asp Asp Leu Glu Asp Glu Asp Leu Cys Lys
        195                 200                 205
His Asn Asn Gly Gly Cys Gly Asp Asp Lys Leu Cys Glu Tyr Val Gly
        210                 215                 220
Asn Arg Arg Val Lys Cys Lys Cys Lys Glu Gly Tyr Lys Leu Glu Gly
225                 230                 235                 240
Ile Glu Cys Val Glu His His His His
            245                 250

<210> SEQ ID NO 35
<211> LENGTH: 760
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 35
ggggcgtctg aattcttagt gatggtggtg gtggtgttca acgcactcaa ttccttccaa    60
cttgtatcct tccttacatt tacattttac gcgacggttt ccaacgtact cgcagagctt   120
gtcatctcca catcctccgt tgttgtgctt gcaaagatct tcgtcctcca agtcgtcttt   180
gttgtatgtg tcgtcgtcct cgtcgtcatc gtcttcttcg tgttcttcct cctcttcgtg   240 ctctcccttct ccttcgttgt ggtcttcttc ttcaccgacg tgacctccag agttgctcga   300
gcttggctgc acgactttct ttggaatggc ctcggtcttc ttcttgtcgt cgaccatttg   360
actctccttg ggactctttt ctagaacctt ttcttgtacc ttgtcagtct ttccgtcgtc   420
cttcttctcg ttggtcttct tctcctcctt aacgtcgtct tttccgtttg cagattcctg   480
agagttttcc ttcttgtggg attcttcgcc ttgctcgctt gcttcctttt cgtccttctt   540
ttctgcagcg tcagcaaggt taggagaagc actagatgcc tcgtttccgc caggtgtgtt   600
agatgttgac acaccgtcaa cgttaggctt ttcttcaccc aagatcctca tgttaagcat   660
acgtccgttt tcagggacga tgttgtaaga gtaactaatg tagagcttgt cgaagttgat   720
ggtgcatatg atgaagaagt ggaccacaat caagaacttt                         760

<210> SEQ ID NO 36
<211> LENGTH: 69
<212> TYPE: PRT
<213> ORGANISM: Artificial Sequence
<220> FEATURE:
<223> OTHER INFORMATION: Description of Artificial Sequence: Synthetic
      construct
```

<400> SEQUENCE: 36

Met Trp Ile Val Lys Phe Leu Ile Val Val His Phe Phe Ile Ile Cys
1               5                   10                  15

Thr Ile Asn Phe Asp Lys Asp Leu Cys Lys His Asn Asn Gly Gly Cys
                20                  25                  30

Gly Asp Asp Lys Leu Cys Glu Tyr Val Gly Asn Arg Arg Val Lys Cys
            35                  40                  45

Lys Cys Lys Glu Gly Tyr Lys Leu Glu Gly Ile Glu Cys Val Glu His
        50                  55                  60

His His His His His
65

<210> SEQ ID NO 37
<211> LENGTH: 171
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 37

Met Trp Ile Val Lys Phe Leu Ile Val Val His Phe Phe Ile Ile Cys
1               5                   10                  15

Thr Ile Asn Phe Asp Lys Leu Tyr Ile Ser Tyr Ser Tyr Asn Ile Val
                20                  25                  30

Pro Glu Asn Gly Arg Met Leu Asn Met Arg Ile Leu Gly Glu Glu Lys
            35                  40                  45

Pro Leu Glu Lys Ser Pro Lys Glu Ser Gln Met Val Asp Asp Lys Lys
        50                  55                  60

Lys Thr Glu Ala Ile Pro Lys Lys Val Val Gln Pro Ser Ser Ser Asn
65                  70                  75                  80

Ser Gly Gly His Val Gly Glu Glu Glu Asp His Asn Glu Gly Glu Gly
                85                  90                  95

Glu His Glu Glu Glu Glu Glu His Glu Glu Asp Asp Asp Asp Glu Asp
            100                 105                 110

Asp Asp Thr Tyr Asn Lys Asp Asp Leu Glu Asp Glu Asp Leu Cys Lys
        115                 120                 125

His Asn Asn Gly Gly Cys Gly Asp Asp Lys Leu Cys Glu Tyr Val Gly
    130                 135                 140

Asn Arg Arg Val Lys Cys Lys Cys Lys Glu Gly Tyr Lys Leu Glu Gly
145                 150                 155                 160

Ile Glu Cys Val Glu His His His His His
                165                 170

<210> SEQ ID NO 38
<211> LENGTH: 760
<212> TYPE: DNA
<213> ORGANISM: Artificial Sequence
<220> FEATURE:
<221> NAME/KEY: CDS
<222> LOCATION: (10)..(759)
<220> FEATURE:
<223> OTHER INFORMATION: Description of Artificial Sequence: Synthetic
      construct

<400> SEQUENCE: 38

```
cccggatcc atg aac att ctc tgt att ctc agc tac att tac ttc ttc gtc      51
          Met Asn Ile Leu Cys Ile Leu Ser Tyr Ile Tyr Phe Phe Val
           1               5                  10 atc ttc tac agt tta aac ctc aac aac aaa aac gag aac ttc ttg gtg        99
Ile Phe Tyr Ser Leu Asn Leu Asn Asn Lys Asn Glu Asn Phe Leu Val
 15              20                  25                  30 gtc cgc aga ctc atg aac gac gaa aag gga gaa ggt ggc ttc act agt       147
Val Arg Arg Leu Met Asn Asp Glu Lys Gly Glu Gly Gly Phe Thr Ser
                 35                  40                  45 aag aac aag gaa aac gga aac aac aac agg aac aac gag aac gaa ctc       195
Lys Asn Lys Glu Asn Gly Asn Asn Asn Arg Asn Asn Glu Asn Glu Leu
 50                  55                  60 aaa gaa gaa gga tct ttg ccc act aag atg aac gag aaa aac agt aac       243
Lys Glu Glu Gly Ser Leu Pro Thr Lys Met Asn Glu Lys Asn Ser Asn
 65                  70                  75 tcc gcg gat aag caa cca aac gac atc tcc cac gac gaa agc aag agc       291
Ser Ala Asp Lys Gln Pro Asn Asp Ile Ser His Asp Glu Ser Lys Ser
         80                  85                  90 aac agt aac aac gcc caa aac atc caa aag gaa cct gaa gag aag gaa       339
Asn Ser Asn Asn Ala Gln Asn Ile Gln Lys Glu Pro Glu Glu Lys Glu
 95                 100                 105                 110 aac tca aac ccc aac ctc gac tcg agt gaa aac tcc gct gaa agt gct       387
Asn Ser Asn Pro Asn Leu Asp Ser Ser Glu Asn Ser Ala Glu Ser Ala
                115                 120                 125 act aga agc gtc gac atc agt gaa cac aac tca aac aac ccc gaa act       435
Thr Arg Ser Val Asp Ile Ser Glu His Asn Ser Asn Asn Pro Glu Thr
        130                 135                 140 aaa gaa gaa aac gga gaa gaa cct cta gac ctg gaa att aac gaa aac       483
Lys Glu Glu Asn Gly Glu Glu Pro Leu Asp Leu Glu Ile Asn Glu Asn
145                 150                 155 gca gaa atc ggc cag gaa cct cca aac cgt ctt cac ttc gac aac gtt       531
Ala Glu Ile Gly Gln Glu Pro Pro Asn Arg Leu His Phe Asp Asn Val
    160                 165                 170 gac gac gaa gta cca cat tac tca gcc ctg agg tac aac aag gtc gag       579
Asp Asp Glu Val Pro His Tyr Ser Ala Leu Arg Tyr Asn Lys Val Glu
175                 180                 185                 190 aag aac gta acc gac gag atg ctc ttg tac aac atg atg tcc gac caa       627
Lys Asn Val Thr Asp Glu Met Leu Leu Tyr Asn Met Met Ser Asp Gln
                195                 200                 205 aac cgc aaa agc tgt gct atc aac aac ggt ggc tgc agt gac gac cag       675
Asn Arg Lys Ser Cys Ala Ile Asn Asn Gly Gly Cys Ser Asp Asp Gln
        210                 215                 220 atc tgc atc aac atc aac aac atc ggt gtg aag tgc att tgt aag gat       723
Ile Cys Ile Asn Ile Asn Asn Ile Gly Val Lys Cys Ile Cys Lys Asp
225                 230                 235 gga tac cta ctt ggt acc aag tgc att cac cac cac c                     760
Gly Tyr Leu Leu Gly Thr Lys Cys Ile His His His
    240                 245                 250
```

<210> SEQ ID NO 39
<211> LENGTH: 250
<212> TYPE: PRT
<213> ORGANISM: Artificial Sequence
<220> FEATURE:
<223> OTHER INFORMATION: Description of Artificial Sequence: Synthetic construct

<400> SEQUENCE: 39

```
Met Asn Ile Leu Cys Ile Leu Ser Tyr Ile Tyr Phe Phe Val Ile Phe
 1               5                  10                  15

Tyr Ser Leu Asn Leu Asn Asn Lys Asn Glu Asn Phe Leu Val Val Arg
             20                  25                  30

Arg Leu Met Asn Asp Glu Lys Gly Glu Gly Phe Thr Ser Lys Asn
         35                  40                  45

Lys Glu Asn Gly Asn Asn Arg Asn Asn Glu Asn Leu Lys Glu
 50                  55                  60

Glu Gly Ser Leu Pro Thr Lys Met Asn Glu Lys Asn Ser Asn Ser Ala
 65                  70                  75                  80

Asp Lys Gln Pro Asn Asp Ile Ser His Asp Glu Ser Lys Ser Asn Ser
                 85                  90                  95

Asn Asn Ala Gln Asn Ile Gln Lys Glu Pro Glu Lys Glu Asn Ser
             100                 105                 110

Asn Pro Asn Leu Asp Ser Ser Glu Asn Ser Ala Glu Ser Ala Thr Arg
         115                 120                 125

Ser Val Asp Ile Ser Glu His Asn Ser Asn Asn Pro Glu Thr Lys Glu
130                 135                 140

Glu Asn Gly Glu Glu Pro Leu Asp Leu Glu Ile Asn Glu Asn Ala Glu
145                 150                 155                 160

Ile Gly Gln Glu Pro Pro Asn Arg Leu His Phe Asp Asn Val Asp Asp
                 165                 170                 175

Glu Val Pro His Tyr Ser Ala Leu Arg Tyr Asn Lys Val Glu Lys Asn
             180                 185                 190

Val Thr Asp Glu Met Leu Leu Tyr Asn Met Met Ser Asp Gln Asn Arg
         195                 200                 205

Lys Ser Cys Ala Ile Asn Asn Gly Gly Cys Ser Asp Asp Gln Ile Cys
210                 215                 220

Ile Asn Ile Asn Asn Ile Gly Val Lys Cys Ile Cys Lys Asp Gly Tyr
225                 230                 235                 240

Leu Leu Gly Thr Lys Cys Ile His His His
                 245                 250
```

<210> SEQ ID NO 40
<211> LENGTH: 760
<212> TYPE: DNA
<213> ORGANISM: Artificial Sequence
<220> FEATURE:
<223> OTHER INFORMATION: Description of Artificial Sequence: Synthetic construct

<400> SEQUENCE: 40

```
tctgaattct cagtggtggt ggtggtggtg aatgcacttg gtaccaagta ggtatccatc    60
cttacaaatg cacttcacac cgatgttgtt gatgttgatg cagatctggt cgtcactgca   120
gccaccgttg ttgatagcac agcttttgcg gttttggtcg acatcatgt tgtacaagag   180 catctcgtcg gttacgttct ctcgaccctt gttgtacctc agggctgagt aatgtggtac   240
ttcgtcgtca acgttgtcga agtgaagacg gtttggaggt tcctggccga tttctgcgtt   300
ttcgttaatt ccaggtcta gaggttcttc tccgttttct ctttagtttt cggggttgtt   360
tgagttgtgt tcactgatgt cgacgcttct agtagcactt tcagcggagt tttcactcga   420
gtcgaggttg gggtttgagt tttccttctc ttcaggttcc ttttggatgt tttgggcgtt   480
gttactgttg ctcttgcttt cgtcgtggga gatgtcgttt ggttgcttat ccgcggagtt   540 actgttttc tcgttcatct tagtgggcaa agatccttct tctttgagtt cgttctcgtt   600
```

```
gttcctgttg ttgtttccgt tttccttgtt cttactagtg aagccacctt ctcccttttc    660
gtcgttcatg agtctgcgga ccaccaagaa gttctcgttt tgttgttga ggtttaaact     720 gtagaagatg acgaagaagt aaatgtagct gagaatacag                          760
```

<210> SEQ ID NO 41
<211> LENGTH: 272
<212> TYPE: PRT
<213> ORGANISM: Plasmodium falciparum

<400> SEQUENCE: 41

```
Met Trp Ile Val Lys Phe Leu Ile Val Val His Phe Ile Ile Cys
 1               5                  10                  15

Thr Ile Asn Phe Asp Lys Leu Tyr Ile Ser Tyr Ser Tyr Asn Ile Val
                20                  25                  30

Pro Glu Asn Gly Arg Met Leu Asn Met Arg Ile Leu Gly Glu Lys
            35                  40                  45

Pro Asn Val Asp Gly Val Ser Thr Ser Asn Thr Pro Gly Gly Asn Glu
        50                  55                  60

Ser Ser Ser Ala Ser Pro Asn Leu Ser Asp Ala Ala Glu Lys Lys Asp
 65                  70                  75                  80

Glu Lys Glu Ala Ser Glu Gln Gly Glu Glu Ser His Lys Lys Glu Asn
                 85                  90                  95

Ser Gln Glu Ser Ala Asn Gly Lys Asp Asp Val Lys Glu Lys Lys
                100                 105                 110

Thr Asn Glu Lys Lys Asp Asp Gly Lys Thr Asp Lys Val Gln Glu Lys
            115                 120                 125

Val Leu Glu Lys Ser Pro Lys Glu Ser Gln Met Val Asp Asp Lys Lys
        130                 135                 140

Lys Thr Glu Ala Ile Pro Lys Lys Val Val Gln Pro Ser Ser Ser Asn
145                 150                 155                 160

Ser Gly Gly His Val Gly Glu Glu Asp His Asn Glu Gly Glu Gly
                165                 170                 175

Glu His Glu Glu Glu Glu His Glu Asp Asp Asp Asp Glu Asp
            180                 185                 190

Asp Asp Thr Tyr Asn Lys Asp Asp Leu Glu Asp Glu Asp Leu Cys Lys
        195                 200                 205

His Asn Asn Gly Gly Cys Gly Asp Asp Lys Leu Cys Glu Tyr Val Gly
        210                 215                 220

Asn Arg Arg Val Lys Cys Lys Cys Lys Glu Gly Tyr Lys Leu Glu Gly
225                 230                 235                 240

Ile Glu Cys Val Glu Leu Leu Ser Leu Ala Ser Ser Ser Leu Asn Leu
                245                 250                 255

Ile Phe Asn Ser Phe Ile Thr Ile Phe Val Val Ile Leu Leu Ile Asn
            260                 265                 270
```

<210> SEQ ID NO 42
<211> LENGTH: 230
<212> TYPE: PRT
<213> ORGANISM: Plasmodium falciparum

<400> SEQUENCE: 42

```
Met Lys Val Ala Tyr Phe Leu Ser Val Leu Asp Leu Leu Ile Ile Phe
 1               5                  10                  15

Ser Leu Tyr Phe Asp Gly Arg Arg Ser Ala Phe Ala Gly Ile Ala Ala
                20                  25                  30
```

```
Cys Ile Arg His Gly Arg Ile Leu Gly Glu Gly Gly Glu Gln Ser Gly
             35                  40                  45

Gly Ala Ser Gly Gly Ser Ser Gly Gly Ser Ser Asp Ser Ser Gly
 50                  55                  60

Gly Leu Ser Gly Gly Ser Ser Gly Gly Pro Ser Pro Ala Gly Ser
 65                  70                  75                  80

Ser Gly Ser Gly Gly Ser Asp Pro Ala Asn Ser Ala Thr Gly Pro Gln
                 85                  90                  95

Asn Ser Thr Pro Gly Ser Gly Gly Gln Thr Gly Asp His Ser Ala Glu
            100                 105                 110

Ala Glu Asn Gly Asp Tyr Asn Glu Gln Gly Asp Asp His Gly Asp Asp
        115                 120                 125

His Gly Asp Asp His Gly Asp Asp His Gly Asp Glu Gln Asp Gly Glu
    130                 135                 140

Asp Tyr Asp Asp Ala Glu Asp Asp Leu Tyr Glu Leu Ser Glu Val
145                 150                 155                 160

Asp Glu Asn Ala Asn Leu Cys Leu Asp Asn Asn Gly Cys Gly Asp
                165                 170                 175

Asp Lys Ile Cys Glu Asn Leu Gly Lys Gly Ile Val Lys Cys Leu Cys
            180                 185                 190

Lys Pro Gly Tyr Lys Leu Val Gly Thr Glu Cys Val Glu Ser Ser Lys
        195                 200                 205

Ser Ser Ser Leu Asn Ser Phe Phe Cys Trp Phe Leu Leu Val Ile Ile
    210                 215                 220

Val Leu Ala Ser Ile Asn
225                 230

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Ser Pro Lys Glu
 1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Arg Ile Leu Gly
 1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Met Arg Ile Leu Ala
 1               5
```

```
<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Arg Ile Leu
 1

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Gly Phe Thr Ser Lys
 1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Ser Leu Pro Thr Lys
 1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Ile Ala Ala Cys
 1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Gly Gly Glu Gln
 1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 51

Gly Asp Ser Ser Gly
 1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Ser Ser Gly Gly
 1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Ser Gly Gly Leu
 1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Asp Asn Asn Gly
 1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Met Arg Ile Leu Gly Glu
 1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Arg Ile Leu Gly Glu
 1               5

<210> SEQ ID NO 57
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      6x His tag

<400> SEQUENCE: 57

His His His His His His
  1               5
```